(12) United States Patent
Wernig et al.

(10) Patent No.: US 11,965,034 B2
(45) Date of Patent: Apr. 23, 2024

(54) ANTIFIBROTIC ACTIVITY OF CD47 BLOCKADE IN THE LIVER

(71) Applicant: The Board of Trustees of the Leland Stanford Junior University, Stanford, CA (US)

(72) Inventors: Gerlinde Wernig, Stanford, CA (US); Irving L. Weissman, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 26 days.

(21) Appl. No.: 17/668,068

(22) Filed: Feb. 9, 2022

(65) Prior Publication Data

US 2022/0275084 A1 Sep. 1, 2022

Related U.S. Application Data

(62) Division of application No. 16/487,051, filed as application No. PCT/US2018/020285 on Feb. 28, 2018, now Pat. No. 11,286,301.

(60) Provisional application No. 62/465,086, filed on Feb. 28, 2017.

(51) Int. Cl.

| | | |
|---|---|---|
| A61K 39/395 | (2006.01) | |
| A61K 38/17 | (2006.01) | |
| A61K 45/06 | (2006.01) | |
| A61P 1/16 | (2006.01) | |
| C07K 16/28 | (2006.01) | |
| G01N 33/53 | (2006.01) | |
| G16H 15/00 | (2018.01) | |
| G16H 80/00 | (2018.01) | |
| H04L 9/40 | (2022.01) | |
| H04W 12/02 | (2009.01) | |
| A61K 39/00 | (2006.01) | |
| A61P 11/00 | (2006.01) | |

(52) U.S. Cl.
CPC ...... *C07K 16/2896* (2013.01); *A61K 38/1774* (2013.01); *A61K 39/3955* (2013.01); *A61K 45/06* (2013.01); *A61P 1/16* (2018.01); *C07K 16/2803* (2013.01); *G01N 33/53* (2013.01); *G16H 15/00* (2018.01); *G16H 80/00* (2018.01); *H04L 63/0281* (2013.01); *H04L 63/04* (2013.01); *H04L 63/0442* (2013.01); *H04L 63/101* (2013.01); *H04L 63/107* (2013.01); *H04W 12/02* (2013.01); *A61K 2039/505* (2013.01); *A61P 11/00* (2018.01); *C07K 2317/76* (2013.01)

(58) Field of Classification Search
CPC .... C07K 16/2896; A61K 39/3955; A61P 1/16
See application file for complete search history.

(56) References Cited

U.S. PATENT DOCUMENTS

| | | |
|---|---|---|
| 2004/0147731 A1 | 7/2004 | Parkos et al. |
| 2015/0266942 A1* | 9/2015 | Tian ............... C07K 14/71 |
| | | 435/254.2 |
| 2016/0159920 A1 | 9/2016 | Wang et al. |
| 2016/0257751 A1* | 9/2016 | Swanson ......... C07K 16/30 |

FOREIGN PATENT DOCUMENTS

| | | |
|---|---|---|
| WO | WO2014149477 | 9/2014 |
| WO | WO 2016141328 | 9/2016 |

OTHER PUBLICATIONS

Dorn et al, 2014. Laboratory Investigation 94: 394-408.*
Sharifi-Sanjani et al, 2014. J Am Heart Assoc. pp. 1-21.*
Lin et al, 2012. Protein Expression and Purification. 85: 109-116.*
Alswat et al, 2010. Saudi Journal of Gastroenterology. 16(2): 133-9.*
Karsdal et al. (2015) "Novel Insights into the Function and Dynamics of Extracellular Matrix in Liver Fibrosis," American Journal of Physiology-Gastrointestinal and Liver Physiology, vol. 308, pp. 807-830.
Kim et al. (2012) "Anti-CD47 Antibodies Promote Phagocytosis and Inhibit the Growth of Human Myeloma Cells" Leukemia, vol. 26, Iss. 12, pp. 2538-2545.
Kojima et al. (2016) "CD47-Blocking Antibodies Restore Phagocytosis and Prevent Atherosclerosis," Nature, vol. 536, No. 7614, pp. 86-90.
Maimaitiyiming et al. (2015) "CD47 Deficiency Protects Mice From Diet-induced Obesity and Improves Whole Body Glucose Tolerance and Insulin Sensitivity", Scientific Reports. vol. 5. No. 1. 9, XP055775638.
Norman-Burgdolf et al. (2016) "Role of CD47 in Obesity-Associated Metabolic Dysfunctions", Theses and Dissertations Pharmacology and Nutritional Sciences, pp. 113-117.
Rogers et al. (2012) "Activated CD47 Regulates Multiple Vascular and Stress Responses: Implications for Acute Kidney Injury and its Management," Am J Physiol Renal Physiol, 08 Vol. 303, pp. F1117-F1125.
Wernig et al. (2017) "Unifying Mechanism for Different Fibrotic Diseases," Proceedings of the National Academy of Sciences USA, vol. 114, No. 18, pp. 4757-4762.

* cited by examiner

*Primary Examiner* — Zachary C Howard
(74) *Attorney, Agent, or Firm* — Pamela J. Sherwood; Bozicevic, Field and Francis LLP

(57) ABSTRACT

Compositions and methods are provided for treating fibrosis in a mammal by administering a therapeutic dose of a pharmaceutical composition.

10 Claims, 49 Drawing Sheets

Lung Fibrosis wt BM transplant parabiosis

| Serum markers | PAX8 c-Jun + Dox | PAX8 c-Jun - Dox | Normal values |
|---|---|---|---|
| BUN | 393 | 30 | 20.3 - 24.7 mg/dL |
| Creatinine | 4.6 | 0.2 | 0.1 - 1.1 mg/dL |
| BUN/Crea Ratio | 178.6 | | |
| T Protein | 5.8 | 5.2 | 5.0 - 6.2 mg/dL |
| Albumin | 2.2 | 2.2 | 3.2 - 3.6 g/dL |
| Sodium | 177 | 152 | 114 - 154 mmol/L |
| Potassium | 7.9 | 9.5 | 3.0 - 9.6 mmol/L |
| Chloride | 124 | 116 | N/A mmol/L |
| Anion Gap | 63.6 | 20.8 | N/A mmol/L |

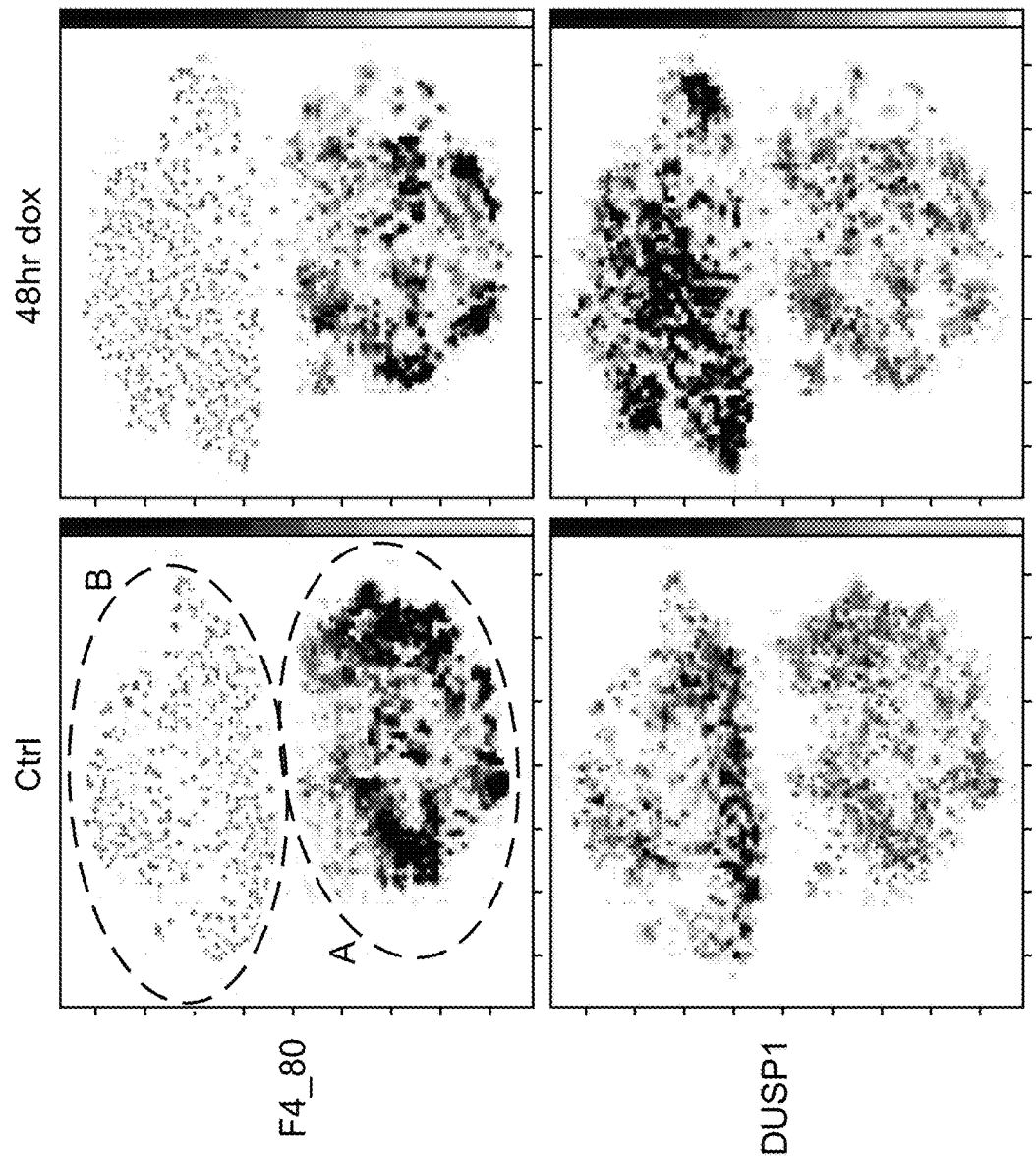

FIG. 7D
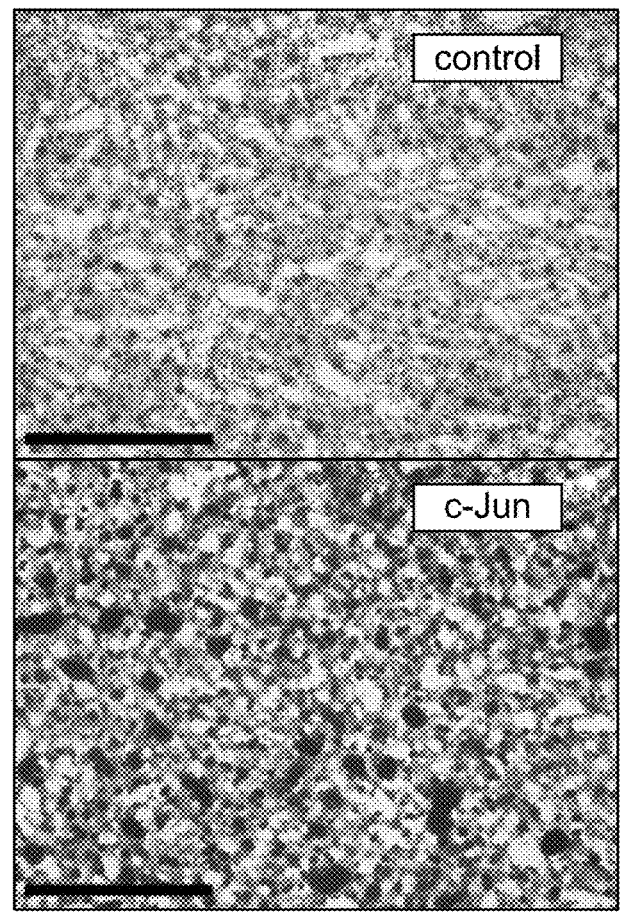
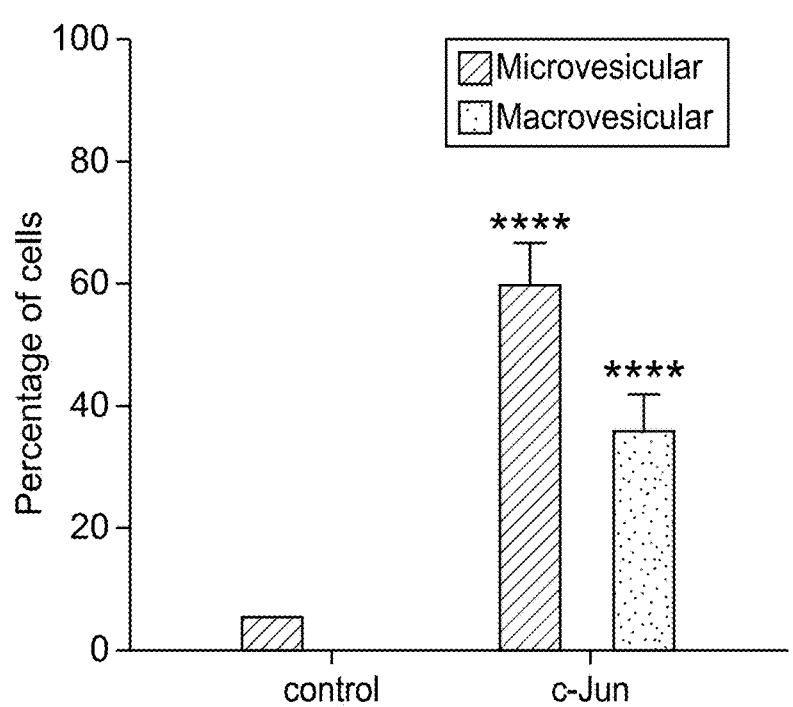

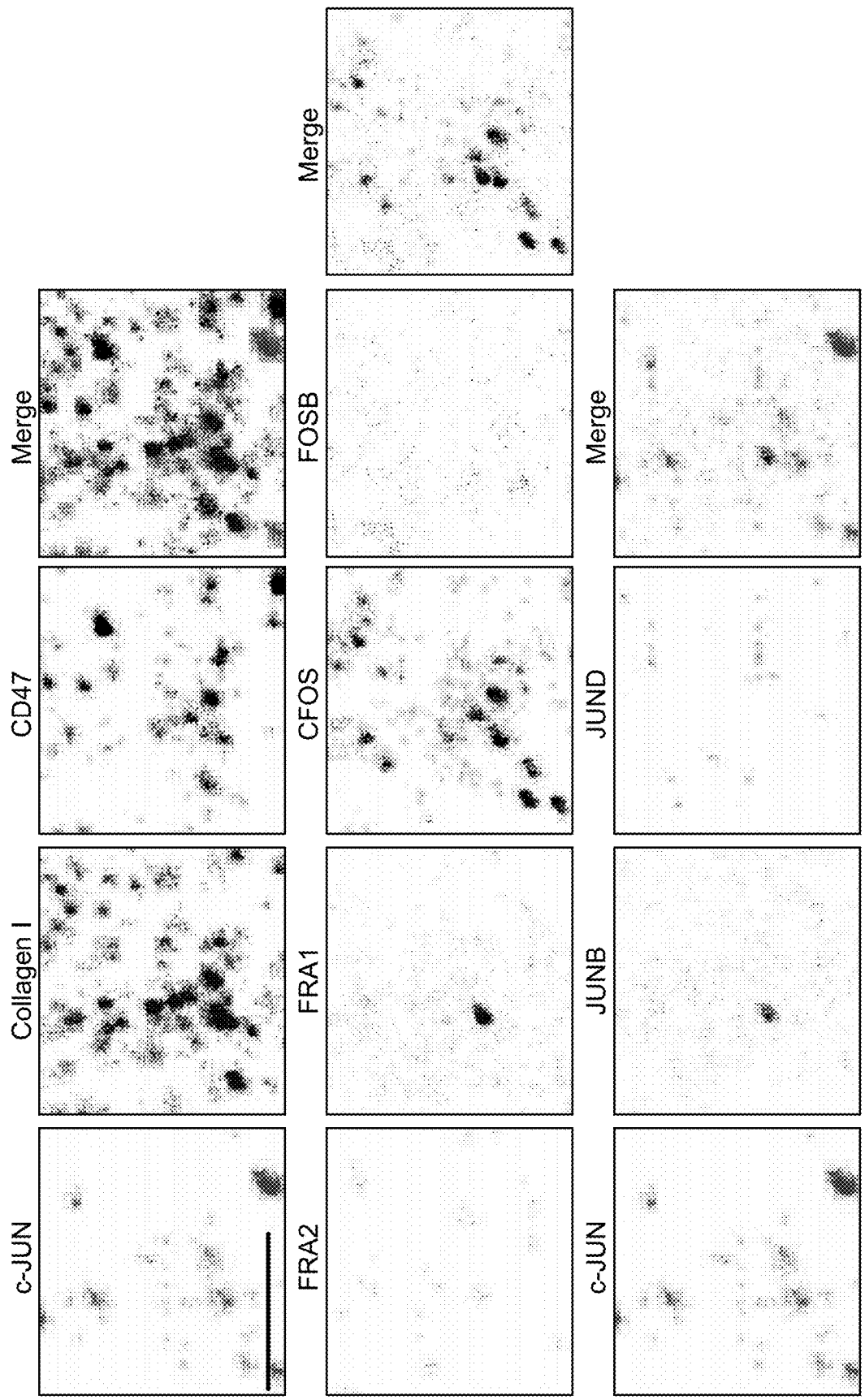

Lung Fibrosis

FIG. 13A

| Probe ID | Gene |
|---|---|
| 1452378_at | Malat1 |
| 1426817_at | Mki67 |
| 1457307_at | Apol11b |
| 1439411_a_at | Xpo7 |
| 1417373_a_at | Tuba4a |
| 1436058_at | Rsad2 |
| 1421009_at | Rsad2 |
| 1452666_a_at | Tmcc2 |
| 1419921_s_at | Usp7 |
| 1455451_at | AI449310 |
| 1449077_at | Eraf |
| 1420618_at | Cpeb4 |
| 1456438_x_at | Rpn1 |
| 1454905_at | Ibtk |
| 1434437_x_at | Rrm2 |
| 1417750_a_at | Slc25a37 |
| 1434853_x_at | Mkrn1 |
| 1438855_x_at | Tnfaip2 |
| 1417206_at | Urod |
| 1436898_at | Sfpq |
| 1434502_x_at | Slc4a1 |
| 1453220_at | 4432416J03Rik |
| 1417508_at | Rnf19a |
| 1423651_at | Isca1 |
| 1430379_at | 5830411K21Rik |
| 1436454_x_at | Fen1 |
| 1426475_at | Hmbs |
| 1439581_at | 6330403L08Rik |
| 1441904_x_at | 9130005N14Rik |
| 1452661_at | Tfrc |
| 1418699_s_at | Fech |
| 1418199_at | Hemgn |
| 1428108_x_at | Tmcc2 |
| 1435122_x_at | Dnmt1 |
| 1455618_x_at | Tspan33 |
| 1424460_s_at | Lpcat1 |
| 1417636_at | Slc6a9 |
| 1416203_at | Aqp1 |
| 1423812_s_at | AW146242 |
| 1416464_at | Slc4a1 |
| 1435344_at | Tfdp2 |
| 1426677_at | Fina |
| 1418493_a_at | Snca |
| 1419920_s_at | Usp7 |
| 1460016_at | Tmem164 |
| 1460223_a_at | Epb4.9 |
| 1435225_s_at | Brpf3 |
| 1443673_x_at | --- |
| 1450234_at | Ms4a6c |
| 1451608_at | Tspan33 |

No c-Jun    24h c-Jun

FIG. 13A (Cont.)

No c-Jun   24h c-Jun

| Probe ID | Gene |
|---|---|
| 1427865_at | --- |
| 1428720_s_at | Igl-C2, Igl-C3 |
| 1448830_at | Dusp1 |
| 1429321_at | Rnf149 |
| 1450840_a_at | Rpl39 |
| 1416656_at | Clic1 |
| 1455588_at | Lyrm4 |
| 1439200_at | --- |
| 1436712_at | Pla2g4c |
| 1423100_at | Fos |
| 1435646_at | Ikbkg |
| 1416037_a_at | Cct2 |
| 1430542_a_at | Slc25a5 |
| 1421802_at | Ear1 |
| 1423542_at | Klk7 |
| 1430656_a_at | Asnsd1 |
| 1417426_at | Srgn |
| 1460302_at | Thbs1 |
| 1417864_at | Pgk1 |
| 1416503_at | Lxn |
| 1455997_a_at | Uqcrb |
| 1432338_at | 4833419O12Rik |
| 1435323_a_at | Mboat1 |
| 1427837_at | Igkv15-103 |
| 1415724_a_at | Cdc42 |
| 1454698_at | Ptplad1 |
| 1420804_s_at | Clec4d |
| 1425519_a_at | Cd74 |
| 1448430_a_at | Naca |
| 1454896_at | Rbpj |
| 1417936_at | Ccl9 |
| 1450648_s_at | H2-Ab,1Rmcs2, Rmcs5 |
| 1448950_at | Il1r1 |
| 1421811_at | Thbs1 |
| 1415839_a_at | Npm1 |
| 1422613_a_at | Rpl7a |
| 1425993_a_at | Hsph1 |
| 1426083_a_at | Btg1 |
| 1448162_at | Vcam1 |
| 1429281_at | 2610008E11Rik |
| 1449289_a_at | B2m |
| 1436064_x_at | Rps24 |
| 1436946_s_at | Gng5 |
| 1455249_at | --- |
| 1448392_at | Sparc |
| 1449254_at | Spp1 |
| 1429485_a_at | Utp11l |
| 1448566_at | Slc40a1 |
| 1419772_at | --- |
| 1424164_at | Mrpl50 |

ANTIFIBROTIC ACTIVITY OF CD47 BLOCKADE IN THE LIVER

CROSS-REFERENCE TO RELATED APPLICATIONS

This application claims benefit and is a Divisional of application Ser. No. 16/487,051, filed Aug. 19, 2019, which claims benefit of International Application No. PCT/US2018/020285, filed Feb. 28, 2018, which claims benefit of U.S. Provisional Application No. 62/465,086, filed Feb. 28, 2017, which applications are incorporated herein by reference in their entirety.

FEDERALLY SPONSORED RESEARCH AND DEVELOPMENT

This invention was made with Government support under contract HL099999 awarded by the National Institutes of Health. The Government has certain rights in the invention.

BACKGROUND OF THE INVENTION

Fibrosis, defined by the excessive accumulation of extracellular matrix components (ECM) in and around inflamed or damaged tissue, is associated with several inflammatory conditions. In these situations, normal tissue repair response turns into an irreversible fibrotic response through dysregulation of response to stress or injury. Fibrosis can lead to permanent scarring, organ malfunction and, ultimately, death, as seen in end-stage liver disease, kidney disease, idiopathic pulmonary fibrosis (IPF), retinal fibrosis, and heart failure from cardiac fibrosis. Fibrosis also influences tumor invasion and metastasis, chronic graft rejection and the pathogenesis of many progressive myopathies.

Many distinct triggers can contribute to the development of progressive fibrotic disease, but regardless of the initiating events, a common feature is the activation of ECM-producing myofibroblasts, which are the key mediators of fibrotic tissue remodeling. Many elements of the innate and adaptive immune response participate in the differentiation and activation of fibroblasts. During equilibrium, tissue-resident fibroblasts are quiescent. To repair tissues after injury, these tissue-resident fibroblasts are activated and transformed into myofibroblasts. Myofibroblasts secrete large amounts of ECM, aiding in contracture and closure and orchestrating many aspects of the healing response. Myofibroblast activation, proliferation and survival are mediated by a variety of secreted, soluble and physical factors in the milieu, such as cytokines including IL-1, TNF, TGF-β1 and IL-13, growth factors such as CTGF and PDGF, and matrix factors such as hyaluronan fragments, mechanical stress and stiffness. During normal wound healing, myofibroblasts undergo apoptosis after re-epithelialization of the wound, but myofibroblasts in fibrotic loci are resistant to programmed cell death. Pathways that elicit and recruit high numbers of myofibroblasts and those that engender resistance to apoptosis are active areas of fibrosis research.

Because ECM-producing myofibroblasts are the final common pathogenic cell in fibrotic diseases, any therapy that successfully ablates their activity could have broad antifibrotic activity. Targeting key inflammatory pathways may also be useful in the treatment of fibrosis. Antifibrotic compositions and methods of use thereof are of great clinical and humanitarian interest. The present invention addresses this need.

SUMMARY OF THE INVENTION

The present invention provides compositions and methods useful for prevention or treatment of fibrosis via inhibition of CD47 and SIRPα pathways. In some embodiments the fibrosis is a pulmonary fibrosis, such as idiopathic pulmonary fibrosis. In some embodiments the fibrosis is associated with cancer and tumor growth, i.e. tumor related tissue fibrosis, including without limitation pancreatic cancer. In other embodiments the fibrosis is associated with chronic inflammation or injury such as irradiation in tissues, including without limitation fibrosis of liver, lung, kidney, uterus, the eye and the lens, IgG4-related disease, chronic GvHD, and the like.

In some embodiments, conditions for treatment are fatty liver diseases, such as non-alcoholic fatty liver disease (NAFLD) and non-alcoholic steatohepatitis (NASH). These conditions are associated with fatty infiltration of the liver and frequently involve liver fibrosis. Treatment by the methods provided herein can impact multiple pathways of these diseases through reversing effects of c-JUN induction, which effects can include up-regulation of CD47, increased lipid uptake by hepatocytes and a resulting decrease in phagocytosis of pathogenic cells.

An anti-CD47 agent for use in the methods of the invention interferes with binding between CD47 present on the fibrotic cell and SIRPα present on a phagocytic cell. Such methods increase phagocytosis of the fibrotic cell. Suitable anti-CD47 agents include soluble SIRPα polypeptides; soluble CD47; anti-CD47 antibodies, anti-SIRPα antibodies, and the like, where the term antibodies encompasses antibody fragments and variants thereof, as known in the art. In some embodiments the anti-CD47 agent is an anti-CD47 antibody. In some embodiments the anti-CD47 antibody is a non-hemolytic antibody. In some embodiments the antibody comprises a human IgG4 Fc region.

In some embodiments of the invention, compositions and methods useful for prevention or treatment of fibrosis via inhibition of c-Jun pathways are provided. In some embodiments, RNA interference is used to inhibit c-Jun. In other embodiments, a small molecule inhibitor is used to inhibit c-Jun. In some embodiments, a PI3K pathway inhibitor is used to treat or reverse c-Jun mediated fibrosis. In some embodiments, a VEGF pathway inhibitor is used to treat or reverse c-Jun mediated fibrosis.

In other embodiments, a fibrosis is selected for treatment with a combination therapy of the present invention. In some embodiments, the combination therapy is a combination of an inhibitor of CD47 pathways, and an inhibitor of c-Jun.

In some embodiments, a diagnosis of fibrosis is made by obtaining a biological sample and determining the CD47 concentration, where elevated levels of CD47 indicate potential fibrosis. In some embodiments the biological sample is blood or a derivative thereof, e.g. plasma, serum, etc. The individual may be pre-clinical for fibrosis. In some embodiments, a diagnosis of fibrosis is made by obtaining a biological sample and determining the c-Jun concentration, where elevated levels of c-Jun indicate potential fibrosis. In some such embodiments, an individual thus diagnosed is treated using the methods described herein.

Compositions and kits for practicing the methods and/or for use with the systems of the disclosure are also provided.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Included in the drawings are the following figures.

(FIG. 1A) Morphologic (haematoxylin and eosin staining, trichrome staining) and molecular markers (Collagen1 and c-JUN (Red), Smooth Muscle Actin (SMA, Green) with DAPI (Grey, nuclear counterstain) of lung fibrosis tissue. (FIG. 1B) Representative examples of biopsies of patients with scar tissue, skin biopsies of systemic sclerosis, normal skin tissue, bone marrow fibrosis and normal bone marrow biopsies demonstrating fibrosis with collagen production in blue by trichrome staining and nuclear c-JUN expression in red, counterstained with DAPI. (FIG. 1C) Quantification of c-JUN expression in 49 biopsies of scar tissue, 104 skin biopsies, 38 gastrointestinal biopsies and 6 heart biopsies of systemic sclerosis patients, 14 normal control skin biopsies, 36 lung fibrosis biopsies, 3 normal control lung biopsies, 57 bone marrow fibrosis biopsies and 5 normal control bone marrow biopsies demonstrates a significant difference in c-JUN expression in fibroblasts in scar tissue, systemic sclerosis, lung fibrosis and marrow fibrosis compared to predominantly negative c-JUN expression in normal skin, normal lung and normal bone marrow. **** $P<0.0001$; Anova test. (FIG. 1D) Sections of normal lung tissue and lung fibrosis tissue stained with antibodies to c-JUN (Red) with cell lineage markers CK7 (Cytokeratin 7, Epithelia) and CD31 (Endothelia) counterstained with DAPI (Grey), white asterix indicate autofluorescence. (FIG. 1E) Immunofluorescence staining of lung sections from pulmonary arterial hypertension (PAH) and lung fibrosis biopsies showing positive nuclear FRA-2 staining in smooth muscle cells of pathologically thickened vessels in PAH lung tissue, but not in fibrosis plaque in lung fibrosis tissue. Scale bar, 100 μm.

(FIG. 2A) Representative images of expression of don't eat me signal factors Calreticulin and CD47 (Green) in Collagen1 (Red) positive pathogenic fibroblasts, and c-JUN (Red) expression in macrophages (CD68, green). (FIG. 2B and FIG. 2C) Knock down of c-JUN in lung fibrosis negatively impacts proliferation of pathogenic fibrosis. (FIG. 2B) Quantification of proliferation of human lung derived IPF and normal fibroblasts infected with knock down hairpins. (FIG. 2C) Quantification of proliferation of human lung derived IPF fibroblasts infected with control and knock down hairpins. The fibroblasts were infected with one of two lentiviral shRNA hairpins also expressing RFP or a control vector expressing GFP. Infected cells were sorted by FACS and plated at a density of 100 cells per 96-well and the number of red and green fluorescent cells was counted 24, 48, and 72 hours after plating. Data (mean+/−s.e.m.) represents 4 replicates (2 way ANOVA). * $P<0.05$,  $P<0.01$, * $P<0.001$. (FIG. 2D-2E) ViSNE analysis of dissociated lung from lung fibrosis patient reveals enhanced c-JUN and AKT signaling intensity in vivo. (FIG. 2D) Peripheral blood mononuclear cells (PBMCs) and dissociated cells from normal lung were stained with the same antibody panel and analyzed together with the sample from lung fibrosis tissue for reference of different cell types. Each point in the viSNE map represents an individual cell colored by sample identity. Schematic diagram of the location of indicated cell types on viSNE map based on the expression of lineage specific markers. Epithelial cells (Epi). Natural killer cells (NK). plasmacytoid dendritic cells (pDC). Endothelial cells (EC). Macrophage (Mac). (FIG. 2E) ViSNE analysis demonstrates activation of pc-JUN, pAKT and related molecules as well as increased expression of CD47 in endstage fibrosis fibroblasts in vivo. Each point represents a cell event colored for its expression level of indicated markers. Red is for high expression and blue for low. Scale bar, 100 μm.

(FIG. 3A) Doxycycline mediated systemic c-Jun expression in adult mice was lethal within a week post induction in the hybrid F1 129/C57Bl/6 genetic background ($P<0.0001$ by Kaplan-Meyer survival analysis; n=10 animals, two independent experiments) and 38 days in the hybrid F1 129/BDF1 genetic background ($P<0.0001$ by Kaplan-Meyer survival analysis; n=7 animals, two independent experiments). (FIG. 3B) Histological analysis revealed significant fibrosis of the bone marrow. H&E stained sections (top) showed a severe reduction of hematopoiesis which is replaced by a population of homogeneously expanded fibroblasts. Trichrome staining (middle) showed the pathologic deposition of abundant collagenous extracellular matrix in blue (representative pictures, n=17 mice analyzed). The expanded bone marrow fibroblasts strongly labeled with smooth muscle actin (brown cytoplasmic staining, bottom). (FIG. 3C) Quantification of fibrosis in c-Jun-induced and control bone marrow revealed that on average 80% of the area of the sections were trichrome-positive. Trichrome stains label cross-linked collagen and staining is used in the clinical setting to grade organ involvement by fibrosis (mean of 10 high power fields (40×) of trichrome stained sections, n=17 mice). (FIG. 3D) 38 mouse cytokines/chemokines have been assayed in the serum after 48 hours of systemic c-Jun induction in mice by cytokine multiplex assay and IL27, IL-6, IL-18, GROA, LIX and IL-22 found to be significantly increased in the serum of c-Jun induced animals but not controls (n=3 animals per group and the experiment has been performed twice, p-values have been calculated by Student's t-test and significant values indicated as follows: *<0.05, <0.01, *<0.001). (FIG. 3E, FIG. 3F) c-Jun induced fibrosis was partially rescued by wildtype hematopoietic cells following bone marrow transplantation and also in c-Jun induced mice parabiosed to wild-type syngeneic mice (n=10 transplanted mice, n=2 parabiosed mouse pairs). (FIG. 3G, FIG. 3H) Extent of fibrosis was quantified at 10.3% in sections of c-Jun induced animals transplanted with wild type bone marrow and at 29% in sections of parabiosed c-Jun induced animals as described in (FIG. 3C) (mean of ten 40× fields of trichrome stained sections). Scale bars, 100 μm.

(FIG. 4A) Dox-mediated ubiquitous c-Jun expression in adult mice resulted in specific phenotypic changes such as significant thickening and fibrosis of the skin, the gastrointestinal junction and quantified at 89% dermal fibrosis, 67% gastro-esophageal fibrosis (mean of 10 high power fields (40×) of trichrome stained sections). (FIG. 4B) Lung-specific c-Jun induction resulted in characteristic patchy peribronchial and subpleural fibrosis with extensive interstitial free collagen deposition as highlighted by blue deposition on trichrome stain and quantified at 34% lung fibrosis (mean of 10 high power fields (40×) of trichrome stained sections). c-Jun induction in the lung resembled idiopathic lung fibrosis and was associated with increased numbers of interstitial macrophages labeled with CD68 (inset). n=3 animals. (FIG. 4C) Representative view of a kidney (4× low power) of a c-Jun Pax8 rtTA mouse (out of 5 animals) 60 days after dox induction and demonstrated 30-40% interstitial fibrosis and tubular atrophy consistent with a primary tubulo-interstitial nephropathy. The inserts represent high power views (40×) of the abnormal areas, a PASd stain (top) labels intact basement membranes of glomeruli and tubuli, the H&E stain demonstrates increased interstitial fibrosis (middle), and a trichrome stain in blue shows abundant abnormal extracellular collagen matrix deposition (bottom). Analysis of the serum showed increased kidney enzymes BUN and creatinin, but normal protein/albumin and electrolyte concentrations in c-Jun induced animals. (FIG. 4D) The bladder as shown by H&E and trichrome staining and quantified at 82% bladder fibrosis (mean of 10 high power fields (40×) of trichrome stained sections). (FIG. 4E) H&E, Trichrome, c-Jun and dapi stained sections of liver from c-Jun inducible mice 8 days after a single intrahepatic injection of doxycycline. (FIG. 4F) H&E, Trichrome, c-Jun and dapi stained sections of uterus from c-Jun inducible mice 8 days after a single intrauterine injection of doxycycline. (FIG. 4G) Representative images of Trichrome and c-Jun stained sections of skin and (FIG. 4H) peritoneum of wild type and c-Jun induced mice 8 days post surgery. We made 1 cm incisions into the dorsal back skin of wildtype and c-Jun mice. Intraperitoneal abrasions have been initiated in wildtype and c-Jun mice by brushing of the peritoneum and 30 ul of doxycyline injected into the wounded skin daily and into the intraabdominal adhesion once at surgery. Scale bar, 100 µm.

FIG. 5A-5D. Transcriptional and signaling pathway rewiring in response to c-Jun. (FIG. 5A) Genome-wide transcriptional profiling in mice at 24 hours after c-Jun induction in the bone marrow in vivo revealed upregulation of c-Jun and Fos, another AP-1 transcription factor as well as a variety of fibrogenesis associated genes. Gene expression studies were performed in triplicate per each time point and bone marrow of three mice was pooled per array. (FIG. 5B) Gene set enrichment analysis (GSEA) revealed a significant enrichment of a fibrosis signature gene set in the upregulated genes as early as 24 h after dox treatment. (FIG. 5C) ViSNE maps of bone marrow derived primary fibroblast co-cultures before (Ctrl) and after c-Jun induction (48 hr dox), were generated by considering all 12 surface markers analyzed. One subpopulation was positive with macrophage lineage markers including F4_80 and the other showed higher expression level of c-Jun related molecules such as Dusp1. Each point in the viSNE map represents an individual cell and its color represents its degree of F4_80 (top) or Dusp1 (bottom) expression, blue colors represent low expression and yellow to red colors high expression. (FIG. 5D) Conditional density visualization (DREVI plots) of the relationship between Phospho-c-Jun (pc-Jun) and Phospho-AKT (pAkt) (top), pc-Jun and pErk (middle), and pc-Jun and Dusp1 (bottom) in F4_80 negative (subset B) versus F4_80 positive (subset A) bone marrow-derived adherent cells 48 hours after c-Jun induction. The visualization method described how the y-axis molecule changes as a function of the x-axis molecules. Dark red (maximal color) represents the most likely y-axis molecule value in the corresponding x-axis molecular value. A response function (white curve) is fit to the region of highest conditional density. Representative of two independent series.

(FIG. 6A) Bone marrow-derived fibroblasts demonstrated a 10-fold decreased doubling time following dox treatment. Data (mean+/−s.e.m.) represent three replicates and two independent experiments; ** $P<0.0001$; paired Student's t-test. (FIG. 6B) Bone marrow-derived fibroblasts showed a 100-fold and >1,000-fold increased migration 2 and 24 hours after dox treatment, respectively. Data (mean+/−s.e.m.) represent three replicates and two independent experiments;  $P<0.01$; paired Student's t-test. (FIG. 6C) Targeted small molecule screen revealed that blockade of PI3K, Vegf, Pdgfr and Tgfb pathways completely inhibited c-Jun-induced migration. Data (mean+/−s.e.m.) represent two replicates and two independent experiments; * $P<0.001$; paired Student's t-test. (FIG. 6D) Treatment with CD47 antibody doubled the removal of primary c-Jun expressing fibroblasts by phagocytosis. Data (mean+/−s.e.m.) represent two replicates and two independent experiments;  $P<0.01$; paired Student's t-test. (FIG. 6E) Lung restricted c-Jun induction generated significant peribronchial, interstitial and subpleural lung fibrosis (top panel right). Subsequent treatment targeting the don't eat me pathway with anti-CD47 antibody (MIAP 410, also known as clone 3) reversed the fibrosis to 5% (top panel left, see also FIG. 6H). (FIG. 6F) Quantification of extent of lung fibrosis following lung-restricted dox administration followed by anti CD47 treatment. n=3 mice per experiment, 2 independent experiments, paired Student's t-test. (FIG. 6G, FIG. 6J) Blockage of the PI3K and VEGF pathways prevented c-Jun mediated bone marrow fibrosis which was assessed at 1.5% and 5.5% (see also FIG. 6H and FIG. 6K). Representative micrographs from 3 animals, 2 independent experiments. (FIG. 6H, FIG. 6K) Quantification of bone marrow fibrosis after PI3K inhibition (FIG. 6G) and VEGF inhibition (FIG. 6J). (FIG. 6I) Blockage of the PI3K pathway normalized c-Jun mediated dermal skin thickening and collagen deposition after systemic c-Jun induction. Data (mean+/−s.e.m.) represent n=3 replicates, 2 independent experiments; * $P<0.05$; paired Student's t-test. Scale bar, 100 µm.

FIG. 7A-7E. c-Jun expression induced fatty liver change (FIG. 7A) Systemic c-Jun induction also resulted in severe paleness and substantially increased liver mass. (FIG. 7B) Characteristic liver enzymes were elevated in the serum of dox-treated mice. (FIG. 7C) Histopathology revealed micro- and macro-vesicular changes in the liver from dox-treated mice. (FIG. 7D) Representative images of Oil-Red O stained section of liver from control and c-Jun induced mouse model. Percentage area of intracellular lipid droplets were assessed for four groups of 100 cells. ** $P<0.0001$; paired Student's t-test. Data (mean+/−s.e.m.) represents 2 replicates of two independent experiments. Representative histology at 20× magnification of 2 out of 4 animals is shown. (FIG. 7E) Inhibition of PDGFR pathway fully reversed micro and macrovesicular steatosis in c-Jun induced mice after 28 days of treatment (bottom panel). Presence of micro- and macrovesicular fat droplets was assessed in 400 cells. Littermate controls treated with doxycycline did not develop fatty liver change (top right panel) ** $P<0.0001$; paired Student's t-test. Data (mean+/−s.e.m.) represents 3 replicates of two independent experiments. Representative histology at 40× magnification of 3 out of 9 animals is shown. Scale bar, 100 µm.

(FIG. 8A) Representative c-JUN and Trichrome staining of different fibrosing conditions suggest a significantly higher fraction of collagen-producing fibroblasts with higher level expression of c-JUN. (FIG. 8B) JUNB, JUND and FRA-1 (Red) is absent in the normal lung and lung fibrosis tissues. (FIG. 8C) H&E- and Trichrome-stained sections of normal lung tissue and pulmonary arterial hypertension (PAH) tissue with only minimal perivascular fibrosis in blue on trichrome stain and a pathological thickened vessel (PAH-lung, lower right corner). (FIG. 8D) c-FOS and FOSB (Red), SMA (Green) and DAPI (Grey) staining of lung tissue from normal, PAH and fibrosis conditions showed a minor subset of fibroblasts in fibrotic plaques express nuclear c-FOS and FOSB. (FIG. 8E) c-JUN (Red) expression in PAH tissue counterstained with cell type markers SMA, CD31, CK7 and CD68. Scale bar, 100 µm.

FIG. 9. MIBI further demonstrates expression of c-JUN but not FRA-2 in fibrotic plaques in human idiopathic pulmonary fibrosis. (A) Representative MIBI analysis of lung fibrosis samples stained with metal-conjugated antibodies. In total, 9 different markers c-JUN, JUNB, JUND, FRA1, FRA2, COFS, FOSB, Collagen1 and CD47 were analyzed. Scale bar, 50 µm.

(FIG. 10A) Lung fibrosis sections co-stained with CD47 (Green) and Collagen1 (Red), c-JUN (Red) and Calreticulin (Green), c-JUN (Red) and CD68 (Green) an DAPI (Grey) to highlight nuclei. (FIG. 10B) Quantitative RT-PCR to detect the efficiency of c-JUN knock-down with hairpin #2 and #3. Scale bar, 100 µm.

(FIG. 11A) Targeting construct of c-Jun doxycycline inducible mice. (FIG. 11B) Southern blot showing positively targeted ES cells with c-Jun. (FIG. 11C, FIG. 11D) Protein expression of c-Jun in whole bone marrow by western plot after 48 hours of induction with doxycycline and after 7 days by intracytoplasmic flow cytometric analysis. (FIG. 11E) c-Jun expression was confirmed by western blot and immune staining in primary bone marrow derived fibroblasts from c-Jun rtTA mouse after 3 passages in culture after 2 days of Dox induction and control without Dox. (FIG. 11F) Southern blot showing positively targeted ES cells with Junb. (FIG. 11G) Protein expression of Junb by western plot after 48 hours of induction with doxycycline. (FIG. 11H) Histomorphologic analysis of the bone marrow of Junb expressing mice. (FIG. 11I) Single femur counts revealed normal cellularity for age in the bone marrow. Data (mean+/−s.e.m.) are from five independent replicates. P=ns; paired Student's t-test was used to determine significant changes. Scale bars represent 100 µm.

(FIG. 12A) Single femur counts revealed severe cytopenia in the bone marrow. Data (mean+/−s.e.m.) are from four independent replicates. * $P<0.001$ (paired Student's t-test). (FIG. 12B) 7AAD/annexin V staining demonstrated increased apoptosis in c-Jun expressing hematopoietic precursors. Data (mean+/−s.e.m.) represent three replicates and two independent experiments.  $P<0.01$, * $P<0.05$, ** $P<0.01$; paired Student's t-test (FIG. 12C) Long-term intratracheal aerosol treatment of control mice with doxycycline and control or c-Jun mice with PBS did not result in significant pulmonary fibrosis, magnification represents 200-fold. (FIG. 12D) Established intrapulmonary fibrosis after 21 days of intratracheal dox treatment reversed at 300 days. (FIG. 12E) c-Jun is widely expressed in many cell types in the bone marrow after 48 hours of systemic c-Jun induction in dox inducible c-Jun mice. (FIG. 12F) c-Jun is widely expressed in most organs and cell types after 48 hours of systemic c-Jun induction in vivo in dox inducible c-Jun mice. Scale bars represent 100 µm.

FIG. 13A-13D. Dissection of transcriptional response and signaling re-wiring induced by c-Jun. (FIG. 13A) Top 100 differentially expressed genes after genome-wide transcriptional profiling at 24 hours after c-Jun induction in vivo. (FIG. 13B) Ingenuity analysis reveals activation of MAPK pathway at 24 hours post c-Jun induction. (FIG. 13C) viSNE map of bone marrow derived primary fibroblast co-cultures before (Ctrl) and after c-Jun induction (48 hr Dox), showed spatially distinct subsets based on macrophage lineage marker F4_80 and CD172a expression (A—F4_80 positive and B—F4_80 negative subsets). Each point in the viSNE map represents an individual cell and color represent the expression level of indicated markers from high (Red) to low (Blue). (FIG. 13D) DREVI plots in all panels represent the relationship between pc-Jun and pEgfr, pJnk, pCamkII, prS6, pc-Cbl, pFgfr, pMapkapk2, b-catenin, cyclinD1 and D2, p p38, pCreb, CyclinB, and Npm1.

DEFINITIONS

Figure 1A:
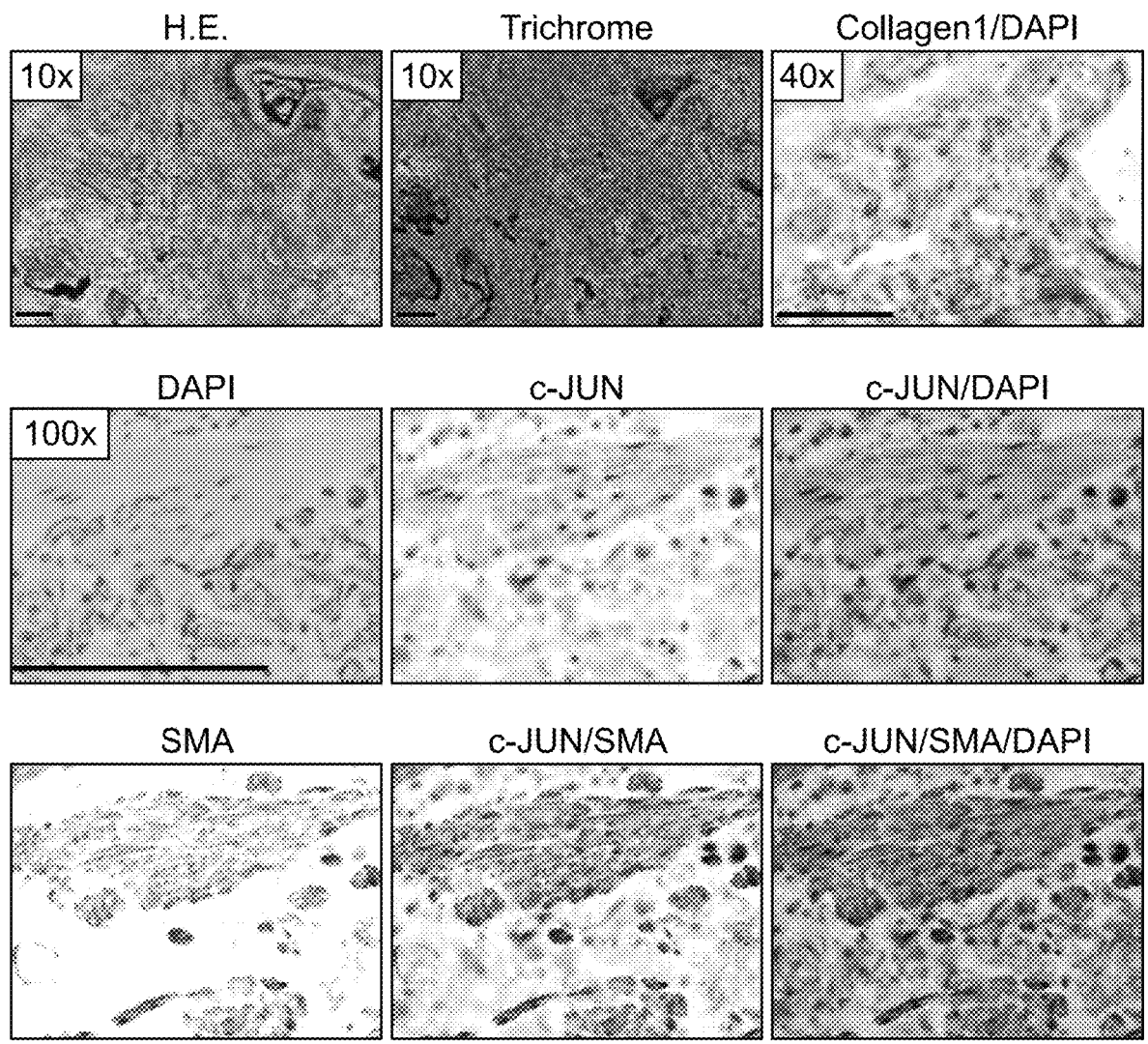
FIG. 1A-1E. Many fibrosing diseases demonstrated increased c-JUN expression in pathogenic fibroblasts.

It is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol No. I, Cold Spring Harbor Laboratory (1998); and Harlow and Lane, Antibodies: A Laboratory Manual, Cold Spring Harbor Laboratory; (1988).

Anti-CD47 agent. CD47 is a broadly expressed transmembrane glycoprotein with a single Ig-like domain and five membrane spanning regions, which functions as a cellular ligand for SIRPα with binding mediated through the NH2-terminal V-like domain of SIRPα. SIRPα is expressed primarily on myeloid cells, including macrophages, granulocytes, myeloid dendritic cells (DCs), mast cells, and their precursors, including hematopoietic stem cells. Structural determinants on SIRPα that mediate CD47 binding are discussed by Lee et al. (2007) J. Immunol. 179:7741-7750; Hatherley et al. (2008) Mol Cell. 31(2):266-77; Hatherley et al. (2007) J.B.C. 282:14567-75; and the role of SIRPα cis dimerization in CD47 binding is discussed by Lee et al. (2010) J.B.C. 285:37953-63. In keeping with the role of CD47 to inhibit phagocytosis of normal cells, there is evidence that it is transiently upregulated on hematopoietic stem cells (HSCs) and progenitors just prior to and during their migratory phase, and that the level of CD47 on these cells determines the probability that they are engulfed in vivo.

As used herein, the term "anti-CD47 agent" or "agent that provides for CD47 blockade" refers to any agent that reduces the binding of CD47 (e.g., on a target cell) to SIRPα (e.g., on a phagocytic cell). Non-limiting examples of suitable anti-CD47 reagents include SIRPα reagents, including without limitation high affinity SIRPα polypeptides, anti-SIRPα antibodies, soluble CD47 polypeptides, and anti-CD47 antibodies or antibody fragments. In some embodiments, a suitable anti-CD47 agent (e.g. an anti-CD47 antibody, a SIRPα reagent, etc.) specifically binds CD47 to reduce the binding of CD47 to SIRPα.

In some embodiments, a suitable anti-CD47 agent (e.g., an anti-SIRPα antibody, a soluble CD47 polypeptide, etc.) specifically binds SIRPα to reduce the binding of CD47 to SIRPα. A suitable anti-CD47 agent that binds SIRPα does not activate SIRPα (e.g., in the SIRPα-expressing phagocytic cell). The efficacy of a suitable anti-CD47 agent can be assessed by assaying the agent. In an exemplary assay, target cells are incubated in the presence or absence of the candidate agent and in the presence of an effector cell, e.g. a macrophage or other phagocytic cell. An agent for use in the methods of the invention will up-regulate phagocytosis by at least 5% (e.g., at least 10%, at least 20%, at least 30%, at least 40%, at least 50%, at least 60%, at least 70%, at least 80%, at least 90%, at least 100%, at least 120%, at least 140%, at least 160%, at least 180%, at least 200%, at least 500%, at least 1000%) compared to phagocytosis in the absence of the agent. Similarly, an in vitro assay for levels of tyrosine phosphorylation of SIRPα will show a decrease in phosphorylation by at least 5% (e.g., at least 10%, at least 15%, at least 20%, at least 30%, at least 40%, at least 50%, at least 60%, at least 70%, at least 80%, at least 90%, or 100%) compared to phosphorylation observed in absence of the candidate agent.

In some embodiments, the anti-CD47 agent does not activate CD47 upon binding. When CD47 is activated, a process akin to apoptosis (i.e., programmed cell death) may occur (Manna and Frazier, Cancer Research, 64, 1026-1036, Feb. 1, 2004). Thus, in some embodiments, the anti-CD47 agent does not directly induce cell death of a CD47-expressing cell.

In some embodiments a primer agent is administered prior to administering a therapeutically effective dose of an anti-CD47 agent to the individual. Suitable primer agents include an erythropoiesis-stimulating agent (ESA), and/or a priming dose of an anti-CD47 agent. Following administration of the priming agent, and allowing a period of time effective for an increase in reticulocyte production, a therapeutic dose of an anti-CD47 agent is administered. Administration may be made in accordance with the methods described in co-pending patent application U.S. Ser. No. 14/769,069, herein specifically incorporated by reference.

SIRPα reagent. A SIRPα reagent comprises the portion of SIRPα that is sufficient to bind CD47 at a recognizable affinity, which normally lies between the signal sequence and the transmembrane domain, or a fragment thereof that retains the binding activity. A suitable SIRPα reagent reduces (e.g., blocks, prevents, etc.) the interaction between the native proteins SIRPα and CD47. The SIRPα reagent will usually comprise at least the d1 domain of SIRPα.

In some embodiments, a subject anti-CD47 agent is a "high affinity SIRPα reagent", which includes SIRPα-derived polypeptides and analogs thereof (e.g., CV1-hIgG4, and CV1 monomer). High affinity SIRPα reagents are described in international application PCT/US13/21937, which is hereby specifically incorporated by reference. High affinity SIRPα reagents are variants of the native SIRPα protein. The amino acid changes that provide for increased affinity are localized in the d1 domain, and thus high affinity SIRPα reagents comprise a d1 domain of human SIRPα, with at least one amino acid change relative to the wild-type sequence within the d1 domain. Such a high affinity SIRPα reagent optionally comprises additional amino acid sequences, for example antibody Fc sequences; portions of the wild-type human SIRPα protein other than the d1 domain, including without limitation residues 150 to 374 of the native protein or fragments thereof, usually fragments contiguous with the d1 domain; and the like. High affinity SIRPα reagents may be monomeric or multimeric, i.e. dimer, trimer, tetramer, etc. In some embodiments, a high affinity SIRPα reagent is soluble, where the polypeptide lacks the SIRPα transmembrane domain and comprises at least one amino acid change relative to the wild-type SIRPα sequence, and wherein the amino acid change increases the affinity of the SIRPα polypeptide binding to CD47, for example by decreasing the off-rate by at least 10-fold, at least 20-fold, at least 50-fold, at least 100-fold, at least 500-fold, or more.

Optionally the SIRPα reagent is a fusion protein, e.g., fused in frame with a second polypeptide. In some embodiments, the second polypeptide is capable of increasing the size of the fusion protein, e.g., so that the fusion protein will not be cleared from the circulation rapidly. In some embodiments, the second polypeptide is part or whole of an immunoglobulin Fc region. The Fc region aids in phagocytosis by providing an "eat me" signal, which enhances the block of the "don't eat me" signal provided by the high affinity SIRPα reagent. In other embodiments, the second polypeptide is any suitable polypeptide that is substantially similar to Fc, e.g., providing increased size, multimerization domains, and/or additional binding or interaction with Ig molecules.

Anti-CD47 antibodies. In some embodiments, a subject anti-CD47 agent is an antibody that specifically binds CD47 (i.e., an anti-CD47 antibody) and reduces the interaction between CD47 on one cell (e.g., an infected cell) and SIRPα on another cell (e.g., a phagocytic cell). In some embodiments, a suitable anti-CD47 antibody does not activate CD47 upon binding. Some anti-CD47 antibodies do not reduce the binding of CD47 to SIRPα (and are therefore not considered to be an "anti-CD47 agent" herein) and such an antibody can be referred to as a "non-blocking anti-CD47 antibody." A suitable anti-CD47 antibody that is an "anti-CD47 agent" can be referred to as a "CD47-blocking antibody". Non-limiting examples of suitable antibodies include clones B6H12, 5F9, 8B6, and C3 (for example as described in International Patent Publication WO 2011/143624, herein specifically incorporated by reference). Suitable anti-CD47 antibodies include fully human, humanized or chimeric versions of such antibodies. Humanized antibodies (e.g., hu5F9-G4) are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

In some embodiments an anti-CD47 antibody comprises a human IgG Fc region, e.g. an IgG1, IgG2a, IgG2b, IgG3, IgG4 constant region. In a preferred embodiment the IgG Fc region is an IgG4 constant region. The IgG4 hinge may be stabilized by the amino acid substitution S241P (see Angal et al. (1993) Mol. Immunol. 30(1):105-108, herein specifically incorporated by reference).

Anti-SIRPα antibodies. In some embodiments, a subject anti-CD47 agent is an antibody that specifically binds SIRPα (i.e., an anti-SIRPα antibody) and reduces the interaction between CD47 on one cell (e.g., an infected cell) and SIRPα on another cell (e.g., a phagocytic cell). Suitable anti-SIRPα antibodies can bind SIRPα without activating or stimulating signaling through SIRPα because activation of SIRPα would inhibit phagocytosis. Instead, suitable anti-SIRPα antibodies facilitate the preferential phagocytosis of inflicted cells over normal cells. Those cells that express higher levels of CD47 (e.g., infected cells) relative to other cells (non-infected cells) will be preferentially phagocytosed. Thus, a suitable anti-SIRPα antibody specifically binds SIRPα (without activating/stimulating enough of a signaling response to inhibit phagocytosis) and blocks an interaction between SIRPα and CD47. Suitable anti-SIRPα antibodies include fully human, humanized or chimeric versions of such antibodies. Humanized antibodies are especially useful for in vivo applications in humans due to their low antigenicity. Similarly caninized, felinized, etc. antibodies are especially useful for applications in dogs, cats, and other species respectively. Antibodies of interest include humanized antibodies, or caninized, felinized, equinized, bovinized, porcinized, etc., antibodies, and variants thereof.

Soluble CD47 polypeptides. In some embodiments, a subject anti-CD47 agent is a soluble CD47 polypeptide that specifically binds SIRPα and reduces the interaction between CD47 on one cell (e.g., an infected cell) and SIRPα on another cell (e.g., a phagocytic cell). A suitable soluble CD47 polypeptide can bind SIRPα without activating or stimulating signaling through SIRPα because activation of SIRPα would inhibit phagocytosis. Instead, suitable soluble CD47 polypeptides facilitate the preferential phagocytosis of infected cells over non-infected cells. Those cells that express higher levels of CD47 (e.g., infected cells) relative to normal, non-target cells (normal cells) will be preferentially phagocytosed. Thus, a suitable soluble CD47 polypeptide specifically binds SIRPα without activating/stimulating enough of a signaling response to inhibit phagocytosis.

In some cases, a suitable soluble CD47 polypeptide can be a fusion protein (for example as structurally described in US Patent Publication US20100239579, herein specifically incorporated by reference). However, only fusion proteins that do not activate/stimulate SIRPα are suitable for the methods provided herein. Suitable soluble CD47 polypeptides also include any peptide or peptide fragment comprising variant or naturally existing CD47 sequences (e.g., extracellular domain sequences or extracellular domain variants) that can specifically bind SIRPα and inhibit the interaction between CD47 and SIRPα without stimulating enough SIRPα activity to inhibit phagocytosis.

In certain embodiments, soluble CD47 polypeptide comprises the extracellular domain of CD47, including the signal peptide, such that the extracellular portion of CD47 is typically 142 amino acids in length. The soluble CD47 polypeptides described herein also include CD47 extracellular domain variants that comprise an amino acid sequence at least 65%-75%, 75%-80%, 80-85%, 85%-90%, or 95%-99% (or any percent identity not specifically enumerated between 65% to 100%), which variants retain the capability to bind to SIRPα without stimulating SIRPα signaling.

In certain embodiments, the signal peptide amino acid sequence may be substituted with a signal peptide amino acid sequence that is derived from another polypeptide (e.g., for example, an immunoglobulin or CTLA4). For example, unlike full-length CD47, which is a cell surface polypeptide that traverses the outer cell membrane, the soluble CD47 polypeptides are secreted; accordingly, a polynucleotide encoding a soluble CD47 polypeptide may include a nucleotide sequence encoding a signal peptide that is associated with a polypeptide that is normally secreted from a cell.

In other embodiments, the soluble CD47 polypeptide comprises an extracellular domain of CD47 that lacks the signal peptide. As described herein, signal peptides are not exposed on the cell surface of a secreted or transmembrane protein because either the signal peptide is cleaved during translocation of the protein or the signal peptide remains anchored in the outer cell membrane (such a peptide is also called a signal anchor). The signal peptide sequence of CD47 is believed to be cleaved from the precursor CD47 polypeptide in vivo.

In other embodiments, a soluble CD47 polypeptide comprises a CD47 extracellular domain variant. Such a soluble CD47 polypeptide retains the capability to bind to SIRPα without stimulating SIRPα signaling. The CD47 extracellular domain variant may have an amino acid sequence that is at least 65%-75%, 75%-80%, 80-85%, 85%-90%, or 95%-99% identical (which includes any percent identity between any one of the described ranges) to the native CD47 sequence.

Anti-c-Jun agent. c-Jun is a protein that combines with c-Fos to form the AP-1 early response transcription factor, which functions in regulating gene expression for differentiation, cell cycle progression, proliferation, apoptosis, and other cellular processes. There is evidence that c-Jun is up-regulated and activated in the mesenchymal cell compartment of multiple fibrotic conditions, and can functionally contribute to the fibrogenic process.

As used herein, the term "anti-c-Jun agent" or "agent that provides for c-Jun blockade" refers to any agent that inhibits c-Jun pathways or reduces the expression of c-Jun within a target cell. Non-limiting examples of suitable anti-c-Jun reagents include anti-sense or RNAi agents that inhibit expression of c-Jun, small molecule inhibitors of c-Jun, and the like. Some embodiments of the invention further comprise concurrent administration with an anti-CD47 agent.

In some embodiments, an anti-c-Jun agent functions by inhibiting or reducing the expression of PI3K pathways. Non-limiting examples of suitable anti-PI3K reagents include polypeptides, antibodies that bind to PI3K, antisense or RNAi agents that inhibit expression of PI3K, small molecule inhibitors of PI3K, and the like. Specific examples of anti-PI3K agents applicable to the methods of the invention include, but are not limited to, Wortmannin, F-1126, BEZ-235, BKM120, BYL719, XL-147, GDC-0941, BGT226, GSK1059615, GSK690693, XL-765, PX866, GDC0941, CAL101, Perifosine, VQD002, MK2206, and combinations thereof.

In some embodiments, an anti-c-Jun agent functions by inhibiting or reducing the expression of VEGF pathways. Non-limiting examples of suitable anti-VEGF reagents include polypeptides, antibodies that bind to VEGF, small molecule inhibitors of VEGF, and the like. Specific examples of anti-VEGF agents applicable to the methods of the invention include, but are not limited to, pazopanib, bevacizumab, sorafenib, sunitinib, axitinib, and combinations thereof.

The anti-c-Jun agent may be an antisense oligonucleotide (ODN), particularly synthetic ODN having chemical modifications from native nucleic acids, or nucleic acid constructs that express such antisense molecules as RNA. The antisense sequence is complementary to the targeted RNA, and inhibits its expression. One or a combination of antisense molecules may be administered, where a combination may comprise multiple different sequences.

Antisense molecules may be produced by expression of all or a part of the target RNA sequence in an appropriate vector, where the transcriptional initiation is oriented such that an antisense strand is produced as an RNA molecule. Alternatively, the antisense molecule is a synthetic oligonucleotide. Antisense oligonucleotides will generally be at least about 7, usually at least about 12, more usually at least about 20 nucleotides in length, and not more than about 25, usually not more than about 23-22 nucleotides in length, where the length is governed by efficiency of inhibition, specificity, including absence of cross-reactivity, and the like.

Antisense oligonucleotides may be chemically synthesized by methods known in the art (see Wagner et al. (1993) supra. and Milligan et al., supra.) Preferred oligonucleotides are chemically modified from the native phosphodiester structure, in order to increase their intracellular stability and binding affinity. A number of such modifications have been described in the literature that alter the chemistry of the backbone, sugars or heterocyclic bases.

Among useful changes in the backbone chemistry are phosphorothioates; phosphorodithioates, where both of the non-bridging oxygens are substituted with sulfur; phosphoroamidites; alkyl phosphotriesters and boranophosphates. Achiral phosphate derivatives include 3'-O'-5'-S-phosphorothioate, 3'-S-5'-O-phosphorothioate, 3'-CH2-5'-O-phosphonate and 3'-NH-5'-O-phosphoroamidate. Peptide nucleic acids replace the entire ribose phosphodiester backbone with a peptide linkage. Sugar modifications are also used to enhance stability and affinity. The alpha-anomer of deoxyribose may be used, where the base is inverted with respect to the natural beta-anomer. The 2'-OH of the ribose sugar may be altered to form 2'-O-methyl or 2'-O-allyl sugars, which provides resistance to degradation without comprising affinity. Modification of the heterocyclic bases must maintain proper base pairing. Some useful substitutions include deoxyuridine for deoxythymidine; 5-methyl-2'-deoxycytidine and 5-bromo-2'-deoxycytidine for deoxycytidine. 5-propynyl-2'-deoxyuridine and 5-propynyl-2'-deoxycytidine have been shown to increase affinity and biological activity when substituted for deoxythymidine and deoxycytidine, respectively.

Anti-sense molecules of interest include antagomir RNAs, e.g. as described by Krutzfeldt et al., supra., herein specifically incorporated by reference. Small interfering double-stranded RNAs (siRNAs) engineered with certain 'drug-like' properties such as chemical modifications for stability and cholesterol conjugation for delivery have been shown to achieve therapeutic silencing of an endogenous gene in vivo. To develop a pharmacological approach for silencing miRNAs in vivo, chemically modified, cholesterol-conjugated single-stranded RNA analogues complementary to miRNAs were developed, termed 'antagomirs'. Antagomir RNAs may be synthesized using standard solid phase oligonucleotide synthesis protocols. The RNAs are conjugated to cholesterol, and may further have a phosphorothioate backbone at one or more positions.

Also of interest in certain embodiments are RNAi agents. In representative embodiments, the RNAi agent targets the precursor molecule of the c-Jun RNA. By RNAi agent is meant an agent that modulates expression by a RNA interference mechanism. The RNAi agents employed in one embodiment of the subject invention are small ribonucleic acid molecules (also referred to herein as interfering ribonucleic acids), i.e., oligoribonucleotides, that are present in duplex structures, e.g., two distinct oligoribonucleotides hybridized to each other or a single ribooligonucleotide that assumes a small hairpin formation to produce a duplex structure. By oligoribonucleotide is meant a ribonucleic acid that does not exceed about 100 nt in length, and typically does not exceed about 75 nt length, where the length in certain embodiments is less than about 70 nt. Where the RNA agent is a duplex structure of two distinct ribonucleic acids hybridized to each other, e.g., an siRNA, the length of the duplex structure typically ranges from about 15 to 30 bp, usually from about 15 to 29 bp, where lengths between about 20 and 29 bps, e.g., 21 bp, 22 bp, are of particular interest in certain embodiments. Where the RNA agent is a duplex structure of a single ribonucleic acid that is present in a hairpin formation, i.e., a shRNA, the length of the hybridized portion of the hairpin is typically the same as that provided above for the siRNA type of agent or longer by 4-8 nucleotides. The weight of the RNAi agents of this embodiment typically ranges from about 5,000 daltons to about 35,000 daltons, and in many embodiments is at least about 10,000 daltons and less than about 27,500 daltons, often less than about 25,000 daltons.

dsRNA can be prepared according to any of a number of methods that are known in the art, including in vitro and in vivo methods, as well as by synthetic chemistry approaches. Examples of such methods include, but are not limited to, the methods described by Sadher et al. (Biochem. Int. 14:1015, 1987); by Bhattacharyya (Nature 343:484, 1990); and by Livache, et al. (U.S. Pat. No. 5,795,715), each of which is incorporated herein by reference in its entirety.

Single-stranded RNA can also be produced using a combination of enzymatic and organic synthesis or by total organic synthesis. The use of synthetic chemical methods enable one to introduce desired modified nucleotides or nucleotide analogs into the dsRNA. dsRNA can also be prepared in vivo according to a number of established methods (see, e.g., Sambrook, et al. (1989) Molecular Cloning: A Laboratory Manual, 2nd ed.; Transcription and Translation (B. D. Hames, and S. J. Higgins, Eds., 1984); DNA Cloning, volumes I and II (D. N. Glover, Ed., 1985); and Oligonucleotide Synthesis (M. J. Gait, Ed., 1984, each of which is incorporated herein by reference in its entirety).

In certain embodiments, instead of the RNAi agent being an interfering ribonucleic acid, e.g., an siRNA or shRNA as described above, the RNAi agent may encode an interfering ribonucleic acid, e.g., an shRNA, as described above. In other words, the RNAi agent may be a transcriptional template of the interfering ribonucleic acid. In these embodiments, the transcriptional template is typically a DNA that encodes the interfering ribonucleic acid. The DNA may be present in a vector, where a variety of different vectors are known in the art, e.g., a plasmid vector, a viral vector, etc.

The terms "subject," "individual," and "patient" are used interchangeably herein to refer to a mammal being assessed for treatment and/or being treated. In an embodiment, the mammal is a human. The terms "subject," "individual," and "patient" thus encompass individuals having fibrosis, including without limitation, tumor fibrosis, cardiac fibrosis, liver fibrosis, kidney fibrosis, lung fibrosis, dermal scarring and keloids, Alzheimer's disease, etc. Subjects may be human, but also include other mammals, particularly those mammals useful as laboratory models for human disease, e.g. mouse, rat, etc.

The definition of an appropriate patient sample encompasses blood and other liquid samples of biological origin, solid tissue samples such as a biopsy specimen or tissue cultures or cells derived there from and the progeny thereof. The definition also includes samples that have been manipulated in any way after their procurement, such as by treatment with reagents; washed; or enrichment for certain cell populations, such as endometrial cells, kidney disease cells, inflammatory disease cells and/or transplant rejection (GVHD) cells. The definition also includes sample that have been enriched for particular types of molecules, e.g., nucleic acids, polypeptides, etc. The term "biological sample" encompasses a clinical sample, and also includes tissue obtained by surgical resection, tissue obtained by biopsy, cells in culture, cell supernatants, cell lysates, tissue samples, organs, bone marrow, blood, plasma, serum, and the like. A "biological sample" includes a sample obtained from a patient's sample cell, e.g., a sample comprising polynucleotides and/or polypeptides that is obtained from a patient's sample cell (e.g., a cell lysate or other cell extract comprising polynucleotides and/or polypeptides); and a sample comprising sample cells from a patient. A biological sample comprising a sample cell from a patient can also include normal, non-diseased cells.

The term "diagnosis" is used herein to refer to the identification of a molecular or pathological state, disease or condition, such as the identification of fibrosis.

The methods of the invention may further comprise analysis of fibrosis or fibrotic activity following treatment according to the methods as claimed. Analysis of fibrosis may be made by obtaining a biological sample and examining molecular or pathological state, disease or condition, and the like.

Fibrosis is the excessive accumulation of extracellular matrix components (ECM) in and around inflamed or damaged tissue, often associated with chronic inflammation or cancer. The presence of fibrosis can be detected by means known in the art, for example by examination of tissue for excess scarring. Prior to fibrosis, an individual may be determined to be susceptible based on undesirable increase in inflammatory mediators that can exacerbate tissue injury, such as IL-1, TNF-α and reactive oxygen and nitrogen species. Profibrotic mediators such as TGF-β1 may be present. Also present are activated myofibroblasts, which may be resistant to induction of apoptosis.

Exemplary forms of fibrosis include, but are not limited to, tumor fibrosis, cardiac fibrosis, liver fibrosis, kidney and bladder fibrosis, lung fibrosis, dermal scarring and keloids, wound healing and adhesions, post-irradiation fibrosis, fibrosis related to chronic graft v host disease (GvHD), and Alzheimer's disease. In still further embodiments, cardiac fibrosis is associated with hypertension, hypertensive heart disease (HHD), myocardial infarction (MI), cardiac scarring related to ischemia congestive heart failure, cardiomyopathy, post-myocardial infarction defects in heart function, atherosclerosis, and restenosis. Kidney fibrosis may include, but not be limited to, diabetic nephropathy, vesicoureteral reflux, tubulointerstitial renal fibrosis, glomerulonephritis or glomerular nephritis (GN), focal segmental glomerulosclerosis, membranous glomerulonephritis, or mesangiocapillary GN. Liver fibrosis may include, but not be limited to, cirrhosis, and associated conditions such as chronic viral hepatitis, non-alcoholic fatty liver disease (NAFLD), alcoholic steatohepatitis (ASH), non-alcoholic steatohepatitis (NASH), primary biliary cirrhosis (PBC), biliary cirrhosis, autoimmune hepatitis). Lung fibrosis may include idiopathic pulmonary fibrosis (IPF) or cryptogenic fibrosing alveolitis, chronic fibrosing interstitial pneumonia, interstitial lung disease (ILD), and diffuse parenchymal lung disease (DPLD)), lung scarring including without limitation damage from bacterial viral or fungal infection, emphysema, chronic obstructive pulmonary disease (COPD); and chronic asthma may also be prevented, treated, or ameliorated with compositions of described herein. Also included is fibrosis of the eye and lens, for example glaucoma; age-related macular degeneration (wet AMD and dry AMD), fibrosis of the lens, periorbital fibrosis as in IgG4-related disease, hyperthyroidism, etc. Uterine fibroids are also if interest for treatment.

Renal fibrosis is the consequence of an excessive accumulation of extracellular matrix that occurs in virtually every type of chronic kidney disease. The pathogenesis of renal fibrosis is a progressive process that ultimately leads to end-stage renal failure, a devastating disorder that requires dialysis or kidney transplantation. In a simplistic view, renal fibrosis represents a failed wound-healing process of the kidney tissue after chronic, sustained injury. Several cellular pathways, including mesangial and fibroblast activation as well as tubular epithelial-mesenchymal transition, have been identified as the major avenues for the generation of the matrix-producing cells in diseased conditions.

Pulmonary fibrosis is characterized by lung inflammation and abnormal tissue repair, resulting in the replacement of normal functional tissue with an abnormal accumulation of fibroblasts and deposition of collagen in the lung. This process involves cellular interactions via a complex cytokine-signaling mechanism and heightened collagen gene expression, ultimately resulting in its abnormal collagen deposition in the lung. In addition to inflammatory cells, the fibroblast and signaling events that mediate fibroblast proliferation and myofibroblasts play important roles in the fibrotic process. However, the most potent anti-inflammatory drugs that have been widely used in the treatment of pulmonary fibrosis do not seem to interfere with the fibrotic disease progression.

Hepatic fibrosis is an accumulation in the liver of connective tissue in response to hepatocellular damage of nearly any cause. It results from excessive production or deficient degradation of the extracellular matrix. Fibrosis itself causes no symptoms but can lead to portal hypertension or cirrhosis. Liver fibrosis (also known as cirrhosis) is often a result of chronic liver disease and is characterized by replacement of liver tissue by fibrotic scar tissue and regenerative nodules which leads to loss of liver function. Cirrhosis can be caused by alcoholism, hepatitis B and C, and fatty liver disease, as well as other causes. Liver fibrosis is generally irreversible, and treatment usually focuses on preventing progression and managing complications. In advanced stages of liver fibrosis the only option is often a liver transplant.

Transplant rejection (graft-versus-host-disease; GVHD) is a common complication and often occurs after an allogeneic stem cell or bone marrow transplant from another person. Immune cells in the donated marrow or stem cells recognize the recipient as "foreign" and attack the recipient host's body. GVHD can also occur during a blood transfusion. Generally, the three Billingham Criteria are used for evaluating the occurrence of GVHD: an immuno-competent graft is administered that contains viable and functional immune cells; the recipient is immunologically disparate (histoincompatible); and the recipient is immuno-compromised and therefore cannot destroy or inactivate the transplanted cells.

Systemic sclerosis is a chronic disease of unknown cause characterized by diffuse fibrosis, degenerative changes, and vascular abnormalities in the skin, joints, and internal organs (especially the esophagus, lower GI tract, lung, heart, and kidney). Common symptoms include Raynaud's phenomenon, polyarthralgia, dysphagia, heartburn, and swelling and eventually skin tightening and contractures of the fingers. Lung, heart, and kidney involvement accounts for most deaths. Specific treatment is difficult, and emphasis is often on treatment of complications.

A variety of drugs have been tried in various fibroses, particularly lung fibrosis, with very little success. Anti-inflammatory drugs including prednisolone and azathioprine have little effect on fibrosis suggesting that inflammation is only the initiator, but not the driver of the disease. The use of non-specific anti-proliferatives like colchicine and cyclophosphamide will also prevent repair of the fibrotic tissue by impairing e.g. epithelial growth. Treatment with IFN-γ has shown some utility but is limited by severe side effects.

By the time a typical patient presents with fibrosis-related symptoms (e.g. difficulty breathing for lung fibrosis, cirrhosis for liver fibrosis, etc.), the fibrosis in the target organ is often quite severe, with much of the target organ architecture having been replaced with extracellular matrix. Stopping this ongoing fibrosis can extend lifespan and improve quality of life. Areas of the target organ where the fibrosis is not extensive may be restored to normal architecture with suitable treatment.

In some embodiments, tumor fibrosis is associated with pancreatic cancer. Pancreatic cancer is characterized by a prominent desmoplastic/stromal reaction. Pancreatic stellate cells (PSCs) are the principal source of fibrosis in the stroma and interact closely with cancer cells to create a tumor facilitatory environment that stimulates local tumor growth and distant metastasis. Pancreatic fibrosis is initiated when PSCs become activated and undergo morphological and functional changes, so that the rate of extracellular matrix (ECM) deposition exceeds the rate of ECM degradation in the gland. It is now well established that pancreatic cancer cells activate PSCs leading to increased fibrosis. There is significant evidence showing that the intense stromal/desmoplastic reaction around tumor elements (a feature of the majority of pancreatic cancers) plays an important role in tumor progression.

A key histopathological feature of pancreatic cancer which is associated with its innate clinical and biological aggressiveness is its desmoplastic (stromal) reaction. Stroma production is stimulated by cancer-cell derived growth factors including transforming growth factor-3 (TGFβ), hepatocyte growth factor (HGF), fibroblast growth factor (FGF), insulin-like growth factor 1 (IGF-1) and epidermal growth factor (EGF). The desmoplastic reaction is composed of extracellular matrix (ECM) proteins, primarily type I and III collagen, fibronectin and proteoglycans; small endothelium lined vessels; and a diverse population of cells including inflammatory cells, fibroblasts and stellate cells. The stroma can form up to 90% of the tumor volume, a property which is unique to pancreatic cancer. The tumor microenvironment in pancreatic cancer plays a role in its chemoresistance.

While stromal cells do not exhibit the genetic transformations seen in malignant pancreatic cancer cells, they are altered by cytokines and growth factors secreted by inflammatory cells and tumor cells. Reciprocally, the stromal cells promote tumor cell migration, growth, invasion and resistance to drugs and apoptosis. Staining pancreatic cancer tissue sections of patients for alpha smooth muscle actin (α-SMA the cytoskeletal protein marker for PSC activation) and collagen shows a high activated stroma index (α-SMA/collagen) correlated with a poor prognosis. The extensive ECM deposition by PSCs in pancreatic cancer causes distortion and compression of tumor vasculature by fibrous tissue which contributes to tumor hypoxia, a determinant of chemoresistance.

Non-alcoholic fatty liver disease (NAFLD) and non-alcoholic steatohepatitis (NASH) are conditions associated with fatty infiltration of the liver. NAFLD is one cause of a fatty liver, occurring when fat is deposited (steatosis) in the liver not due to excessive alcohol use (Clark J M et al, J. American Medical Association 289 (22): 3000-4, 2003). It can be related to insulin resistance and the metabolic syndrome and may respond to treatments originally developed for other insulin-resistant states (e.g. diabetes mellitus type 2) such as weight loss, metformin and thiazolidinediones.

NAFLD is considered to cover a spectrum of disease activity. This spectrum begins as fatty accumulation in the liver (hepatic steatosis). A liver can remain fatty without disturbing liver function, but by varying mechanisms and possible insults to the liver may also progress to become NASH, a state in which steatosis is combined with inflammation and fibrosis. NASH is a progressive disease: over a 10-year period, up to 20% of patients with NASH will develop cirrhosis of the liver, and 10% will suffer death related to liver disease. NASH is the most extreme form of NAFLD, and is regarded as a major cause of cirrhosis of the liver of unknown cause (McCulough A J et al, Clinics in Liver Disease 8 (3): 521-33, 2004).

Common findings in NAFLD and NASH are elevated liver enzymes and a liver ultrasound showing steatosis. An ultrasound may also be used to exclude gallstone problems (cholelithiasis). A liver biopsy (tissue examination) is the only test widely accepted as definitively distinguishing NASH from other forms of liver disease and can be used to assess the severity of the inflammation and resultant fibrosis (Adams et al, Postgrad Med J 82(967):315-22, 2006). Non-invasive diagnostic tests have been developed, such as FibroTest, that estimates liver fibrosis, and SteatoTest (McCulough A J et al, Clinics in Liver Disease 8 (3): 521-33, 2004). Fatty infiltration accompanied by an inflammatory reaction can lead to fibrosis and liver cirrhosis and ultimately hepatic failure. The inflammation in NASH is characterized by infiltration of the liver by macrophages and lymphocytes, as well as alterations in the liver's macrophage-like Kupfer cell population (Tilg, et al, 2010. Hepatology. 52(5):1836-46). There are no currently approved drug treatments for NASH. Results have not been consistent, with many studies ultimately failing to show an ultimate change in fibrosis (Schwenger K J P, World J Gastroenterol. Feb. 21, 2014; 20(7): 1712-1723).

Pre-clinical NASH or "at risk" for NASH can be defined as NAFLD, which is the presence of fatty infiltration of the liver on ultrasound (an abnormal imaging marker) in the absence of alcohol consumption or exposure to other liver toxins. The abnormal imaging marker of fatty infiltration of the liver is assessed by ultrasound imaging of the liver, and determination that an individual patient exhibits ultrasound results consistent with fatty infiltration of the liver which are outside of the range of ultrasound findings in 95% of normal humans. Humans with NAFLD and who have pre-clinical NASH (i.e., NAFLD) may have normal levels of liver enzymes in their blood (e.g. normal aminotransferase [transaminase] levels, including a normal AST (SGOT) and ALT (SGPT)).

Early-stage NASH is defined as the presence of NAFLD in conjunction with hepatic inflammation and injury, as reflected by abnormally high levels of blood aminotransferases (i.e., elevated levels of AST (SGOT) and ALT (SGPT) as compared to the normal range in humans—which represent abnormal markers of inflammation for NASH).

Advanced NASH is defined as the presence of chronic liver inflammation and injury, as reflected by persistently elevated levels of liver transaminases (persistently elevated AST (SGOT) and ALT (SGPT)), and the presence of early or advanced hepatic fibrosis and/or cirrhosis. Hepatic fibrosis is identified by ultrasound or CT or MRI imaging of the liver, or by liver biopsy.

In one embodiment, measurement of one or more abnormal metabolic markers, abnormal inflammatory markers, abnormal imaging markers, c-JUN induction, etc. are used to identify individuals at increased risk for subsequent development of NAFLD or NASH. Such individuals may be treated with an effective dose of an agent that inhibits the interaction between CD47 and SIRPα. For example, individuals with elevated liver transaminases, based on AST>60 IL/L (normal range 6-40 IU/L) or ALT>50 IU/L (normal range 7-35 IU/L), ultrasound findings indicative of fatty liver, and a fasting blood glucose>126 on two separate readings, or hemoglobin A1c>6.5%, are identified as exhibiting abnormal inflammatory markers, abnormal imaging markers or abnormal metabolic markers and therefore being at high risk for progression to NASH. In other embodiments, individuals with overt disease may also be treated with an effective dose of an agent that inhibits the interaction between CD47 and SIRPα. Such treatment methods can reduce fatty infiltration of the liver, and resulting fibrosis.

As used herein, the terms "treatment," "treating," and the like, refer to administering an agent, or carrying out a procedure for the purposes of obtaining an effect. The effect may be prophylactic in terms of completely or partially preventing a disease or symptom thereof and/or may be therapeutic in terms of effecting a partial or complete cure for a disease and/or symptoms of the disease. "Treatment," as used herein, covers any treatment of fibrosis in a mammal, particularly in a human, and includes: (a) preventing the development of fibrosis; (b) inhibiting ongoing fibrosis, i.e., arresting its development; and (c) relieving fibrosis, i.e., causing regression of fibrosis.

Treating may refer to any indicia of success in the treatment or amelioration or prevention of fibrosis, including any objective or subjective parameter such as abatement; remission; diminishing of symptoms or making the disease condition more tolerable to the patient; slowing in the rate of degeneration or decline; or making the final point of degeneration less debilitating. The treatment or amelioration of symptoms can be based on objective or subjective parameters; including the results of an examination by a physician. Accordingly, the term "treating" includes the administration of the compounds or agents of the present invention to prevent or delay, to alleviate, or to arrest or inhibit development of the symptoms or conditions associated with fibrosis. The term "therapeutic effect" refers to the reduction, elimination, or prevention of the disease, symptoms of the disease, or side effects of the disease in the subject.

"In combination with", "combination therapy" and "combination products" refer, in certain embodiments, to the concurrent administration to a patient of a first therapeutic (i.e., first therapeutic agent) and the compounds as used herein. When administered in combination, each component can be administered at the same time or sequentially in any order at different points in time. Thus, each component can be administered separately but sufficiently closely in time so as to provide the desired therapeutic effect. First therapeutic agents contemplated for use with the methods of the present invention include any other agent for use in the treatment of fibrosis. Examples of such therapeutic agents include but are not limited anti-fibrotic agents.

"Concomitant administration" of a known therapeutic agent with a pharmaceutical composition of the present invention means administration of the therapeutic agent and inhibitor agent at such time that both the known therapeutic agent and the composition of the present invention will have a therapeutic effect. Such concomitant administration may involve concurrent (i.e. at the same time), prior, or subsequent administration of the drug with respect to the administration of a compound of the present invention. A person of ordinary skill in the art would have no difficulty determining the appropriate timing, sequence and dosages of administration for particular drugs and compositions of the present invention. Therapeutic agents contemplated for concomitant administration according to the methods of the present invention include any other agent for use in the treatment of fibrosis.

As used herein, the term "correlates," or "correlates with," and like terms, refers to a statistical association between instances of two events, where events include numbers, data sets, and the like. For example, when the events involve numbers, a positive correlation (also referred to herein as a "direct correlation") means that as one increases, the other increases as well. A negative correlation (also referred to herein as an "inverse correlation") means that as one increases, the other decreases.

"Dosage unit" refers to physically discrete units suited as unitary dosages for the particular individual to be treated. Each unit can contain a predetermined quantity of active compound(s) calculated to produce the desired therapeutic effect(s) in association with the required pharmaceutical carrier. The specification for the dosage unit forms can be dictated by (a) the unique characteristics of the active compound(s) and the particular therapeutic effect(s) to be achieved, and (b) the limitations inherent in the art of compounding such active compound(s).

"Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients can be solid, liquid, semisolid, or, in the case of an aerosol composition, gaseous.

The terms "pharmaceutically acceptable", "physiologically tolerable" and grammatical variations thereof, as they refer to compositions, carriers, diluents and reagents, are used interchangeably and represent that the materials are capable of administration to or upon a human without the production of undesirable physiological effects to a degree that would prohibit administration of the composition.

A "therapeutically effective amount" means the amount that, when administered to a subject for treating a disease, is sufficient to effect treatment for that disease.

The phrase "determining the treatment efficacy" and variants thereof can include any methods for determining that a treatment is providing a benefit to a subject. The term "treatment efficacy" and variants thereof are generally indicated by alleviation of one or more signs or symptoms associated with the disease and can be readily determined by one skilled in the art. "Treatment efficacy" may also refer to the prevention or amelioration of signs and symptoms of toxicities typically associated with standard or non-standard treatments of a disease. Determination of treatment efficacy is usually indication and disease specific and can include any methods known or available in the art for determining that a treatment is providing a beneficial effect to a patient. For example, evidence of treatment efficacy can include but is not limited to remission of the disease or indication. Further, treatment efficacy can also include general improvements in the overall health of the subject, such as but not limited to enhancement of patient life quality, increase in predicted subject survival rate, decrease in depression or decrease in rate of recurrence of the indication (increase in remission time). (See, e.g., *Physicians' Desk Reference* (2010).)

DETAILED DESCRIPTION OF THE EMBODIMENTS

Individuals diagnosed or at risk of developing a fibrotic disease, including fatty liver disease, are treated by administering one or both of (i) an agent that inhibits CD47 and SIRPα pathways; and (ii) an agent that inhibits c-JUN. In some embodiments the fibrosis is a pulmonary fibrosis, such as idiopathic pulmonary fibrosis. In some embodiments the fibrosis is associated with cancer and tumor growth, i.e. tumor related tissue fibrosis, including without limitation pancreatic cancer. In other embodiments the fibrosis is associated with chronic inflammation or injury such as irradiation in tissues, including without limitation fibrosis of liver, lung, kidney, uterus, the eye and the lens, IgG4-related disease, chronic GvHD, and the like.

In some embodiments, a fibrotic disease is selected for treatment with a combination therapy where the combination comprises an inhibitor of CD47 pathways, and an inhibitor of c-Jun.

Methods include administering to a subject in need of treatment a therapeutically effective amount or an effective dose of a therapeutic entity (e.g., inhibitor agent) of CD47 or c-JUN. In some embodiments, effective doses of the therapeutic entity of the present invention described herein vary depending upon many different factors, including means of administration, target site, physiological state of the patient, whether the patient is human or an animal, other medications administered, and whether treatment is prophylactic or therapeutic. Usually, the patient is a human but nonhuman mammals including transgenic mammals can also be treated. Treatment dosages need to be titrated to optimize safety and efficacy. Reduction in fibrosis may be monitored for decrease in fibrotic cells, decrease in fatty infiltrating cells, etc.

In some embodiments CD47 blockade is accomplished by administering a soluble SIRPα polypeptide, which may be a high affinity SIRPα variant polypeptide. In other embodiments, antibodies specific for one or both of SIRPα and CD47 are administered.

The effective dose of an anti-CD47 agent can vary with the agent, but will generally range from up to about 50 mg/kg, up to about 40 mg/kg, up to about 30 mg/kg, up to about 20 mg/kg, up to about 10 mg/kg, up to about 5 mg/kg; up to about 1 mg/kg, up to about 0.5 mg/kg; up to about 0.1 mg/kg; up to about 0.05 mg/kg; where the dose may vary with the specific antibody and recipient. Agents that bind to CD47, e.g. soluble SIRPα polypeptides and anti-CD47 antibodies, may be administered at higher doses due to the larger number of CD47 expressing cells in the body.

The anti-CD47 agent may be administered one or a plurality of days, and in some embodiments is administered daily, every two days, semi-weekly, weekly, etc. for a period of from about 1, about 2, about 3, about 4, about 5, about 6, about 7 or more weeks, up to a chronic maintenance level of dosing. See, for example, U.S. Pat. No. 9,623,079, herein specifically incorporated by reference for teaching dosage regimens.

In other embodiments, the dosage, for example of a c-JUN inhibitor, may range from about 0.0001 to 100 mg/kg, and more usually 0.01 to 5 mg/kg, of the host body weight. For example dosages can be 1 mg/kg body weight or 10 mg/kg body weight or within the range of 1-10 mg/kg. An exemplary treatment regime entails administration once per every two weeks or once a month or once every 3 to 6 months. Therapeutic entities of the present invention are usually administered on multiple occasions. Intervals between single dosages can be weekly, monthly or yearly. Intervals can also be irregular as indicated by measuring blood levels of the therapeutic entity in the patient. Alternatively, therapeutic entities of the present invention can be administered as a sustained release formulation, in which case less frequent administration is required. Dosage and frequency vary depending on the half-life of the polypeptide in the patient.

In prophylactic applications, a relatively low dosage is administered at relatively infrequent intervals over a long period of time. Some patients continue to receive treatment for the rest of their lives. In therapeutic applications, a relatively high dosage at relatively short intervals is sometimes required until progression of the disease is reduced or terminated, and preferably until the patient shows partial or complete amelioration of symptoms of disease. Thereafter, the patent can be administered a prophylactic regime.

In still yet some other embodiments, for prophylactic applications, pharmaceutical compositions or medicaments are administered to a patient susceptible to, or otherwise at risk of a disease or condition in an amount sufficient to eliminate or reduce the risk, lessen the severity, or delay the outset of the disease, including biochemical, histologic and/or behavioral symptoms of the disease, its complications and intermediate pathological phenotypes presenting during development of the disease.

In still yet some other embodiments, for therapeutic applications, therapeutic entities of the present invention are administered to a patient suspected of, or already suffering from such a disease in an amount sufficient to cure, or at least partially arrest, the symptoms of the disease (biochemical, histologic and/or behavioral), including its complications and intermediate pathological phenotypes in development of the disease. An amount adequate to accomplish therapeutic or prophylactic treatment is defined as a therapeutically- or prophylactically-effective dose. In both prophylactic and therapeutic regimes, agents are usually administered in several dosages until a sufficient response has been achieved.

According to the present invention, compositions can be administered by parenteral, topical, intravenous, oral, subcutaneous, intraarterial, intracranial, intraperitoneal, intranasal or intramuscular means. The most typical route of administration is intravenous although other routes can be equally effective.

For parenteral administration, compositions of the invention can be administered as injectable dosages of a solution or suspension of the substance in a physiologically acceptable diluent with a pharmaceutical carrier that can be a sterile liquid such as water, oils, saline, glycerol, or ethanol. Additionally, auxiliary substances, such as wetting or emulsifying agents, surfactants, pH buffering substances and the like can be present in compositions. Other components of pharmaceutical compositions are those of petroleum, animal, vegetable, or synthetic origin, for example, peanut oil, soybean oil, and mineral oil. In general, glycols such as propylene glycol or polyethylene glycol are preferred liquid carriers, particularly for injectable solutions. Antibodies and/or polypeptides can be administered in the form of a depot injection or implant preparation which can be formulated in such a manner as to permit a sustained release of the active ingredient. An exemplary composition comprises polypeptide at 1 mg/mL, formulated in aqueous buffer consisting of 10 mM Tris, 210 mM sucrose, 51 mM L-arginine, 0.01% polysorbate 20, adjusted to pH 7.4 with HCl or NaOH.

Typically, compositions are prepared as injectables, either as liquid solutions or suspensions; solid forms suitable for solution in, or suspension in, liquid vehicles prior to injection can also be prepared. The preparation also can be emulsified or encapsulated in liposomes or micro particles such as polylactide, polyglycolide, or copolymer for enhanced adjuvant effect, as discussed above. Langer, Science 249: 1527, 1990 and Hanes, Advanced Drug Delivery Reviews 28: 97-119, 1997. The agents of this invention can be administered in the form of a depot injection or implant preparation which can be formulated in such a manner as to permit a sustained or pulsatile release of the active ingredient.

Additional formulations suitable for other modes of administration include oral, intranasal, and pulmonary formulations, suppositories, and transdermal applications.

For suppositories, binders and carriers include, for example, polyalkylene glycols or triglycerides; such suppositories can be formed from mixtures containing the active ingredient in the range of 0.5% to 10%, preferably 1%-2%. Oral formulations include excipients, such as pharmaceutical grades of mannitol, lactose, starch, magnesium stearate, sodium saccharine, cellulose, and magnesium carbonate. These compositions take the form of solutions, suspensions, tablets, pills, capsules, sustained release formulations or powders and contain 10%-95% of active ingredient, preferably 25%-70%.

Topical application can result in transdermal or intradermal delivery. Topical administration can be facilitated by co-administration of the agent with cholera toxin or detoxified derivatives or subunits thereof or other similar bacterial toxins. Glenn et al., Nature 391: 851, 1998. Co-administration can be achieved by using the components as a mixture or as linked molecules obtained by chemical crosslinking or expression as a fusion protein.

Alternatively, transdermal delivery can be achieved using a skin patch or using transferosomes. Paul et al., Eur. J. Immunol. 25: 3521-24, 1995; Cevc et al., Biochem. Biophys. Acta 1368: 201-15, 1998.

The pharmaceutical compositions are generally formulated as sterile, substantially isotonic and in full compliance with all Good Manufacturing Practice (GMP) regulations of the U.S. Food and Drug Administration. Preferably, a therapeutically effective dose will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage can vary within this range depending upon the dosage form employed and the route of administration utilized. The exact formulation, route of administration and dosage can be chosen by the individual physician in view of the patient's condition. (See, e.g., Fingl et al., 1975, In: The Pharmacological Basis of Therapeutics, Ch. 1).

Also within the scope of the invention are kits comprising the compositions of the invention and instructions for use. The kit can further contain a least one additional reagent. Kits typically include a label indicating the intended use of the contents of the kit. The term label includes any writing, or recorded material supplied on or with the kit, or which otherwise accompanies the kit.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible. It is also understood that the terminology used herein is for the purposes of describing particular embodiments Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or only and is not intended to limit the scope of the present invention which will be limited only by the appended claims.

Those skilled in the art will recognize, or be able to ascertain using no more than routine experimentation, many equivalents to the specific embodiments of the invention described herein. Such equivalents are intended to be encompassed by the appended claims.

EXPERIMENTAL

Example 1

A Unifying Mechanism for Different Fibrotic Diseases

The fibrogenic response is an important component of normal repair processes, which, if un-controlled, can lead to various life-threatening conditions like idiopathic pulmonary fibrosis, primary myelofibrosis and systemic sclerosis. While these diverse diseases share some histological hallmarks, it is not known whether similar molecular mechanisms are responsible for the fibrotic response among the different disease entities. In vitro studies suggested distinct pathogenic processes and the involvement of multiple signaling pathways and some studies came to conflicting conclusions. The molecular processes driving fibrogenesis are thought of as wide-ranging and complex involving transforming growth factor B (TGFB), platelet-derived growth factor (PDGF), connective-tissue growth factor (CTGF), vasoactive peptide, and integrin signaling. Also on the cellular level, most fibrosis syndromes are thought to be complex involving the cross talk of hematopoietic cells and mesenchymal stroma cells in an inflammatory or tumor environment.

The progress of understanding the pathogenesis of fibrosing diseases is largely limited by the substantial shortcomings of currently available animal models. E.g. the standard in vivo model for lung fibrosis is a chemical injury model based on bleomycin treatment and likely involves a completely different pathogenesis than the idiopathic human disease. A more recent genetic mouse model showed some fibrosis features but predominantly exhibits vaso-occlusive alterations more reminiscent of pulmonary artery hypertension (PAH).

On the other hand, the genetic basis of fibrosing diseases is just emerging but already promising to gain fundamental insights into pathomechanisms, e.g. FAN1 mutations were associated with kidney fibrosis, PNLAP3 with liver fibrosis, telomerase reverse transcriptase (TERT) and mucin 5B (MUC5B) with lung fibrosis, as well as alterations in DNA methylation, and some microRNAs have been shown to play a role in lung fibrosis. Some of these molecular findings have led to recent breakthroughs in the treatment of e.g. lung fibrosis and primary myelofibrosis.

We previously developed mouse models of primary myelofibrosis associated with myeloproliferative disease and wished to investigate their molecular downstream effectors. Gene expression analysis suggested the dysregulation of AP-1 family transcription factors which are well-established regulators of critical cell biological processes and involved in cancer and other human disease conditions. This led us to investigate the expression of AP-1 transcription factors in human fibrotic diseases and we observed a striking up regulation and activation of c-JUN in the mesenchymal cell compartment of all fibrotic conditions analyzed. In addition, c-JUN was responsible for the pathologically increased proliferation of fibroblasts of patients with idiopathic pulmonary fibrosis. To evaluate whether this c-Jun up regulation may functionally contribute to the fibrogenic process we generated a c-Jun inducible mouse. Remarkably, we found that fibroblasts selectively responded to c-Jun despite ubiquitous c-Jun induction. Multiple organs developed striking fibrosis reminiscent of human disease. Single cell mass cytometry analysis in mouse and human fibrosis revealed that transcriptional effects of c-Jun lead to a profound re-wiring of active signaling pathways in human lung fibrosis, which we exploited for effective therapeutic intervention in mice.

Figure 1B:
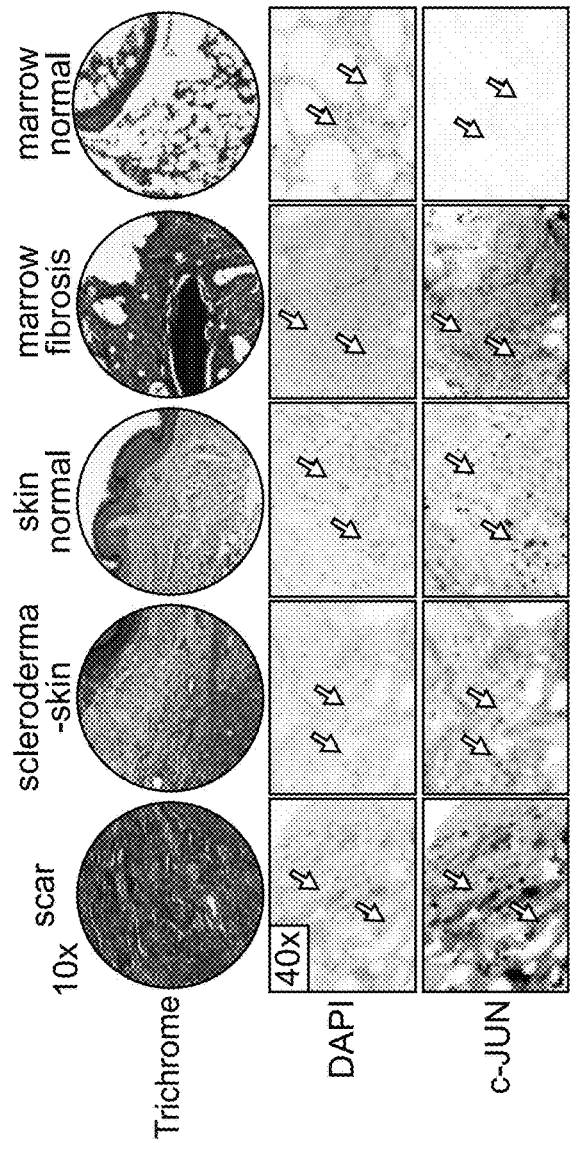
Figure 1C:
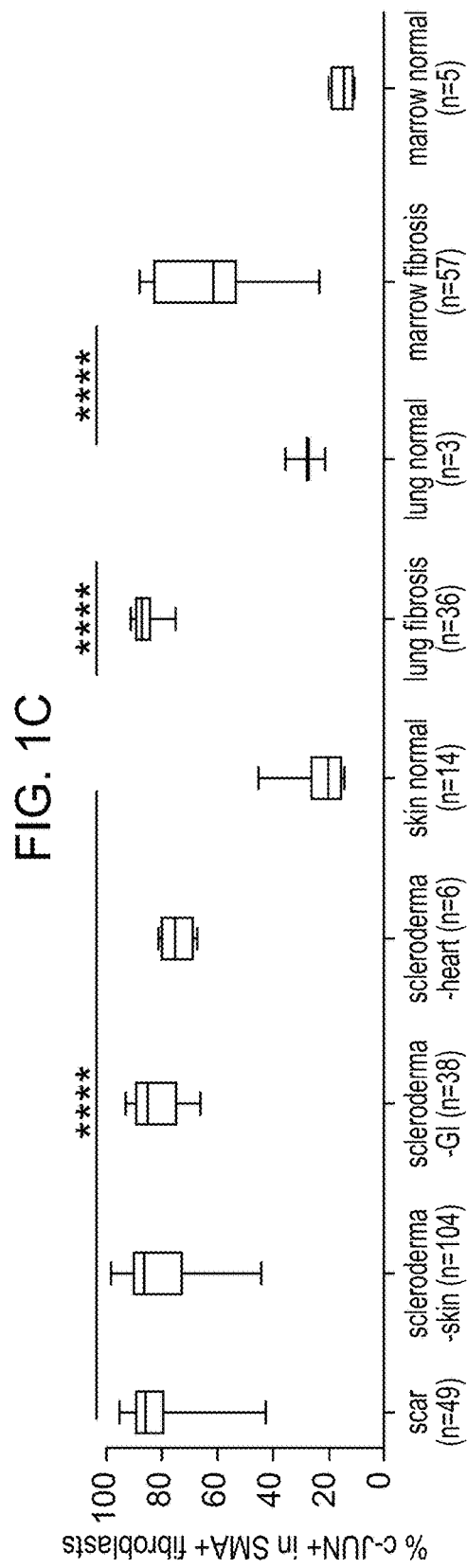
Figure 1D:
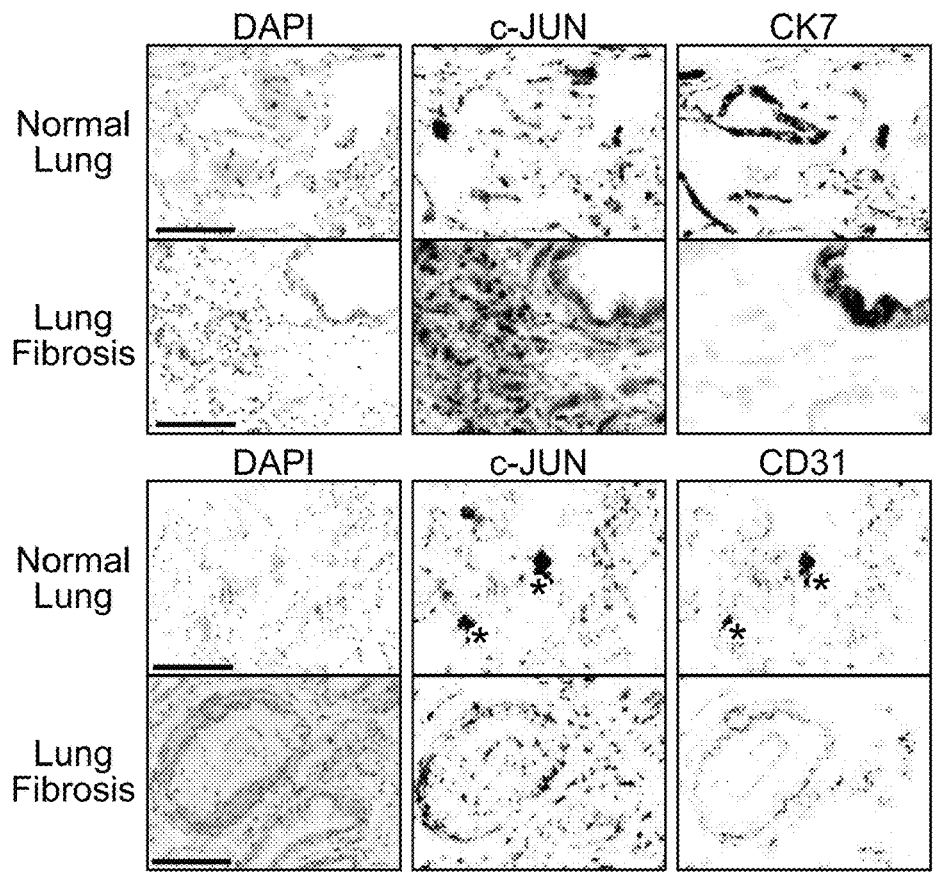

Results c-JUN is expressed in all major human fibrotic diseases. Previously, we had observed the upregulation of AP-1 transcription factors in a mouse model of polycythemia vera that also recapitulated features of bone marrow fibrosis. We therefore sought to analyze the expression of c-JUN in human fibrosing diseases. Given the cellular heterogeneity in fibrotic lesions we performed a thorough immunohistochemical analysis. A total of 454 biopsies from patients with different fibrotic conditions were stained with H&E, trichrome and with antibodies against Collagen1, SMA and c-JUN (FIG. 1). 148 biopsies were analyzed from patients with systemic sclerosis (skin lesions (n=104), gastrointestinal (n=38) and heart (n=6)), 36 biopsies with idiopathic lung fibrosis, and 57 with primary myelofibrosis, and 164 from fibrosing conditions involving the liver (related to non-alcoholic steatohepatitis (NASH)/hemochromatosis, ethanol (ETOH)/hepatitis C (HCV), alpha-1-anti-trypsin (A1A) deficiency and chronic rejection), the kidneys (systemic lupus erythematosus (SLE)-related and reflux related) and the bladder, the pancreas, the heart, but also intraabdominal and pleural adhesions and were matched with normal tissues if available (FIGS. 1A-B). Quantification of the immunofluorescence analysis demonstrated that a much higher fraction of $SMA^+$ fibroblasts expressed nuclear c-JUN in all these fibrotic diseases compared to three control conditions (p<0.0001) (FIG. 1C). Co-staining of c-JUN with SMA (smooth muscle, fibroblasts), CK7 (epithelium), CD31 (blood vessel endothelium) demonstrated that the vast majority of c-JUN expressing cells are fibroblasts and only rarely nuclear c-JUN can be found in other cell types (FIGS. 1A and D).

Figure 1E:
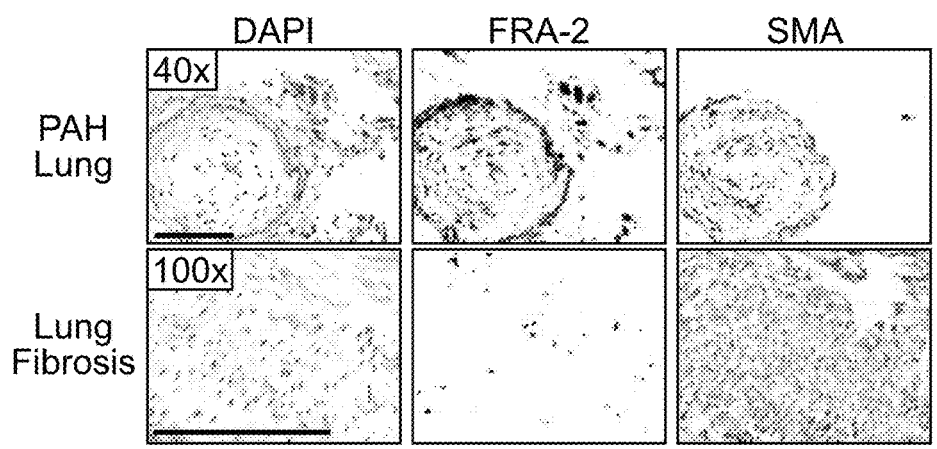

Nuclear c-JUN is the predominant AP-1 transcription factor identified in pathogenic fibroblasts in fibrotic plaques of human lung fibrosis and other fibrosing diseases. Since the c-JUN-related factor FRA-2 has been previously described in a murine model of pulmonary vasoocclusion and subsequent fibrosis we tested whether FRA-2 would be co-expressed with c-JUN in lung fibrosis and other fibrosing diseases. Indeed, resembling the described mouse model remarkably closely, nuclear FRA2 was readily detectable in biopsies of pulmonary artery hypertension (PAH) in particular in pathologically thickened PAH vessels (FIG. 1E top panel). However, we failed to detect nuclear FRA-2 staining in the majority of fibroblasts in other fibrosing diseases including the most common interstitial pneumonia-type of idiopathic pulmonary fibrosis (IPF) (FIG. 1E, bottom panel).

Figure 2A:
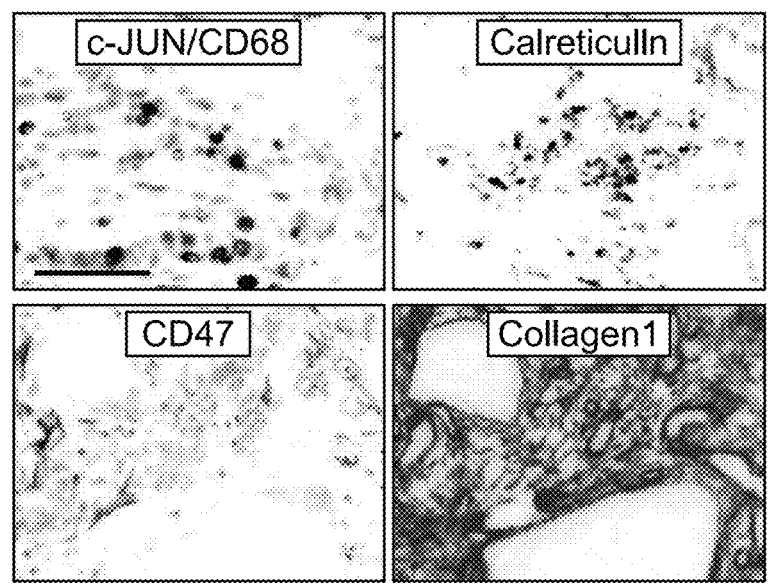
FIG. 2A-2E. The signaling involved in the pathogenic process of lung fibrosis.

This finding prompted us to systematically investigate the expression of additional AP-1 transcription factors. Immunohistochemical analysis of fibrosing conditions of the lung, liver, kidney, bladder, pancreas, heart, and visceral adhesions confirmed strong c-JUN expression, but found c-FOS occasionally expressed in fibrotic lesions in lung fibrosis, but not nuclear FRA-2 and FOS-B (FIG. 1E). None of the remaining AP-1 transcription factors JUNB, JUND, and FRA-1 were detectable. In addition, we profiled biopsies of idiopathic pulmonary fibrosis patients with Multiplexed ion beam imaging (MIBI), a new technology which allows concomittant staining of archival tissues with up to 100 markers at the single cell level and provides histologic resolution. We profiled archival tissue sections of idiopathic pulmonary fibrosis patients for all AP-1 transcription factors. While we detected abundant c-JUN signals in fibrotic areas additionally highlighted by CD47 and collagen1 we did not detect significant levels of nuclear FRA2. These data confirmed our immunohistologic results and suggest that while c-JUN can act as a homodimer it also forms heterodimers with c-Fos in idiopathic pulmonary fibrosis.

c-JUN-positive fibroblasts are surrounded by macrophages and express the CD47 "don't eat me" signal in idiopathic pulmonary fibrosis lungs. A complex interplay between the immune system and mesenchymal cells is considered important for the pathogenesis of fibrosing diseases. We therefore analysed lung samples of patients with idiopathic lung fibrosis for the presence of immune cells and observed large numbers of CD68+ macrophages interspersed with c-JUN-expressing fibroblasts (FIG. 2A top panel). This finding raised the question why fibroblasts are not phagocytosed by macrophages. We therefore investigated the expression levels of anti-phagocytotic "don't eat me" signals and found that both CD47 and calreticulin were expressed in a subset of collagen I positive pathogenic fibroblasts (FIG. 2A top and bottom panels).

Figure 2B:
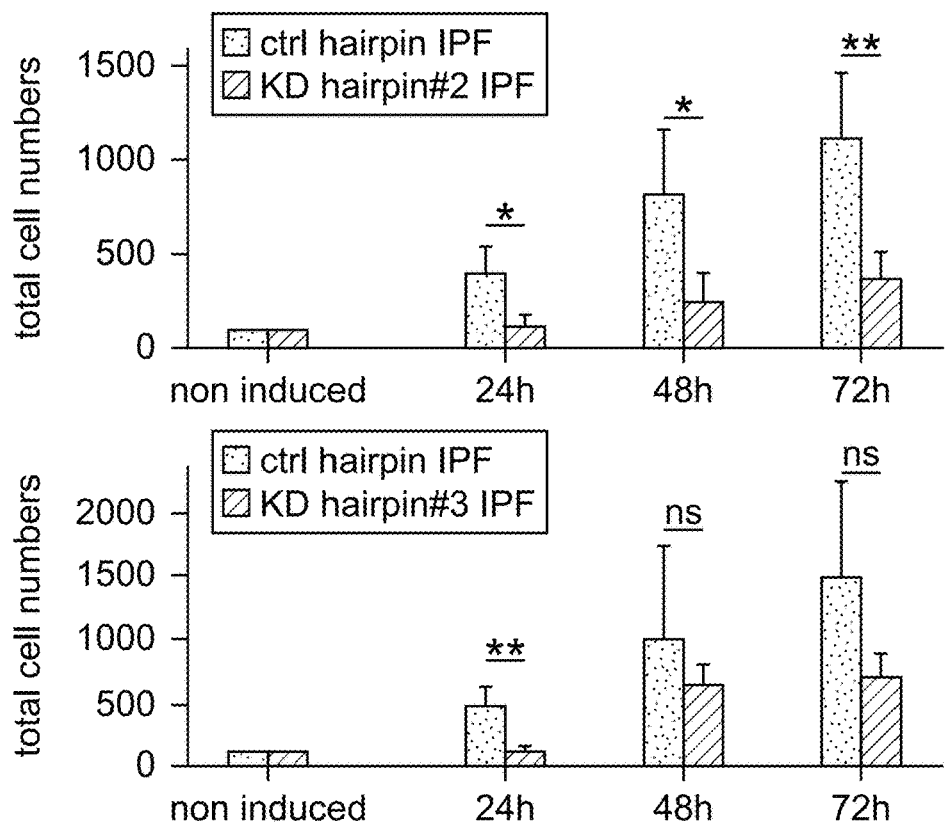
Figure 2C:
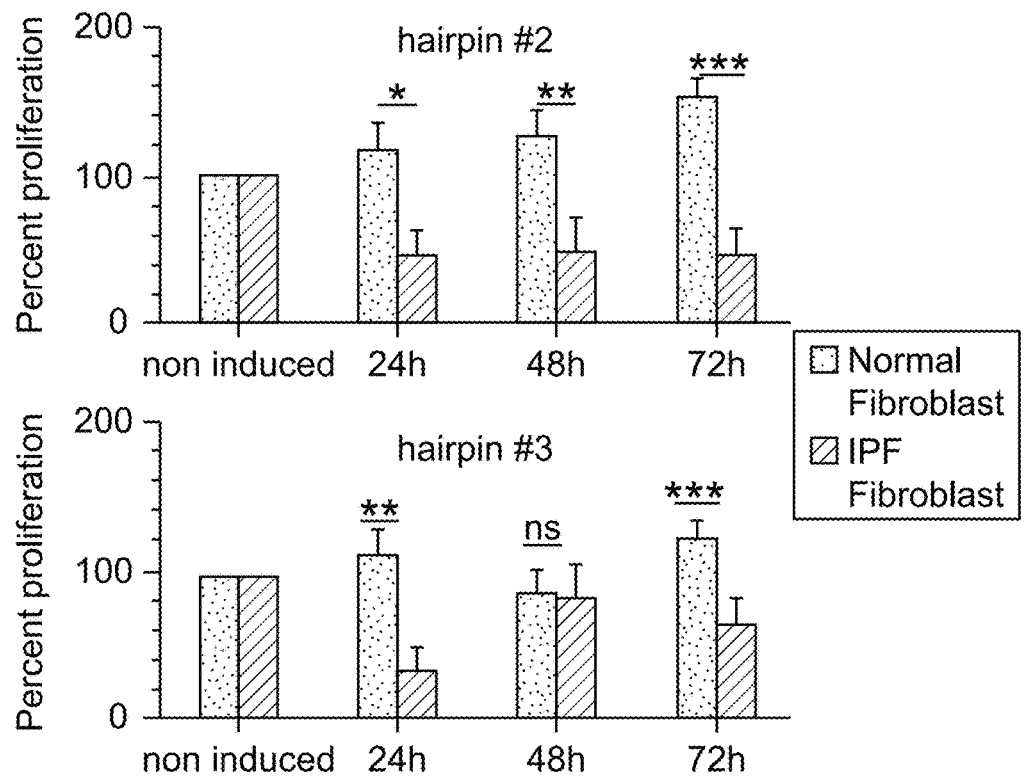

Pathogenic but not normal fibroblasts require c-JUN for rapid proliferation. To further investigate a functional role of c-JUN in pathogenic fibrosis, we knocked down c-JUN in primary lung-derived fibroblasts isolated from patients with IPF and normal lung tissue with 2 different hairpins. First, we confirmed that both hairpins achieved substantial decrease of c-JUN mRNA. Both hairpins substantially reduced the proliferation rate of IPF fibroblasts compared to the control hairpin at various time points after plating (FIG. 2B black bars). Surprisingly, we found that normal lung-derived fibroblasts do not_require c-JUN, these healthy lung fibroblasts continue to grow upon c-Jun knockdown (FIG. 2C white bars).

Figure 2D:
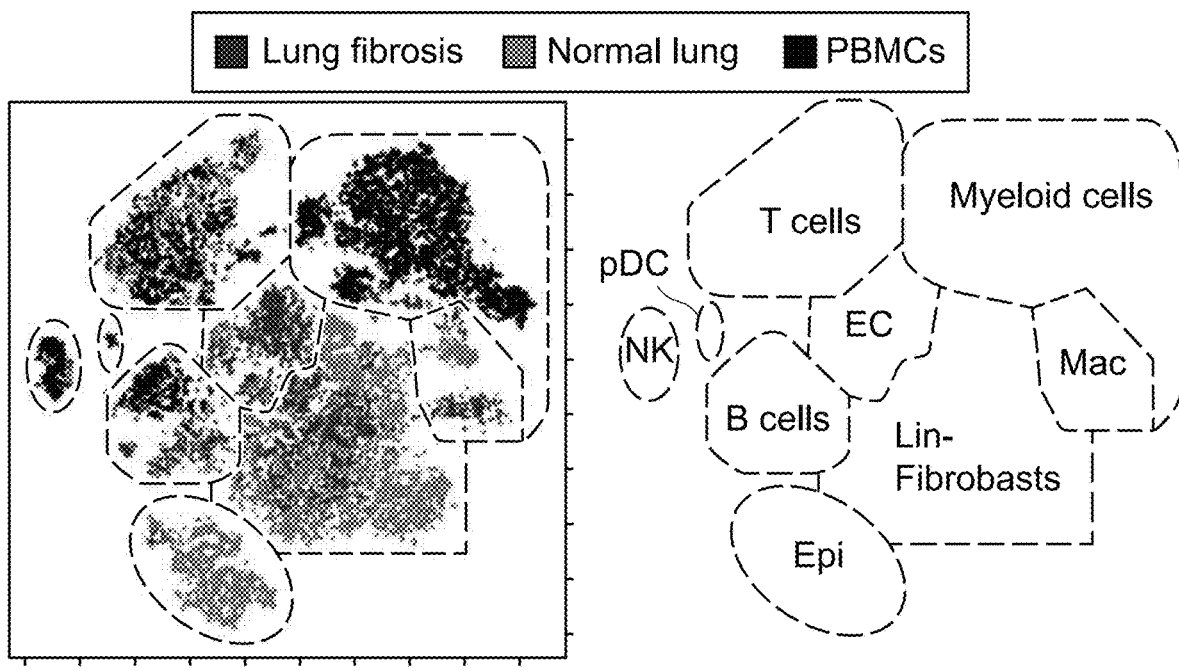
Figure 2E:
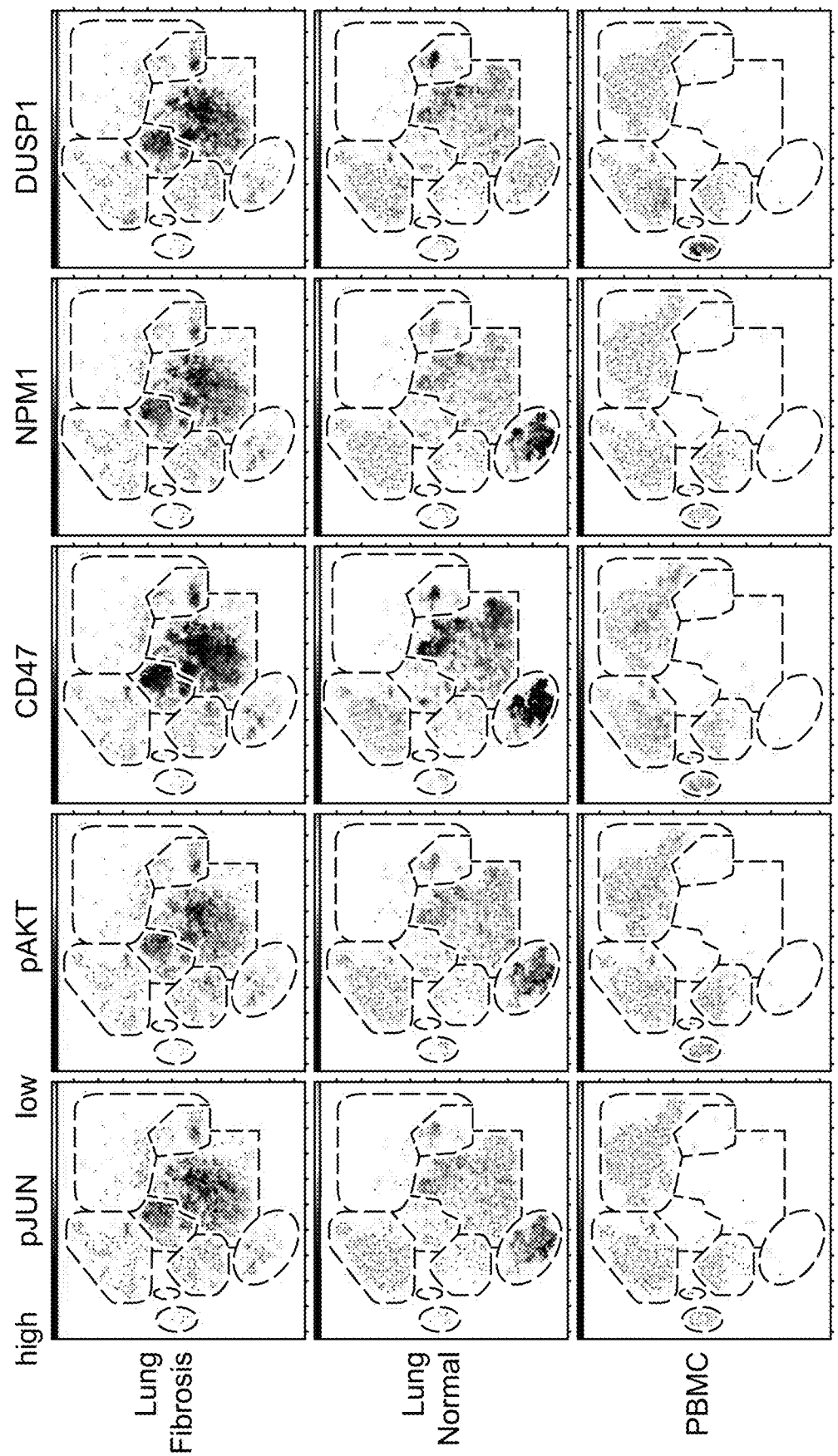
Figure 3A:
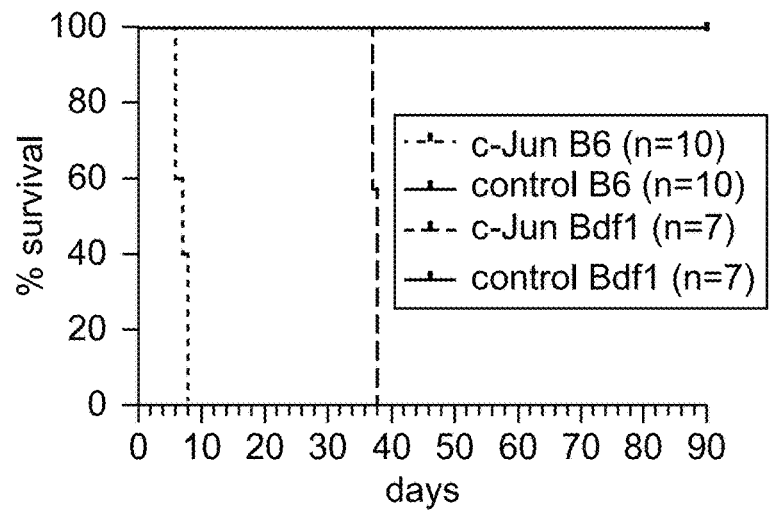
FIG. 3A-3H. c-Jun expression caused severe bone marrow fibrosis mediated predominantly by bone marrow stromal cells and only weakly influenced by hematopoietic cells.
Figure 3B:
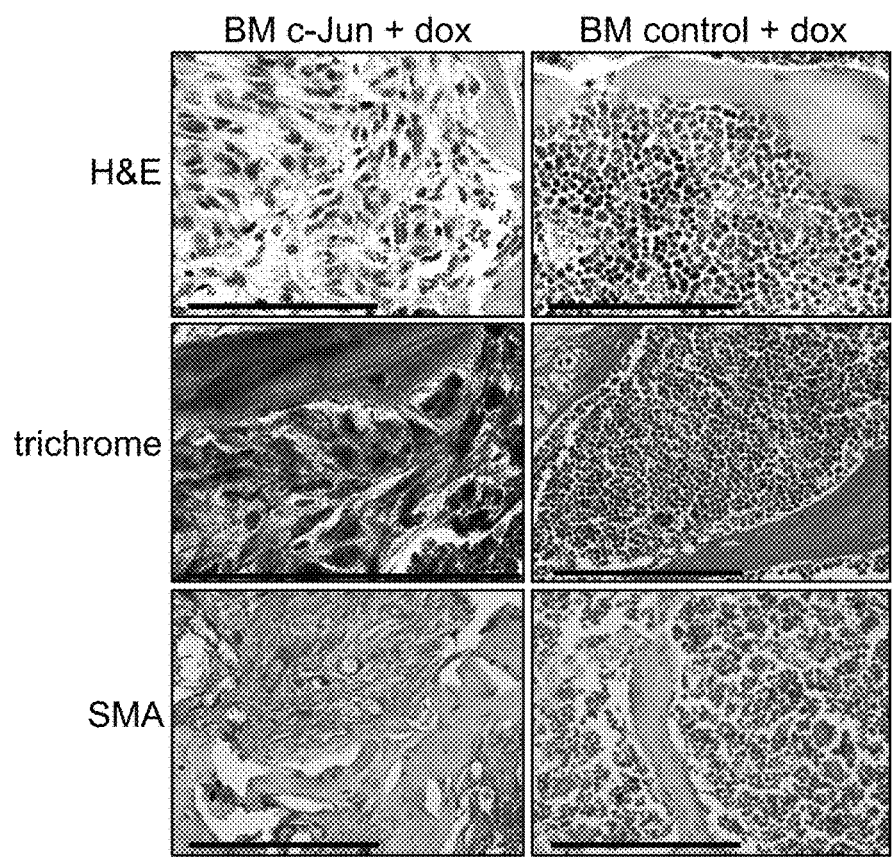
Figure 3C:
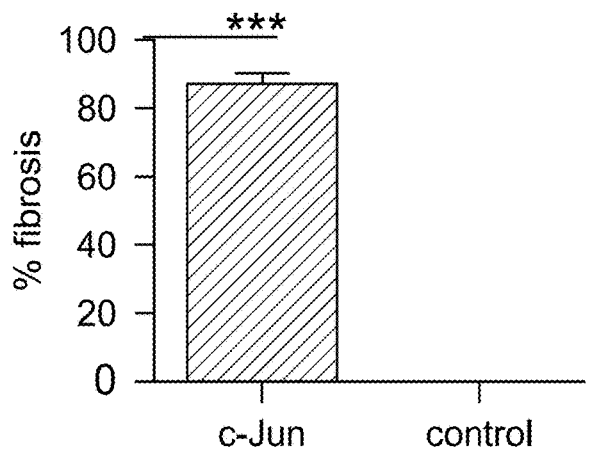

Pathogenic fibroblasts activate phospho c-JUN and AKT pathways in human fibrotic lesions in vivo. Next, we sought to characterize the activity of various signaling pathways in normal and fibrotic human lungs. We took advantage of the multidimensional capabilities of flow-based single cell mass cytometry (CyTOF) and accompanying bioinformatic tools to better assess the signaling network as a whole at single-cell resolution. Freshly obtained lung biopsies from IPF patients were dissociated into single cells together with peripheral blood mononuclear cells (PBMCs) from controls and normal lungs. All cells from all three samples were stained together in one tube and analyzed in one run which reduces variability of the staining intensities. To resolve sample and cell identities, we barcoded the samples and stained the cells with antibody panels for lineage markers for epithelial cells (Epi), B cells, natural killer cells (NK), plasmacytoid dendritic cells (pDC), T cells, endothelial cells (EC), myeloid cells, macrophages (Mac) and lineage marker negative fibroblasts (Lin⁻ fibroblasts). To visualize and interpret the high-dimensional dataset generated by mass cytometry, we applied the viSNE algorithm using 34 markers where cells in the high-dimensional space were projected onto a two dimension map while preserving their neighboring relationship. FIG. 2D shows a plot of the viSNE analysis where each dot represents an individual cell colored by sample identity. The expression of lineage markers further indicated where the different cell types are localized in the viSNE plot (groups circled by dashed lines in FIG. 2D). The simultaneous analysis of signaling pathway and cell-type specific markers allowed us then to measure the steady-state activity of multiple pathways separately for each cell population in vivo. Both phospho c-JUN and phospho AKT were highly induced in lung fibrosis fibroblasts but not fibroblasts in normal lungs (FIG. 2E). Instead, both signaling molecules were largely restricted to epithelial cells in normal lungs. In addition, we noticed upregulation of the transcription factor NPM1 and the phosphatase DUSP1 specifically in pathogenic but not normal lung fibroblasts. NPM1 is a transcriptional target of c-JUN and DUSP1 is known to enhance phospho c-JUN activity by negatively regulating the MAPK pathway thus indirectly activating the PI3K-kinase pathway. Finally, we observed a striking upregulation of CD47 in pathogenic fibroblasts of lung fibrosis samples potentially explaining their resistance to macrophage-based removal.

c-Jun but not JunB induces severe marrow fibrosis in mice. To dissect the functional relevance of AP-1 transcription factor up-regulation, that we observed in patients, we generated c-Jun and JunB Doxycycline (dox)-inducible mice by gene targeting in mouse embryonic stem cells followed by blastocyst injection of the transduced cells. In this expression system the reverse tetracycline transactivator (rtTA) is ubiquitously expressed from the Rosa26 locus and the inducible cassette is targeted downstream of the Col1a1 locus, leading to robust and reliable drug-dependent transgene induction in most tissues. In both mouse strains c-Jun and JunB protein, respectively were readily induced after dox administration for 2 days in the drinking water. Surprisingly, only 4 days after induction of c-Jun, hybrid F1 129/C57Bl/6 mice became moribund and died in a small time window between 6 to 8 days later. In the BDF1 genetic background the mice also died almost synchronously but survival was prolonged to about 38 days (FIG. 3A). Before death, the mice exhibited scruffy fur and stiff skin, wheezing and exhibited prolonged bleeding. Initially, we focused our histopathologic analysis on the bone marrow which revealed striking cellular fibrosis, disappearance of hematopoietic cells, and collagen deposition in 87% of the surface area, fulfilling all clinico-pathological criteria of grade 3 marrow fibrosis (FIG. 3B,C). Time course analysis of the bone marrow demonstrated that pancytopenia and fibrosis in c-Jun induced animals were progressive between days 2 through 6. The spindle shaped cells forming the fibrosis were labeled with reticulin, trichrome and smooth muscle actin stainings (FIG. 3B, middle and bottom panels). Gross morphologic paleness and single femur cell counts revealed severe cytopenia in the marrow with an over 9-fold reduction in the total number of bone marrow cells ($2.5 \times 10^6$ versus $15 \times 10^6$, $p<0.01$) in c-Jun induced mice. Annexin V/7AAD stains indicated a distinct c-Jun mediated cell type specific response, mainly a significant increase in the apoptosis in c-Jun expressing hematopoietic precursors, suggesting cell death rather than migration as the primary mechanism accounting for the rapid disappearance of hematopoietic cells from the fibrotic bone marrow.

Figure 3D:
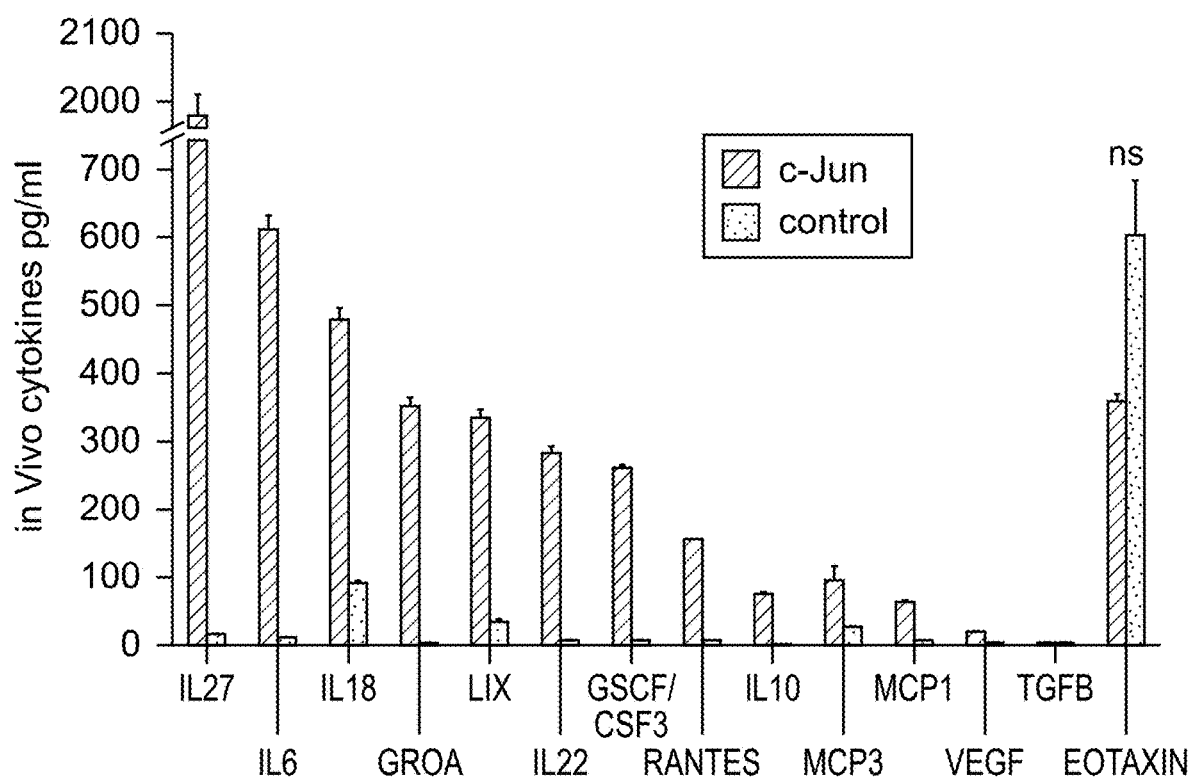
Figure 3E:
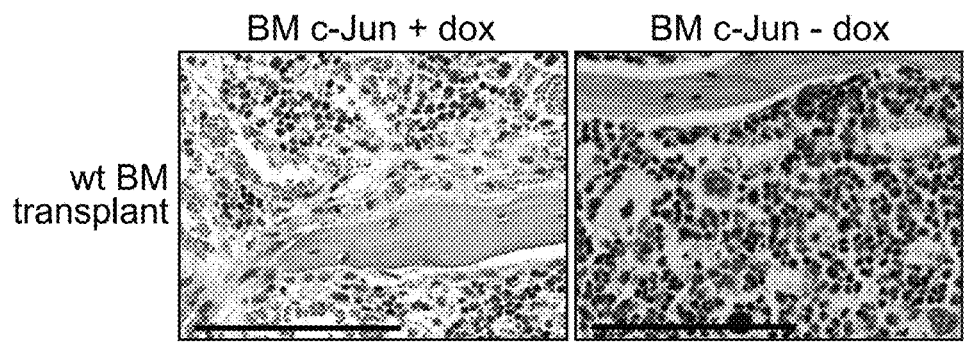
Figure 3F:
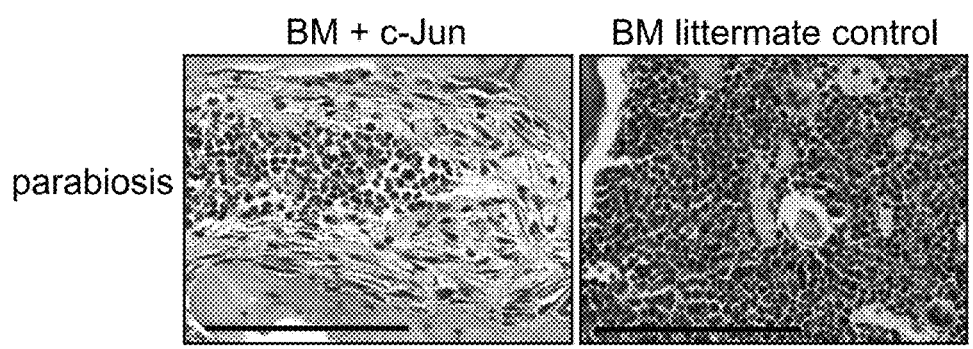
Figure 3G:
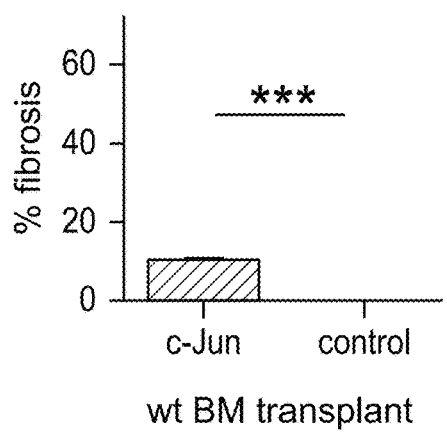
Figure 3H:
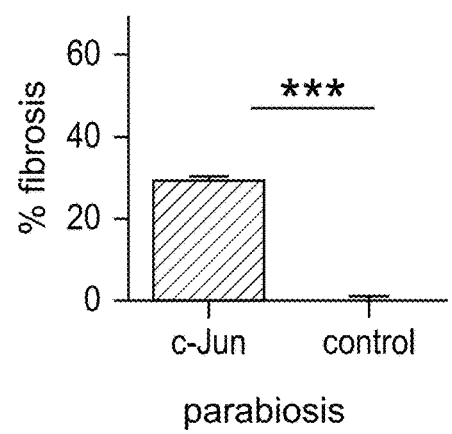

In contrast, none of the JunB-inducible mice showed any signs of disease after up to 8 months of doxycycline treatment. Histopathological analysis revealed bone marrow cellularity and composition indistinguishable from control mice of the same age. Thus, fibrogenesis is specifically induced by c-Jun and not by the related AP-1 transcription factor JunB.

c-Jun-induced marrow fibrosis is primarily mediated by stroma cells with some contribution from hematopoietic lineage cells. We next sought to address whether c-Jun induction in the hematopoietic or mesenchymal cell population is responsible for fibrogenesis and whether the effects are mediated in a cell autonomous manner as could be expected from a transcription factor. First, we transplanted whole bone marrow of c-Jun-inducible mice into wild type recipients. Despite nearly 100% blood chimerism no fibrosis was detected after dox treatment suggesting the hematopoietic compartment alone is insufficient to induce fibrogenesis. Next, we injected $1\times10^6$ CD45.1 wild type (WT) whole bone marrow into c-Jun inducible mice expressing CD45.2. After 25 days the bone marrow was nearly completely reconstituted with WT donor cells. Upon dox treatment fibrosis formation occurred but was substantially suppressed compared to non transplanted c-Jun-inducible mice (FIGS. 3E and G, compare with B). To independently confirm these results, we performed a parabiosis experiment allowing blood exchange following anastomosis of the circulation of c-Jun inducible and litter mate control mice for 3 weeks, a time point at which peripheral blood chimerism is known to be established. One week after dox treatment the bone marrow fibrosis was present but markedly suppressed in c-Jun mice parabiosed to wildtype mice (FIGS. 3F and H, compare with B). To understand which blood cell subsets are contributing to fibrosis we investigated c-Jun mediated fibrogenesis in NOD-SCID IL2R-gamma and RAG2-gamma knock-out mice lacking B, T and NK cells. Fibrosis developed in all conditions demonstrating that other blood cell types, such as macrophages, modulate the fibrogenic process. To understand whether chemokines and cytokines play a role in c-Jun mediated fibrosis we quantified cytokine/chemokine concentrations in the serum of mice 48 hours after systemic c-Jun induction with a comprehensive cytokine/chemokine luminex bead assay. Compatible with the non-cell autonomous effects of hematopoietic cells we observed drastic upregulation of a large number of immunomodulatory cytokines (FIG. 3D).

Figure 4A:
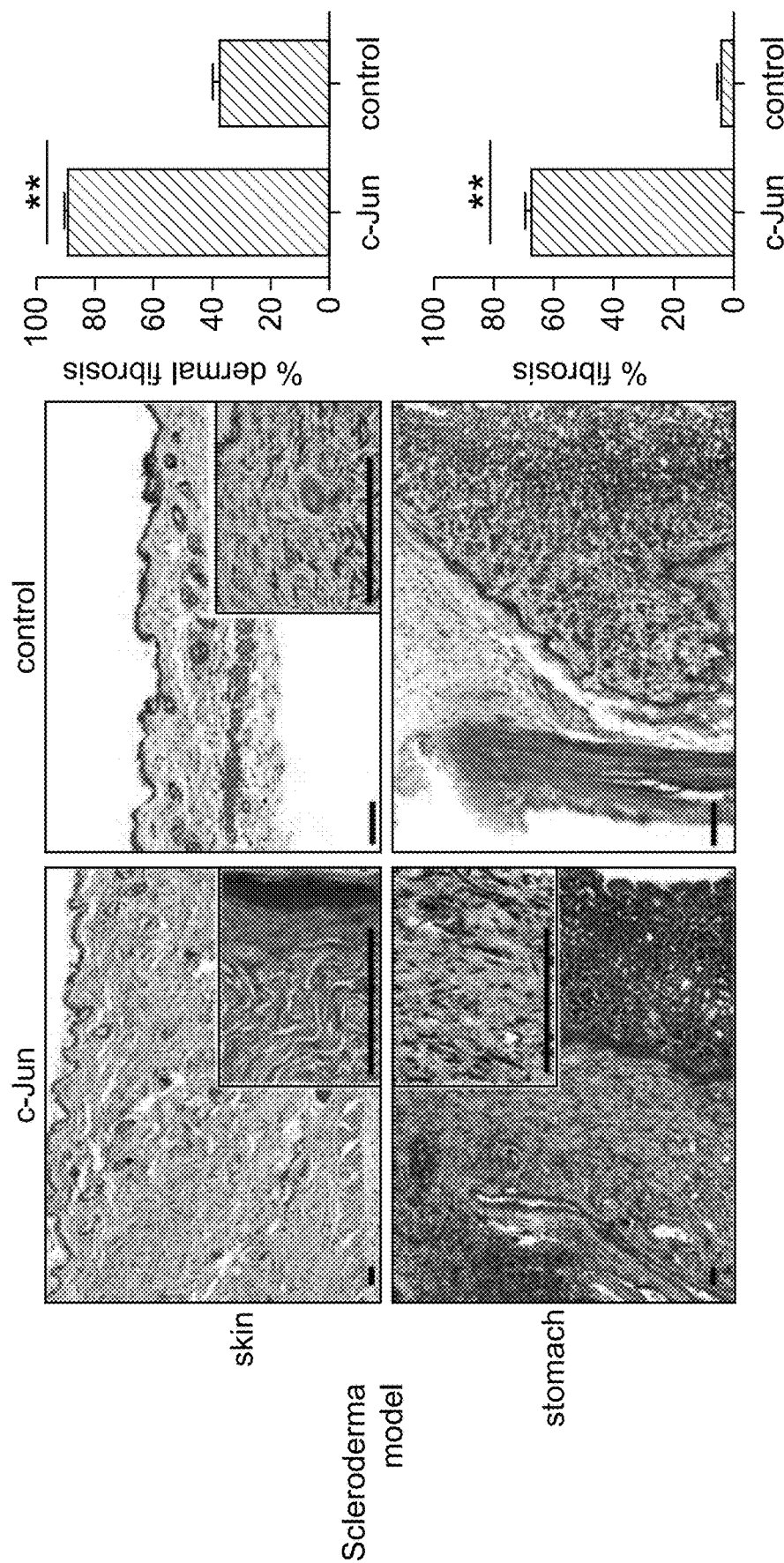
FIG. 4A-4H. c-Jun expression caused fibrosis in multiple organs.

In summary, these observations establish that fibrogenesis can result from the direct induction of c-Jun in mesenchymal stroma cells which leads to a systemic release of potent pro-inflammatory chemo- and cytokines and induction in the hematopoietic compartment alone is insufficient. However, wild-type transplanted or circulating hematopoietic cells, likely macrophages, can partially suppress fibrogenesis in c-Jun marrows. Thus, the fibrosis is driven in a cell-autonomous manner by tissue fibroblasts but is modulated in a non cell-autonomous manner by the hematopoietic compartment compatible with the well-characterized interaction of inflammatory and fibrotic mechanisms in sclerotic disease.

c-Jun induces widespread fibrosis in multiple organs. In addition to bone marrow fibrosis, further more detailed histopathologic analysis of systemically c-Jun induced mice revealed severe fibrosis of the skin. This is illustrated by the blue trichrome staining that reveals that over 80% of the dermis is replaced with extracellular collagen deposition (FIG. 4A, upper panels). Moreover, several gastroenteric organs displayed similarly severe fibrotic alteration including the distal esophagus, stomach, and small intestine (FIG. 4A, lower panels). Fibrotic alterations of skin and gastroesophageal junction are characteristic histopathological diagnostic criteria for the human condition of systemic sclerosis.

Other organs were much less affected, such as the lung that showed only a mild interstitial fibrosis. Given the short time window of analysis due to rapid death, we next asked whether tissue-restricted induction of c-Jun may cause fibrosis also in additional organs.

Figure 4B:
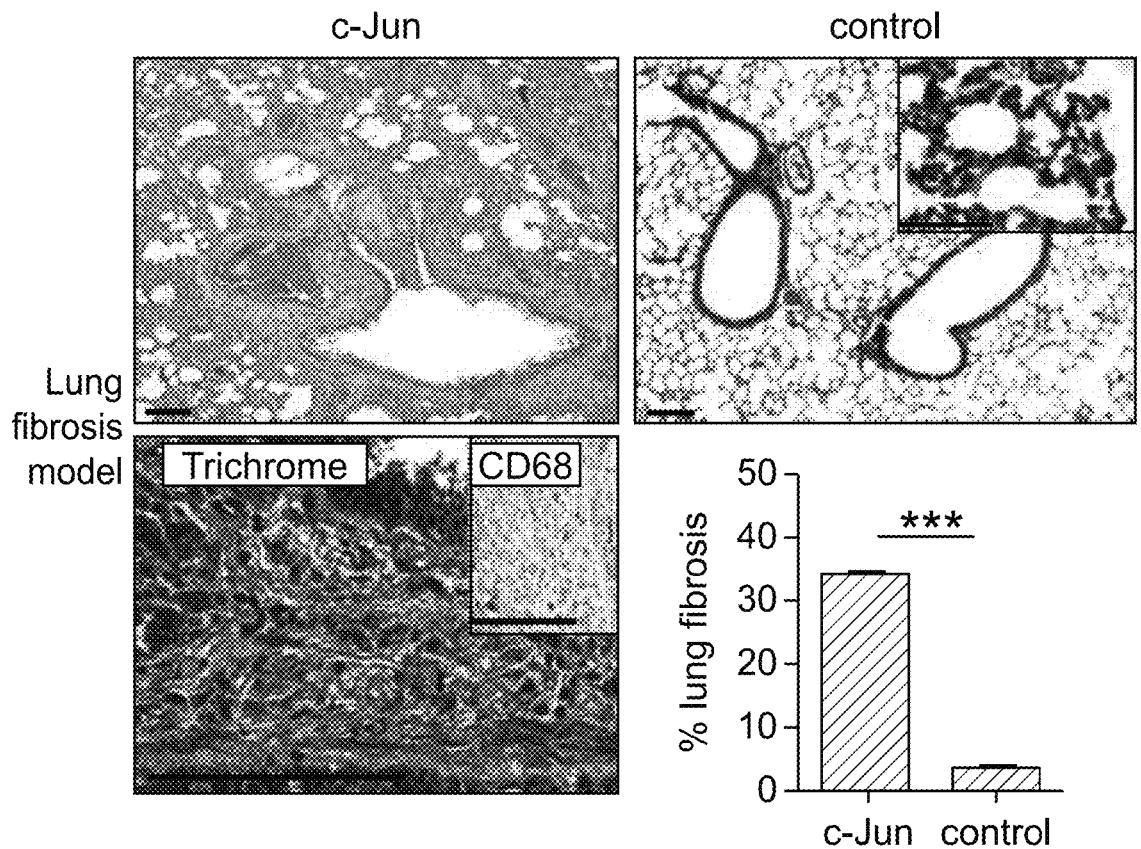

We first attempted to achieve more pronounced lung fibrosis by lung-restricted c-Jun induction via dox aerosol administration. Indeed, this treatment resulted in striking fibrosis with over 30% of the lung parenchymal tissue replaced with extracellular collagen as shown by trichrome stain (FIG. 4B). The collagen was distributed in a patchy interstitial pattern but also submesothelial, peripleurally, and surrounding the major airways. This process was reversible when dox administration was discontinued after 21 days and animals completely resolved the fibrosis and demonstrated normal histopathology at 300 days at study endpoint. In addition, we did not notice any fibrotic changes after intratracheal PBS administration in c-Jun inducible mice or with intratracheal dox in littermate controls lacking c-Jun. The admixed inflammation was comprised of abundant CD68$^+$ macrophages with fewer lymphocytes, plasma cells and neutrophils (FIG. 4B insert, bottom left). Since conventional volumetric assessment of lung function proved challenging in these sick mice, we measured CO gas diffusion which showed a functional impairment in gas exchange. Thus, the characteristic histopathological abnormalities and clinical presentation of mice following lung-restricted c-Jun induction closely recapitulated the human condition of idiopathic pulmonary fibrosis, in particular the most common usual interstitial pneumonia-type.

Figure 4C:
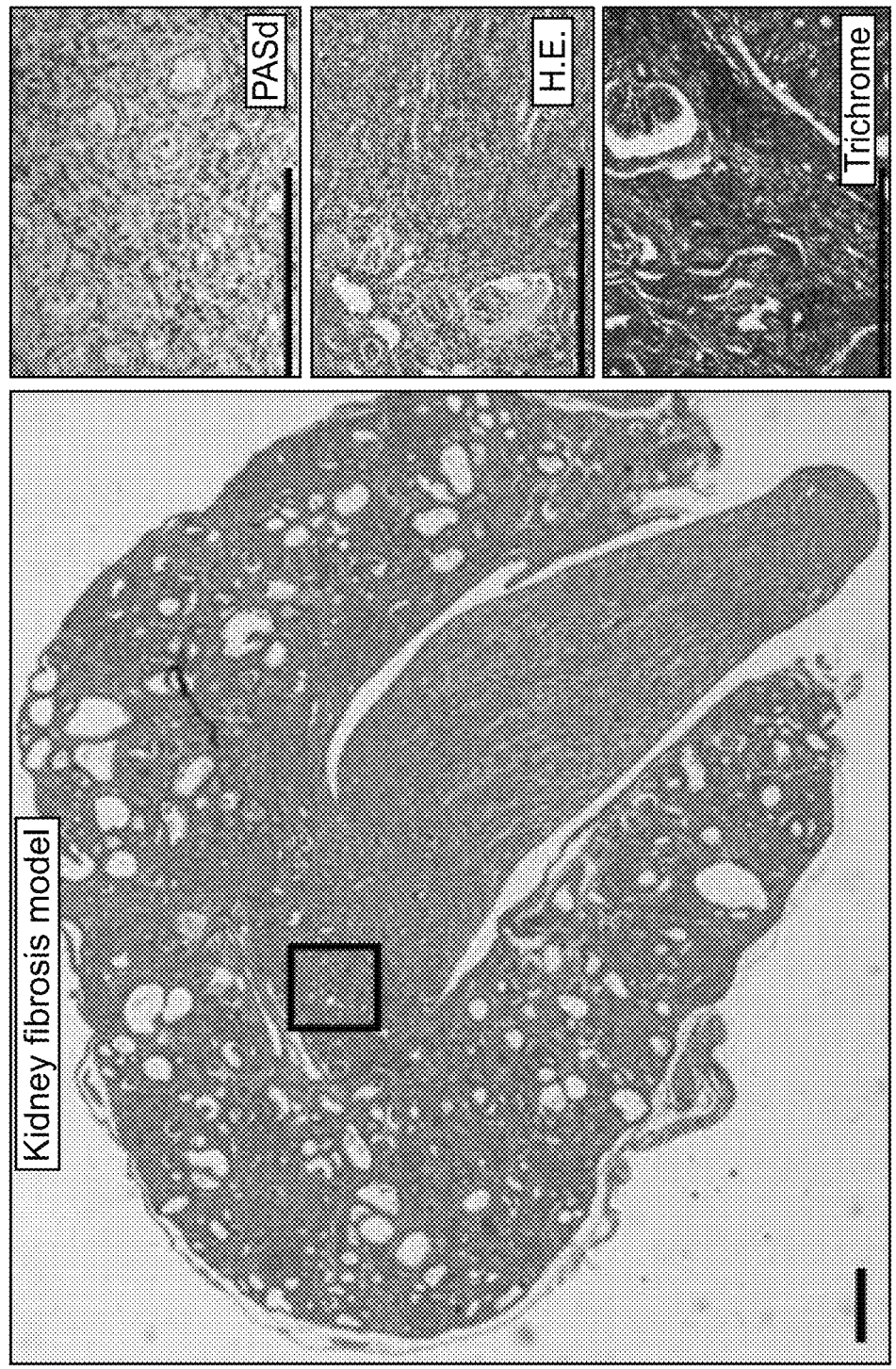

Next we crossed the tetO-c-Jun allele to Pax8-rtTA mice to accomplish kidney-specific c-Jun induction. After 8 weeks on dox water animals appeared moribund. Histopathologic analysis demonstrated 30-40% interstitial fibrosis of the kidney with abundant abnormal extracellular collagen matrix deposition labeled in blue with trichrome stain and tubular atrophy consistent with a primary tubulointerstitial nephropathy. In addition, serologic markers for kidney function such as blood urinary nitrate (BUN) and creatinine were significantly increased (FIG. 4C).

Figure 4D:
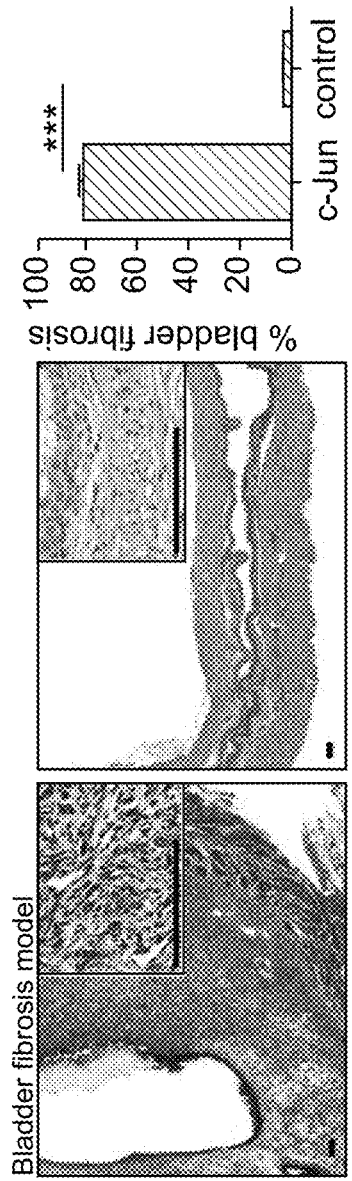

Next, we injected dox into the bladder to induce c-Jun specifically in the bladder. Again, c-Jun induction over 38 days resulted in bladder fibrosis with extracellular collagen matrix accumulation in 80% of the muscularis mucosae (FIG. 4D).

Figure 4F:
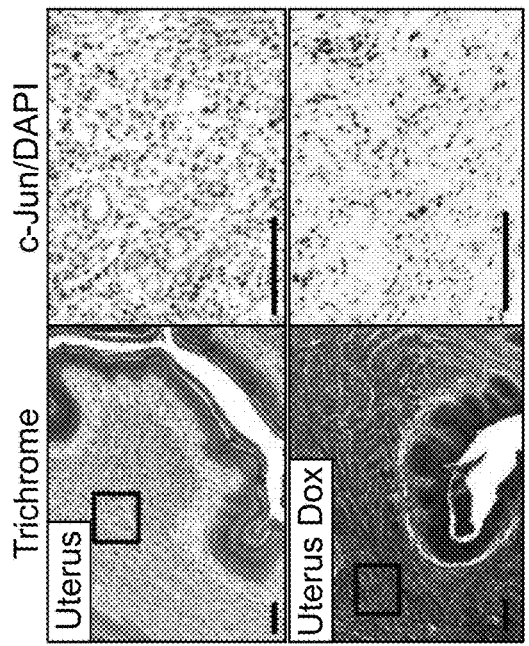
Figure 4E:
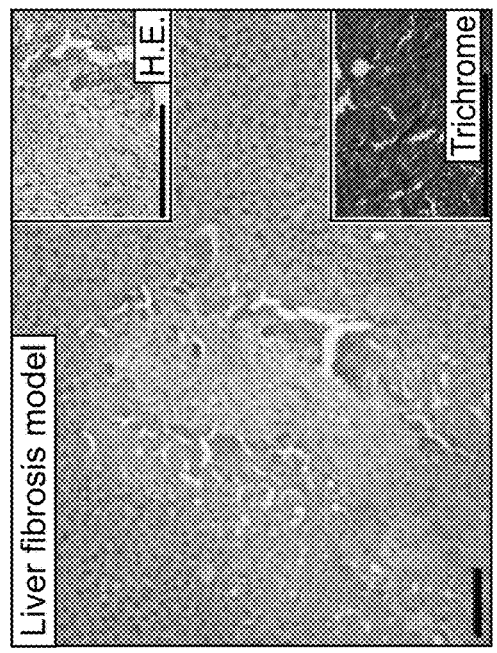

To evaluate the consequences of c-Jun induction in the liver and the uterus, we injected doxycycline intrahepatically and intramyometrically in c-Jun-inducible mice. Histopathologic analysis of the injury sites confirmed induction of nuclear c-Jun in fibroblastic cells and demonstrated fibrosis and trichrome$^+$ extracellular collagen matrix deposition at the injection sites 8 days after dox administration, but not elsewhere (FIG. 4E-F).

Figure 4G:
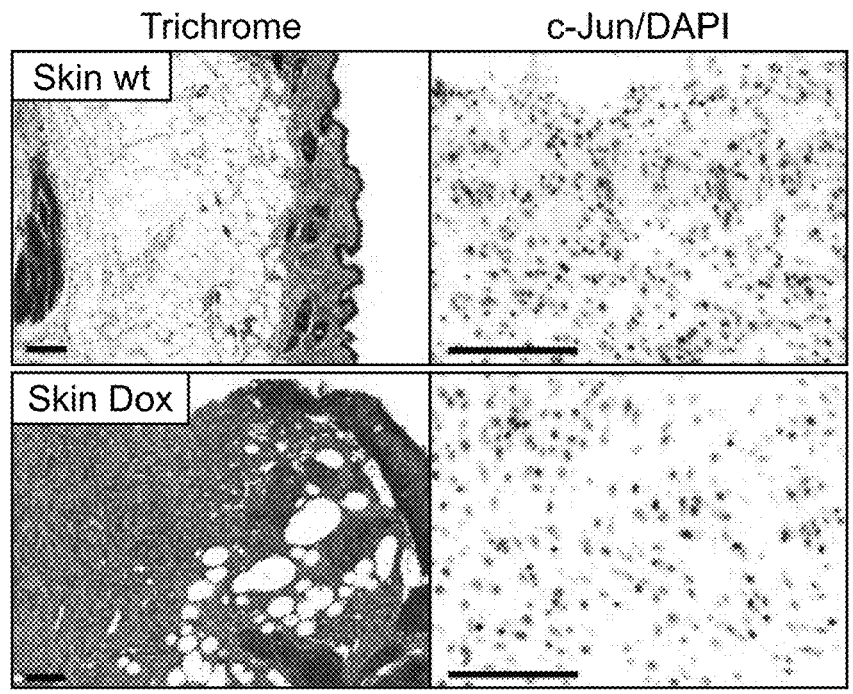
Figure 4H:
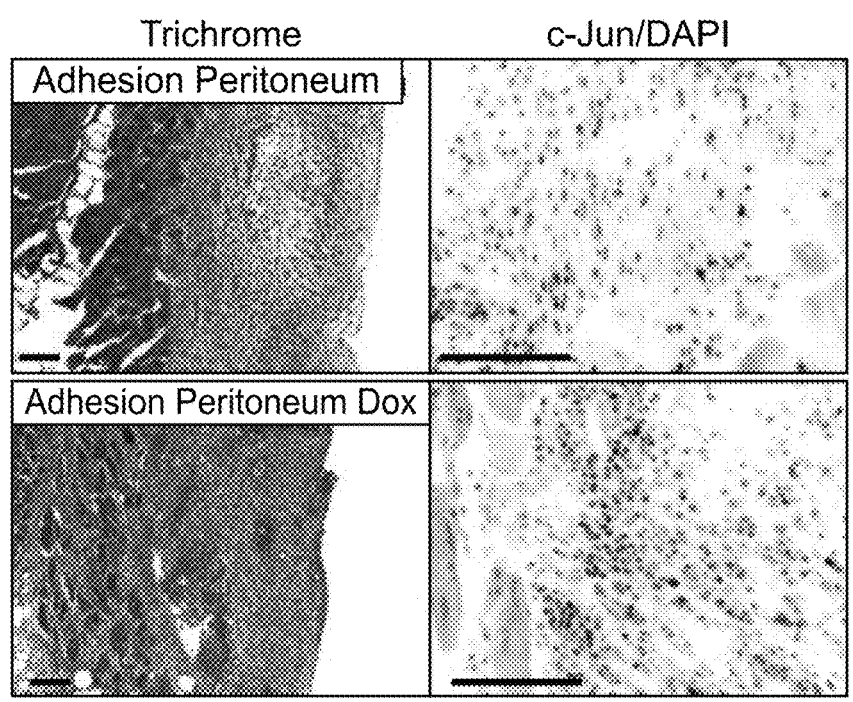

Since organ fibrosis is often compared to wound healing we were interested whether c-Jun may contribute to this process, too. To test this hypothesis we made a full-thickness incision into the dorsal skin of wild type and c-Jun-inducible mice and injected dox intradermally once a day for 5 days around the lesion site. After another five days, we analyzed the tissue and found pronounced deep dermal fibrosis and associated strong c-Jun induction in dermal fibroblasts in c-Jun-inducible but not control mice (FIG. 4G), confirming that c-Jun is a pro-fibrotic factor also during wound healing. We also tested a model of intra-abdominal adhesion formation by mechanical abrasion of the peritoneum. Ten days after abrasion and a single intra-lesional dox injection we observed adhesions in both wild type and c-Jun-inducible mice. The extent and density of fibrosis was much more pronounced in c-Jun-inducible mice (FIG. 4H). Importantly, we observed substantial c-Jun expression already in adhesions of wild type mice suggesting a potential role of c-Jun in mechanically induced adhesions.

Figure 5A:
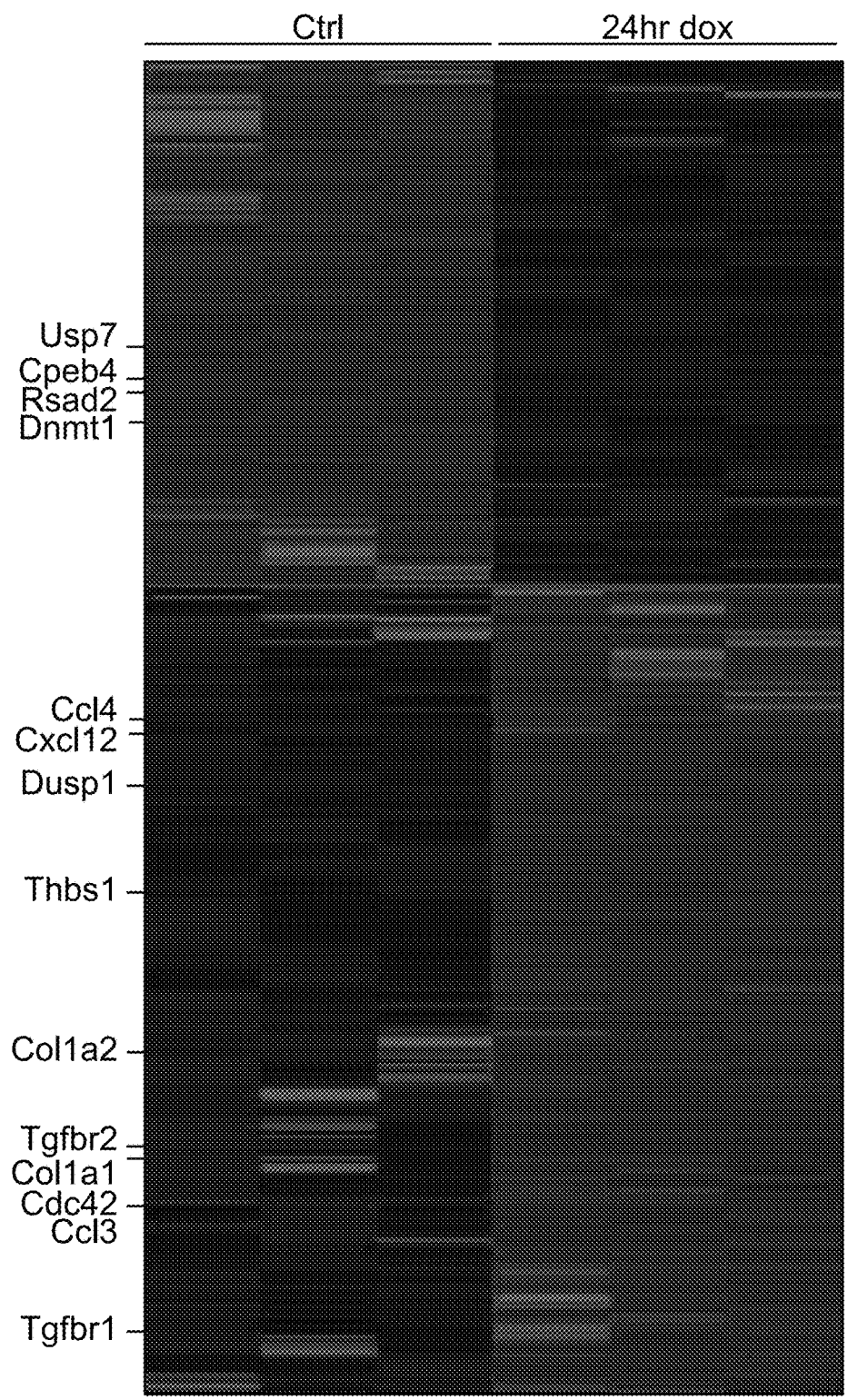
Figure 5B:
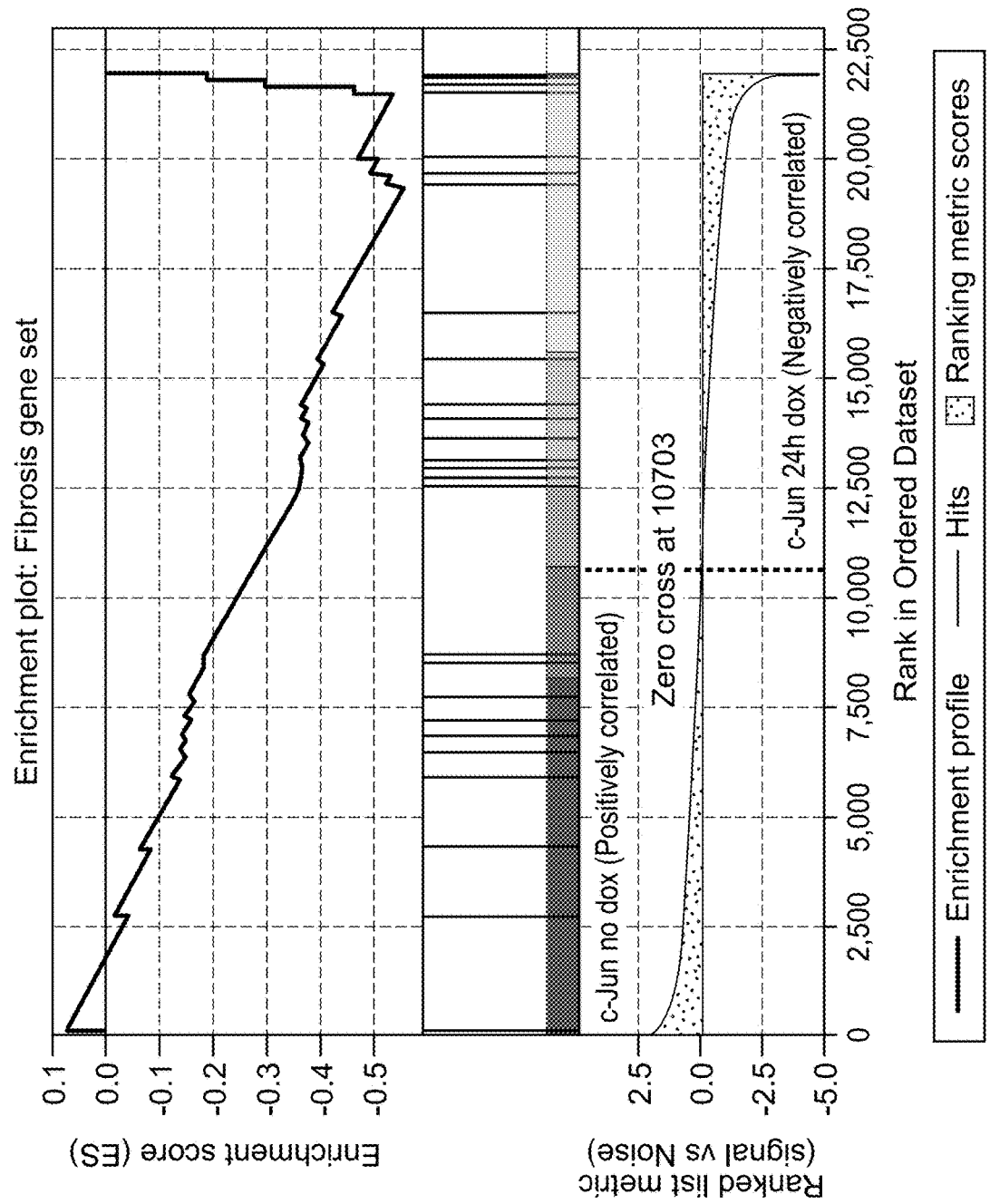

In summary, these findings demonstrate that c-Jun induction results in fibrosis in virtually all organs and in wound healing.

c-Jun induces feedback loops to rewire signaling pathways in a cell context-specific manner. To further explore the molecular pathways involved in c-Jun-induced fibrosis we performed genome-wide transcriptional profiling. We profiled whole bone marrow 24 hours after dox treatment of c-Jun inducible and control mice in vivo. Strikingly, already at this early time point many fibrogenesis-associated genes were induced such as Cdc42, Cxcl12 (also known as Sdf1), Tgfbr1 and 2, Ccl3, Ccl4, Collagen1a1, Collagen1a2, Collagen5a2 and Adiponectin, some of which are involved in migration (FIG. 5A). Amongst the top 100 upregulated genes were other representatives of the AP1 family, most notably c-fos. To confirm our RNA expression data we tested 43 cytokines and surface epitopes by direct immunofluorescence or flow cytometry and found Cxcl12 (Sdf1), Cxcr4, Thrombospondin-1, CD51, Vegfr and CD47 to be increased in c-Jun-induced cells. Specific interrogation of a fibrosis signature using gene set enrichment analysis (GSEA) revealed a significant enrichment in the c-Jun-induced cells (FIG. 5B). We next asked whether c-Jun, a target of the MAPK/JNK pathway itself, may in turn control the transcription of genes involved in upstream signaling pathways. To that end, we performed ingenuity pathway analysis and found transcriptional up-regulation of the MAPK pathway 24 hours post c-Jun induction.

Figure 5D:
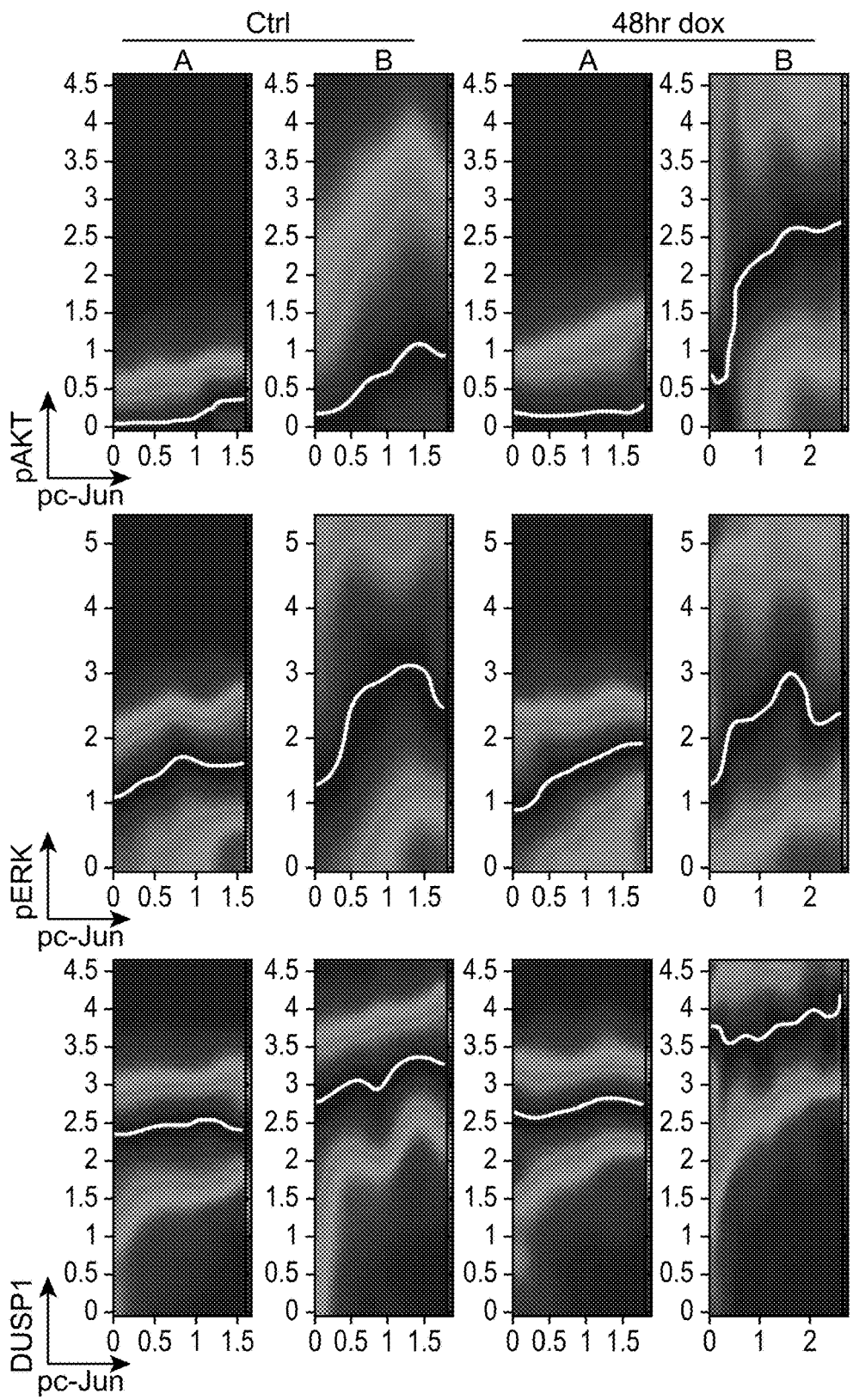

These transcriptional changes indicated that c-Jun once stimulated by upstream mechanisms may induce feedback loops to rewire the intracellular signaling networks that in turn may lead to fibrogenesis. To trace the origin and consequences of c-Jun mediated signaling in primary bone marrow stroma, we performed CyTOF analysis as we had done for primary human tissue. Primary bone marrow stroma cells with or without 48 hours of c-Jun induction were fixed and stained with 34 metal-conjugated antibodies against fibrogenesis-associated proteins (such as CD104, CD26, Sca1, Pdgfra, Fgfr, Vegfr, AdipoqR2, CD49b and CD49e), genes upregulated from transcriptional analysis (such as CD47, Npm1, Dusp1, Thrombospondin) and major signaling pathways related to c-Jun (such as the ERK1/2 MAPK pathway (pERK1/2 and pS6), the p38 pathway (pMAPKAPKII), pJNK, the AKT-mTOR pathway (pAKT and pS6) and Dusp1. The viSNE maps generated based on all 11 surface markers to the dataset, showed two clearly distinct subpopulations. One was characterized by high expression of macrophage lineage markers including CD172a and F4/80. The other subpopulation, CD172a and F4/80-negative cells, exhibited a much higher induction of phospho-c-Jun and c-Jun-induced molecules such as DUSP1 (FIG. 5C). To better understand the effect of c-Jun induction on signaling networks in both subpopulations, we took advantage of the inherent stochasticity at phospho c-Jun level between individual cells within each subpopulation and asked whether the state of a dependent signaling node would be correlated with the abundance of phospho-c-Jun. A conditional density-based algorithm, DREVI, was recently developed for this purpose to provide a way to visualize relationships between signaling nodes, which is well suitable for characterizing the rewired signaling network after c-Jun induction. As shown in FIG. 5D, this method computed the conditional density of the dependent signaling nodes on the y-axis for the corresponding pospho-c-Jun values on the x-axis. Among the measured signaling molecules, the DREVI plot revealed a digital type of response in the relationship between phospho-c-Jun and phospho-Akt only 48 hours after c-Jun induction in CD172a and F4/80 negative cells, where a sharp transition between low and high phospho-Akt was observed (FIG. 5D). In contrast, components of MAPK pathways were the major upregulated genes in the transcriptomic analysis at 24 hours, but there was no marked difference of phospho-Erk between before and after c-Jun induction regarding its relationship with phospho-c-Jun which might be due to the feedback inhibition from the simultaneous induction of DUSP1, a negative regulator of the MAPK pathway, by c-Jun. Remarkably, the F4-80$^+$ cells showed only little response to c-Jun induction. These results are very similar to the data obtained from human lung fibrosis tissue (see FIG. 2) illustrating that the molecular signaling cascades are well recapitulated in our mouse model and demonstrating that the induction of transcriptional regulator c-Jun can rewire intracellular signaling networks by robustly activating PI3K-Akt pathway while maintaining homeostasis in the MAPK pathway.

Figure 6B:
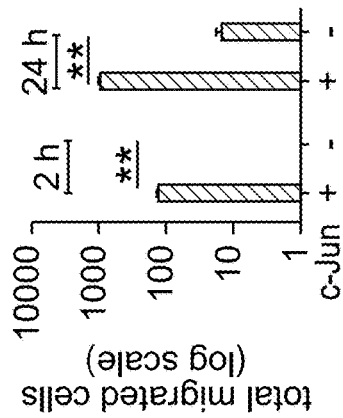
FIG. 6A-6K. Functional evaluation of signaling pathways and in vivo reversion of fibrosis following blockade of CD47, PI3K and VEGF pathways.
Figure 6A:

Functional evaluation of signaling pathways mediating the fibrogenic response. We next wished to assess the functional relevance of the signaling pathway rewiring induced by transcriptional activation of c-Jun. To enable systematic pharmacological interrogation we sought to develop a c-Jun-dependent in vitro assay. We assessed two cell biological parameters in cultured bone marrow-derived stromal cells from c-Jun-inducible mice. First, we assessed cell growth and observed a shortening of the cell doubling time from about 22 days in control to about 2 days in c-Jun-induced fibroblasts (FIG. 6A). Second, we measured cell migration of bone marrow-derived stromal cells in a transwell migration assay as a functional readout of the c-Jun induction and observed a 100-fold increase in migration at 2 hours and a 1000-fold increase at 24 hours in c-Jun induced cells versus uninduced cells (FIG. 6B).

Figure 6C:

Given its much greater dynamic range, we then tested a series of small molecule inhibitors in the transwell migration assay. Consistent with our mass cytometry findings, the c-Jun-induced migration was reduced to almost baseline levels in the presence of PI3K pathway inhibitors but not blockers of MAPK (such as MEK, p38), Jak, mTOR, Notch, hedgehog, GSK3 and EGFR (FIG. 6C).

Figure 6D:
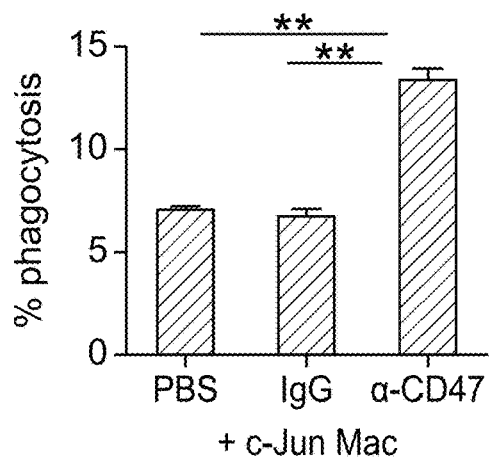
Figure 6F:
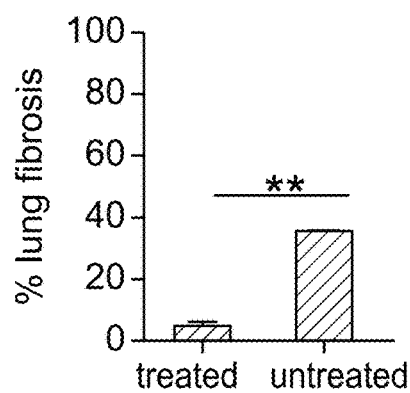
Figure 6E:
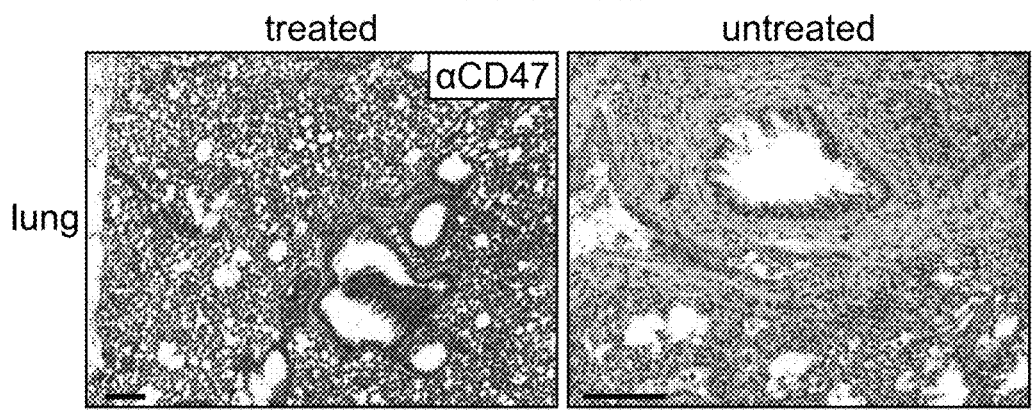
Figure 6G:
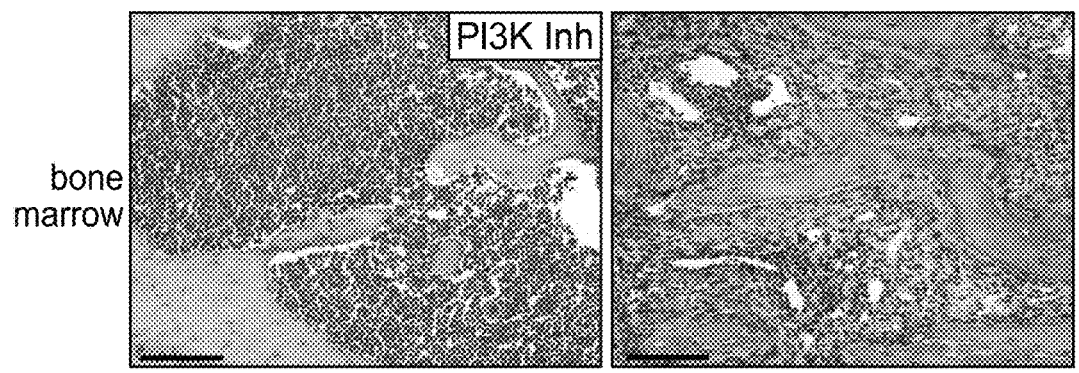
Figure 6H:
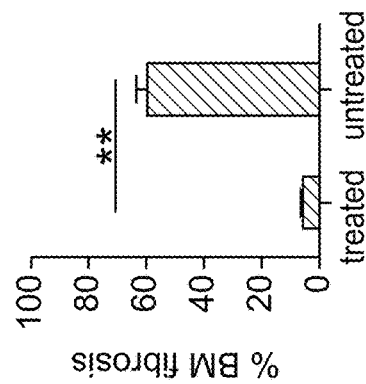
Figure 6I:
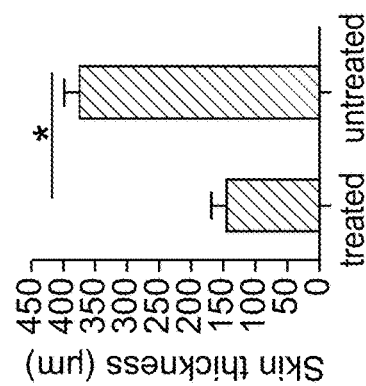
Figure 6K:
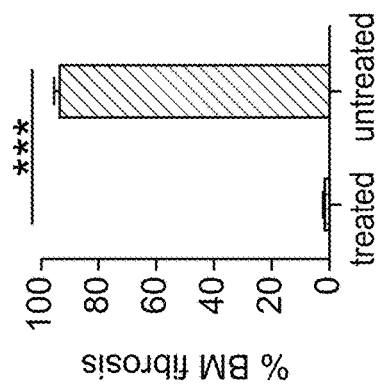
Figure 6J:
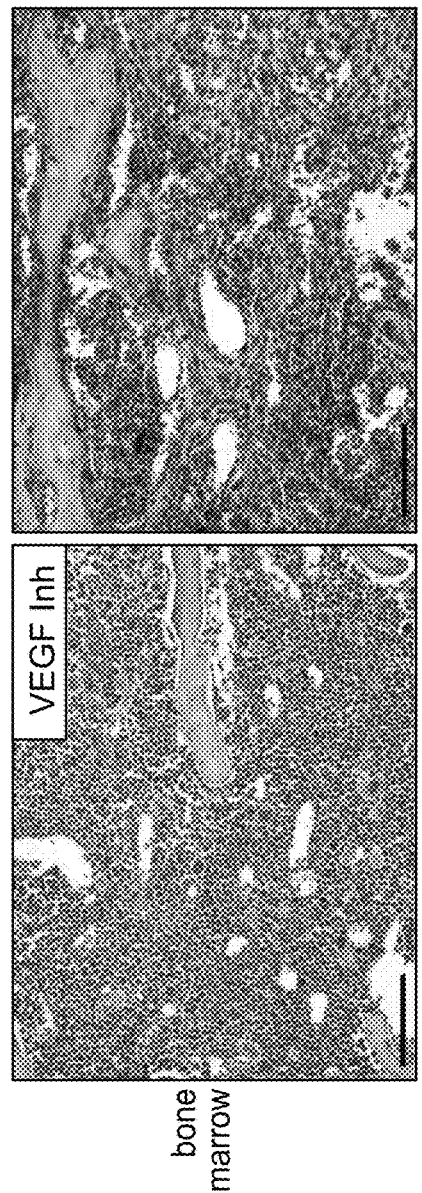

Blockade of the VEGF and PI3K pathways reverse marrow and skin fibrosis in vivo. Encouraged by these findings, we sought to evaluate the efficacy of blocking the PI3K-AKT pathway in c-Jun mediated fibrosis in vivo. Wortmannin, a potent PI3K inhibitor, was systemically administered to mice for 14 days that were induced to express c-Jun two days prior to drug. Remarkably, this treatment resulted in complete suppression of bone marrow and skin fibrosis (FIGS. 6G, H and I). In addition to PI3K-AKT pathway, we also tested the effect of blocking VEGF pathway on c-Jun induced phenotypes both in vitro and in vivo since we found that VEGF was highly expressed in the primary bone marrow-derived adherent cells. As shown in FIGS. 6C, J and K, the specific VEGFR inhibitor PD173074 was able to abolish c-Jun mediated migration in vitro and significantly decreased bone marrow fibrosis but not skin fibrosis in vivo. Any effects on gastroesophageal or bladder were not assessed as the fibrosis in these organs takes longer to develop. Both Rosa26-rtTA control mice were treated with dox and c-Jun-inducible mice were treated with PBS. No fibrosis developed in either control condition in lung or other organs over the same time span. Thus, the PI3K and VEGFR pathways are critical mediators of c-Jun-induced fibrosis in mice and may be also involved in the development of human fibrosing conditions. We note that a recent study showed clinical benefit to idiopathic pulmonary fibrosis patients of VEGFR/FGFR/PDGFR pathway inhibition.

Pro-phagocytotic anti-CD47 treatment reduces fibrosis in vivo. As briefly mentioned above, we had noticed the prominent appearance of infiltrating macrophages in lung fibrosis, both in patient biopsies and in c-Jun-induced mice (FIG. 2A, 4B). These macrophages are surrounding pathogenic fibroblasts expressing the anti-phagocytotic CD47 signal (FIG. 2A,E). This pattern was reminiscent of peritumor macrophages surrounding CD47+ cancer cells and raised the question whether blocking the CD47 signal may stimulate phagocytosis of pathogenic fibroblasts by these infiltrating macrophages. Anti-CD47 antibodies have been shown to eliminate various human cancer cells in different preclinical models but elimination of non-transformed normal cells have not been observed yet. To evaluate whether macrophages could be stimulated to phagocytose fibroblasts, we first tested the effect of blocking anti-CD47 antibodies in vitro. We co-cultured primary mouse macrophages with c-Jun induced primary fibroblasts and observed that in the presence of anti-CD47 antibodies the percentage of phagocytosed fibroblasts was indeed significantly increased (FIG. 6D). These compelling results prompted us to assess the effects of CD47 antibody treatment in our lung-restricted c-Jun fibrosis model. Indeed, daily intraperitoneal injections for 21 days with an anti CD47 antibody substantially reduced fibrosis (FIG. 6E, F). Most importantly, animals administered anti-CD47 antibody treatment survived longer than control group and their lung function was significantly improved as indicated by normalized carbon monoxide diffusion. These data suggest that macrophages can eliminate even non-transformed cells that contribute to disease formation when anti-phagocytotic stimuli are blocked.

Figure 7A:
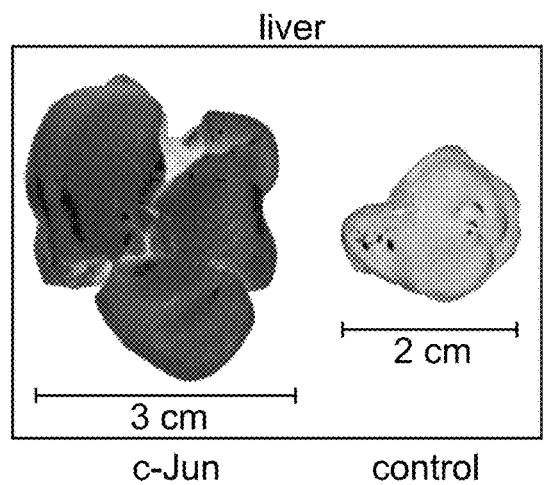
Figure 7B:
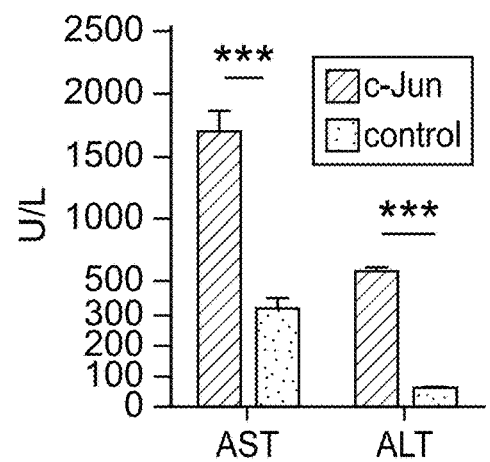
Figure 7C:
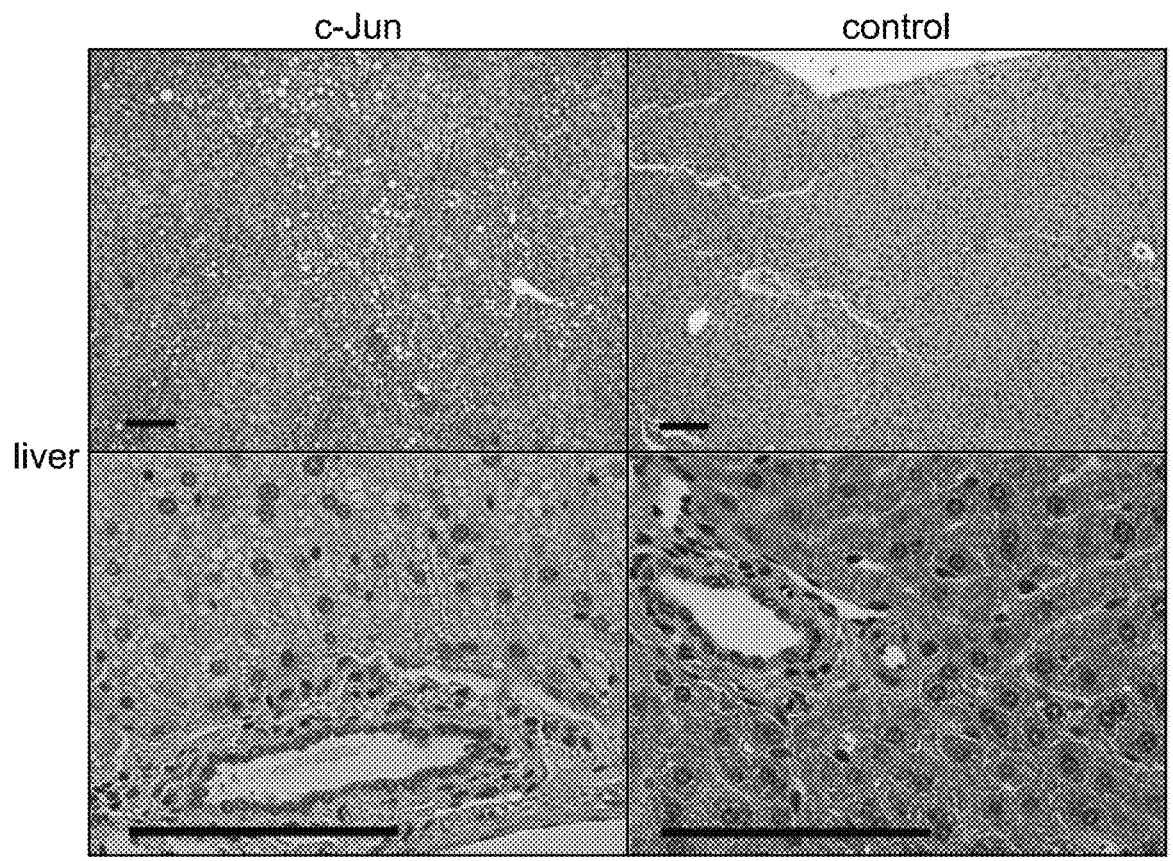
Figure 7E:
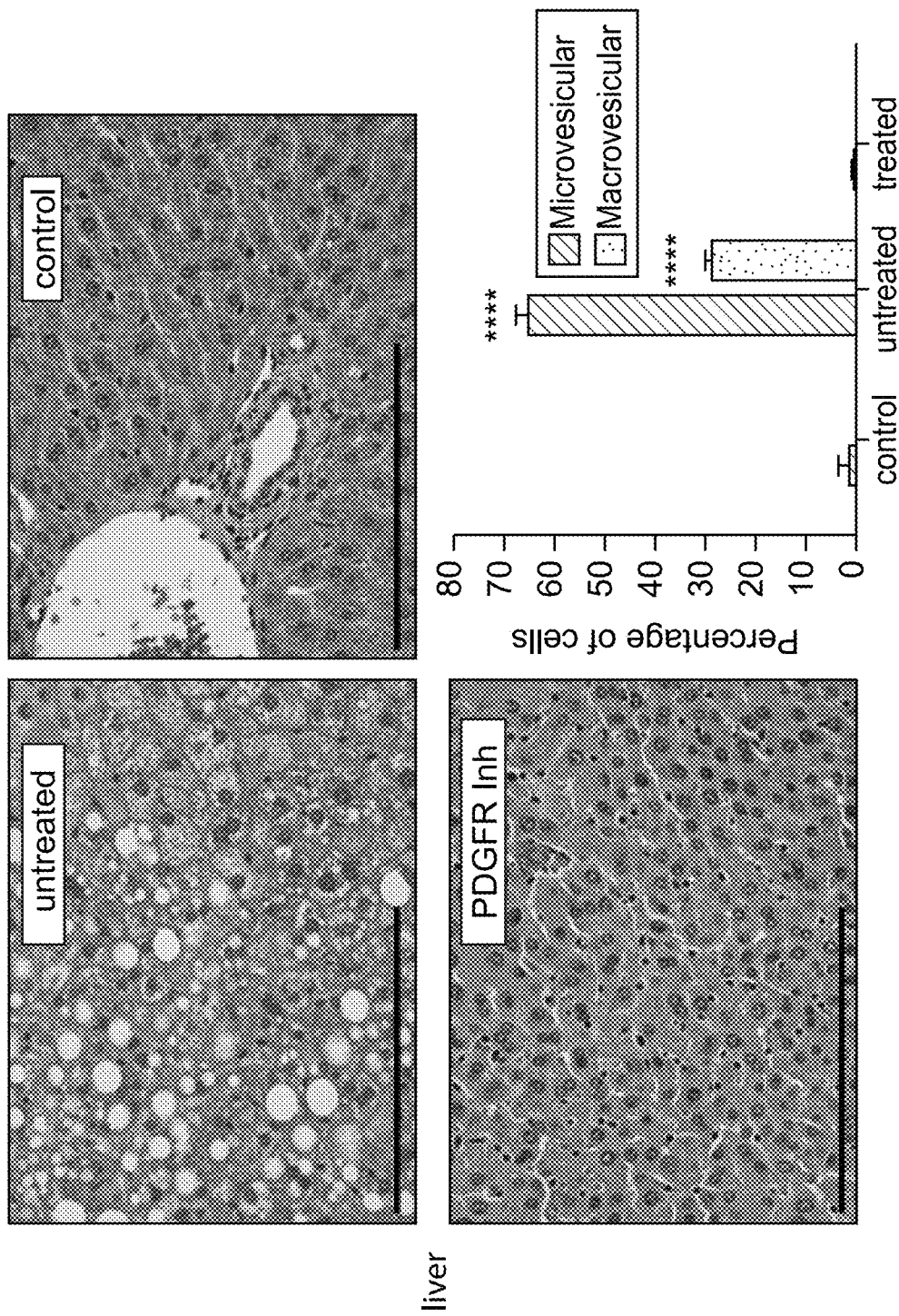
Figure 8A:
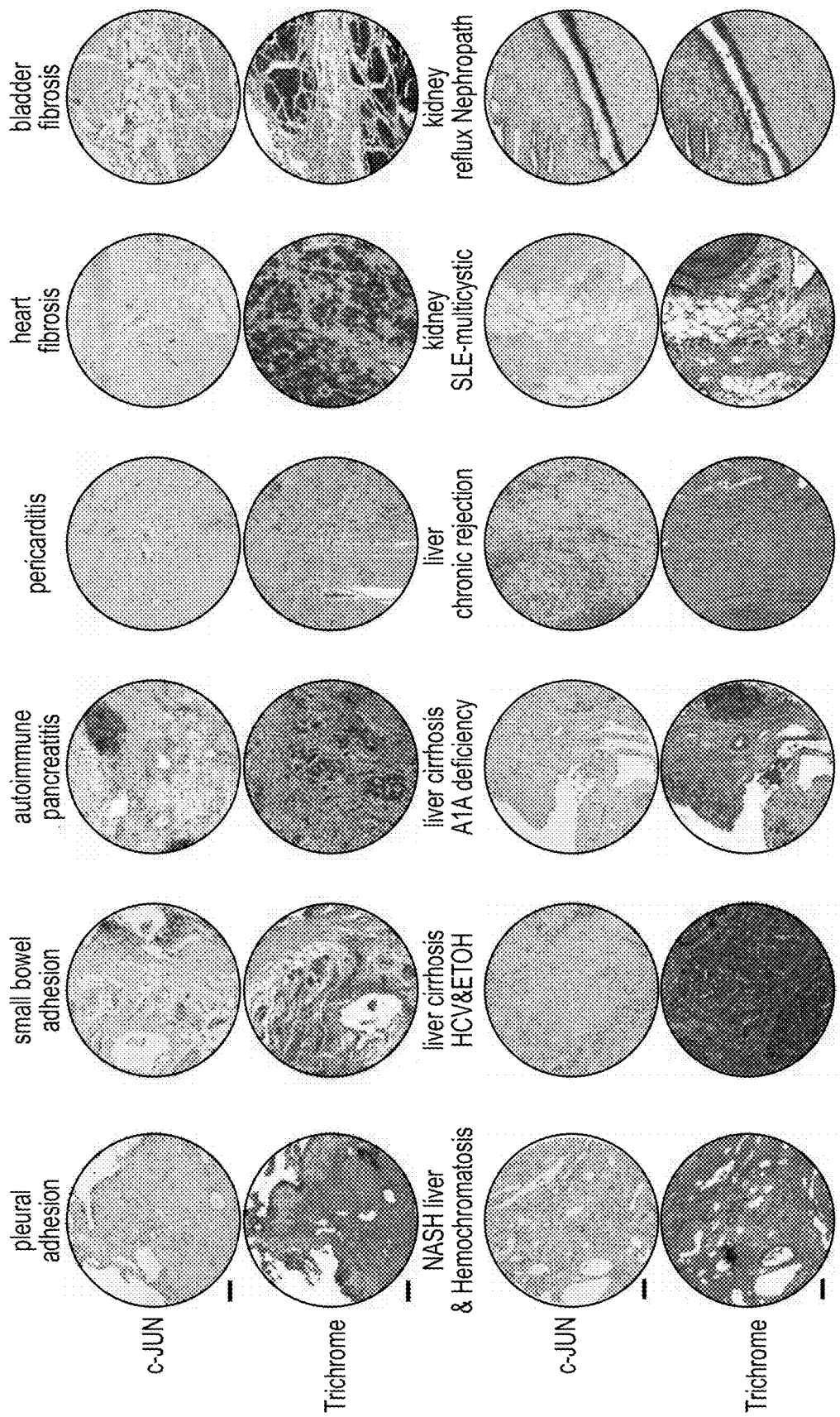
FIG. 8A-8E. The expression pattern of AP1 family in different fibrosing conditions.
Figure 8B:
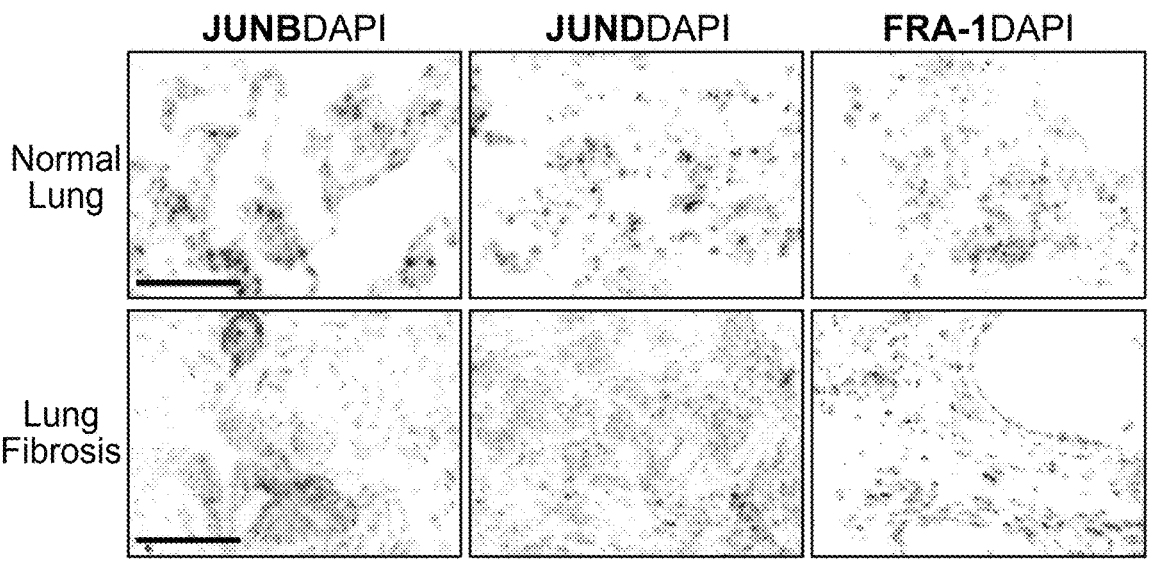
Figure 8C:
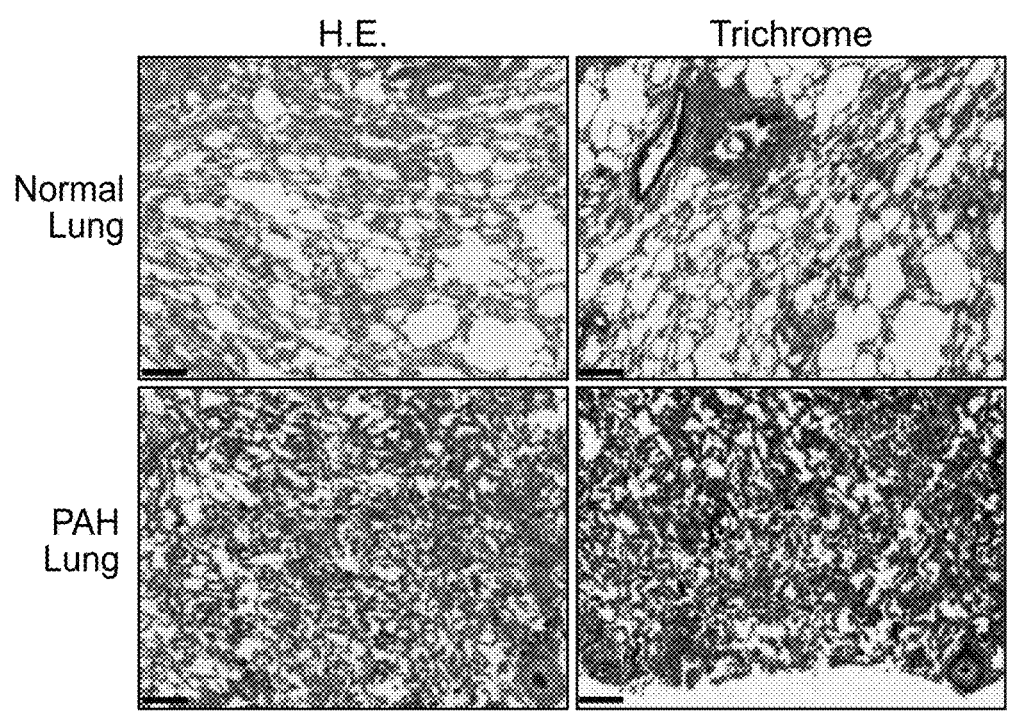
Figure 8D:
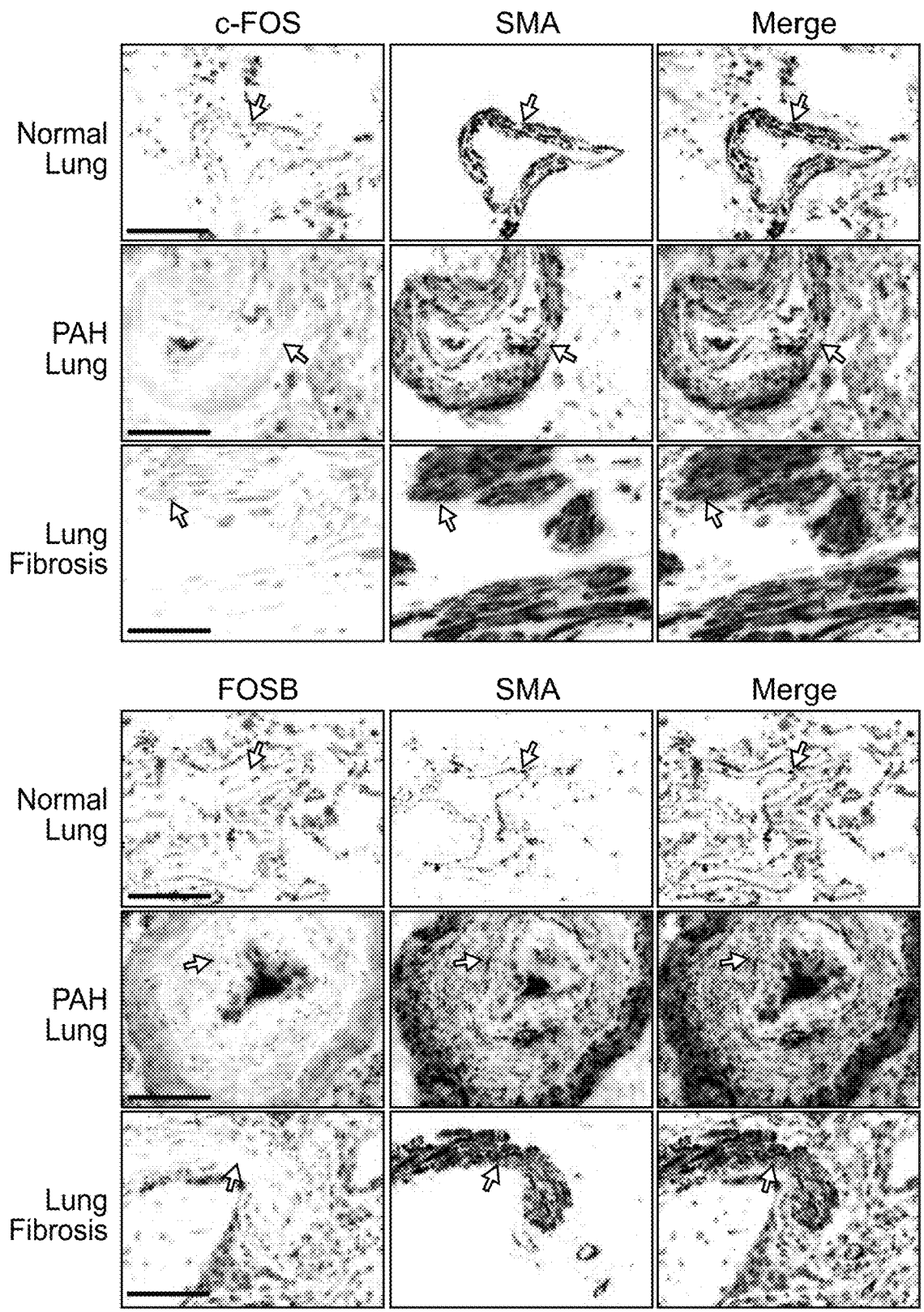
Figure 8E:
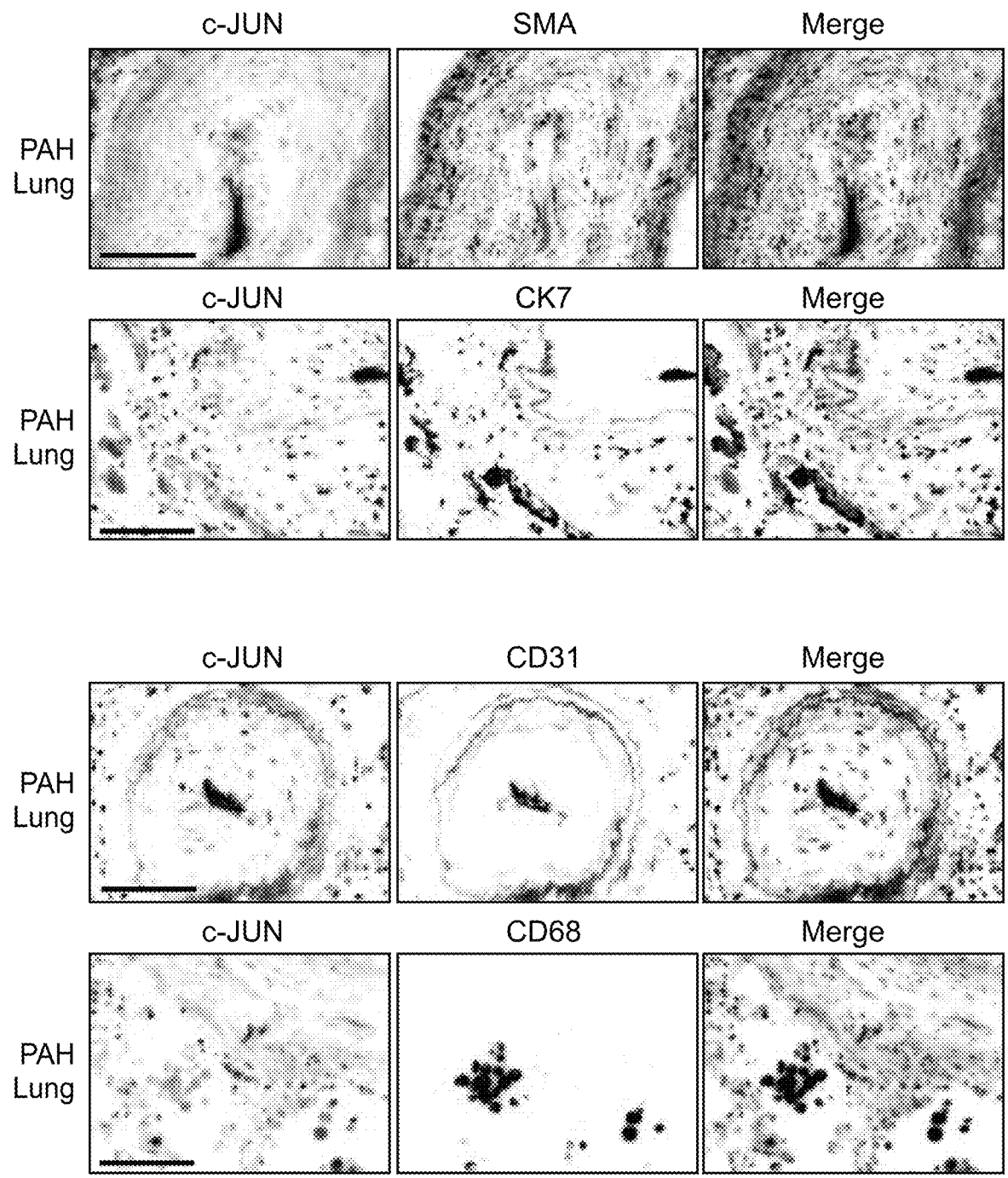
Figure 10A:
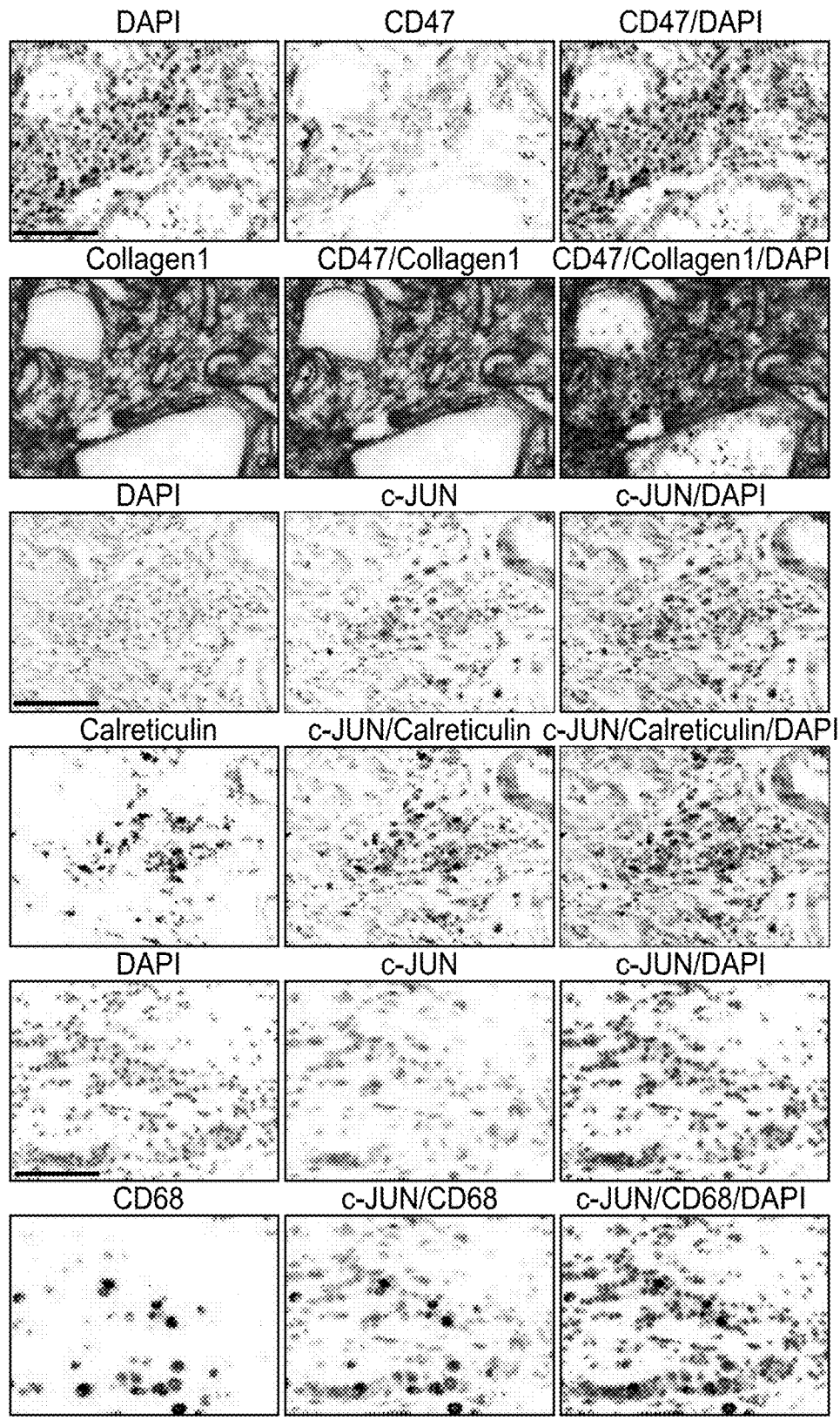
FIG. 10A-10B. Don't eat me signals CD47 and calreticulin are expressed in fibrosis plaques in lung fibrosis.
Figure 10B:
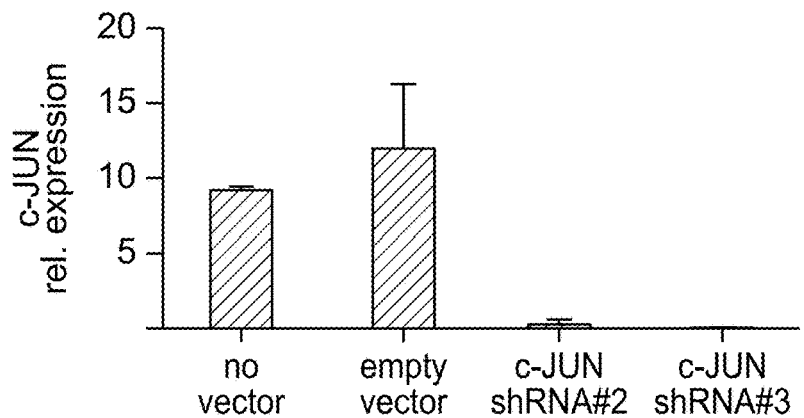
Figure 11A:
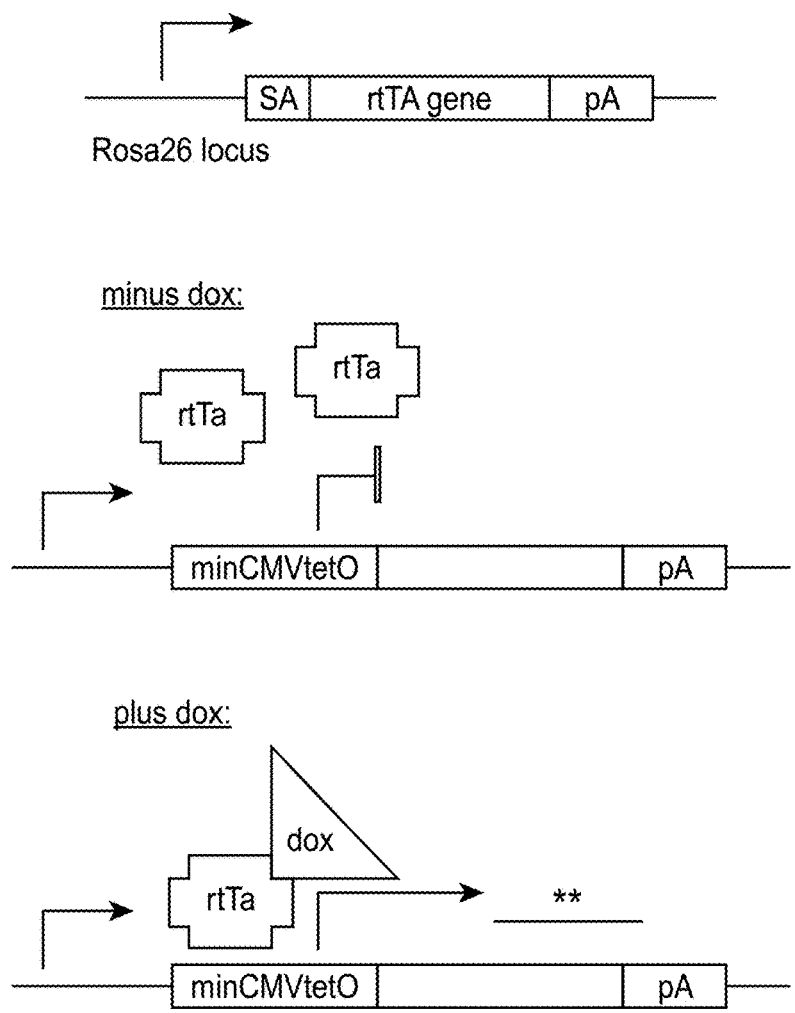
FIG. 11A-11I. c-Jun but not Junb caused skin, visceral and marrow fibrosis in adult mice.
Figure 11B:
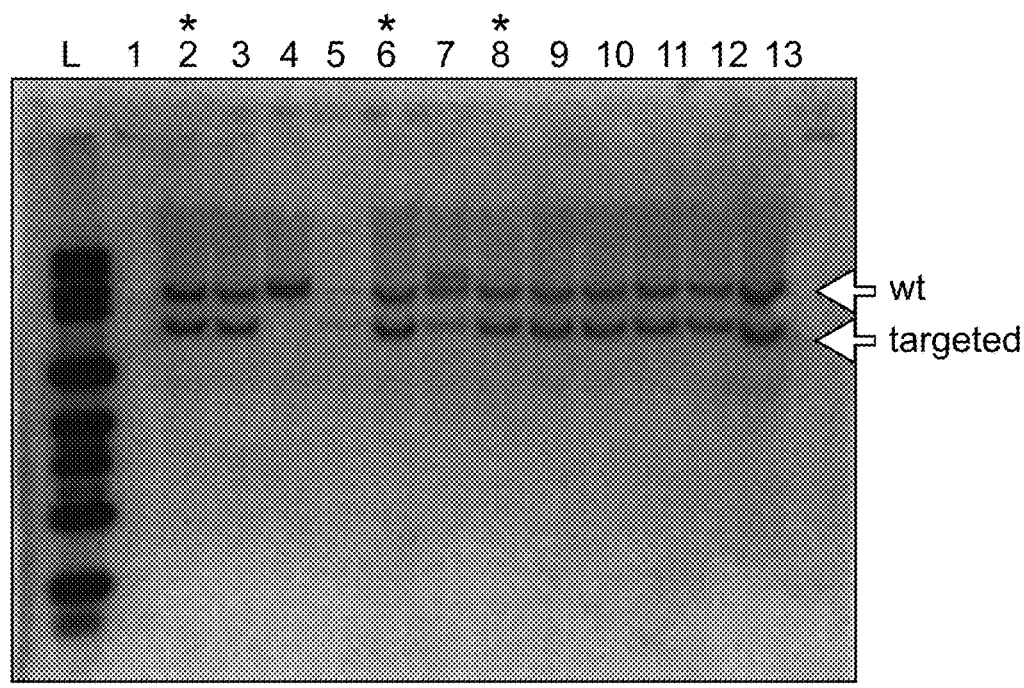
Figure 11C:
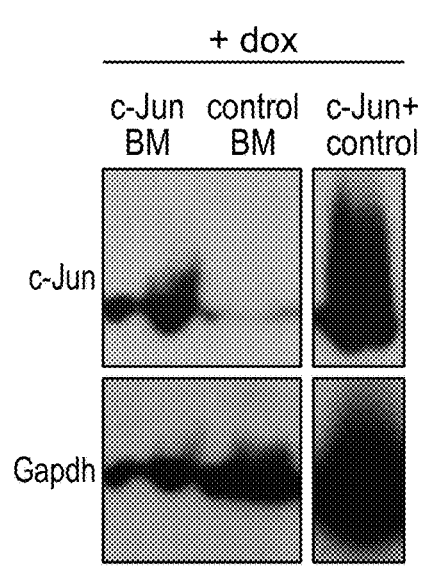
Figure 11D:
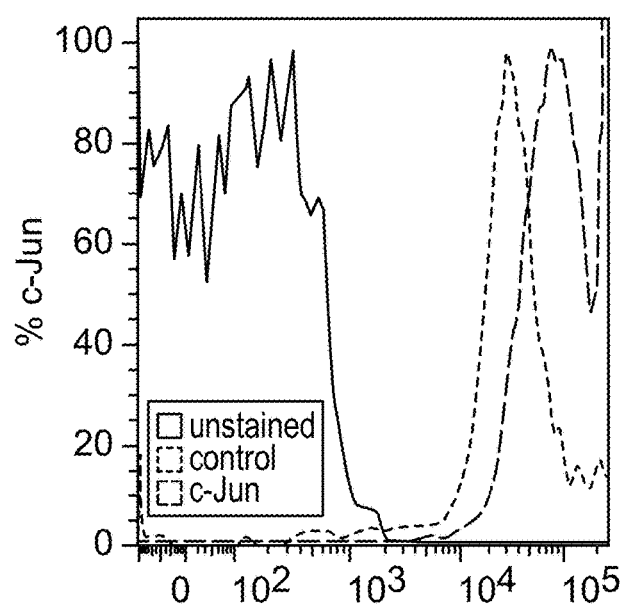
Figure 11E:
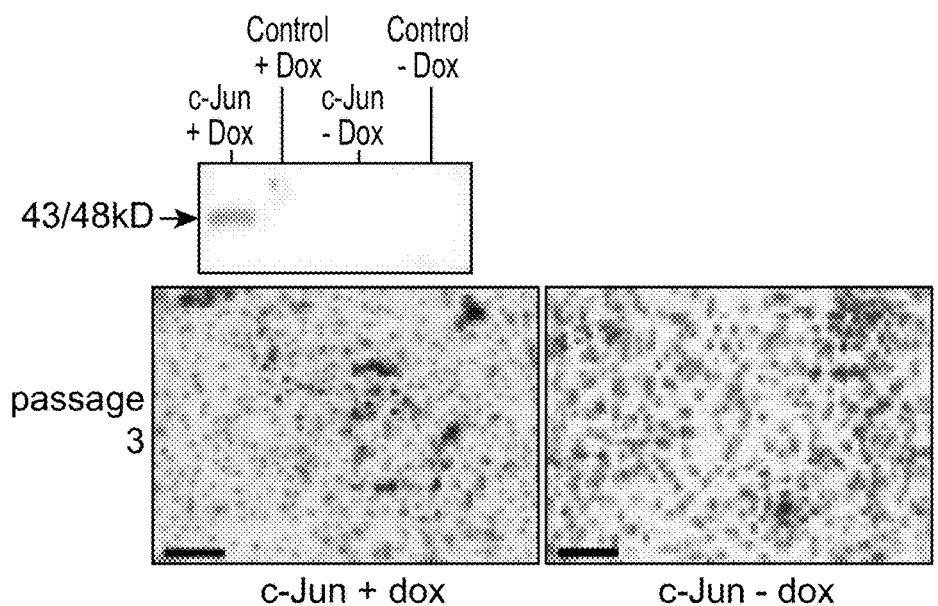
Figure 11F:
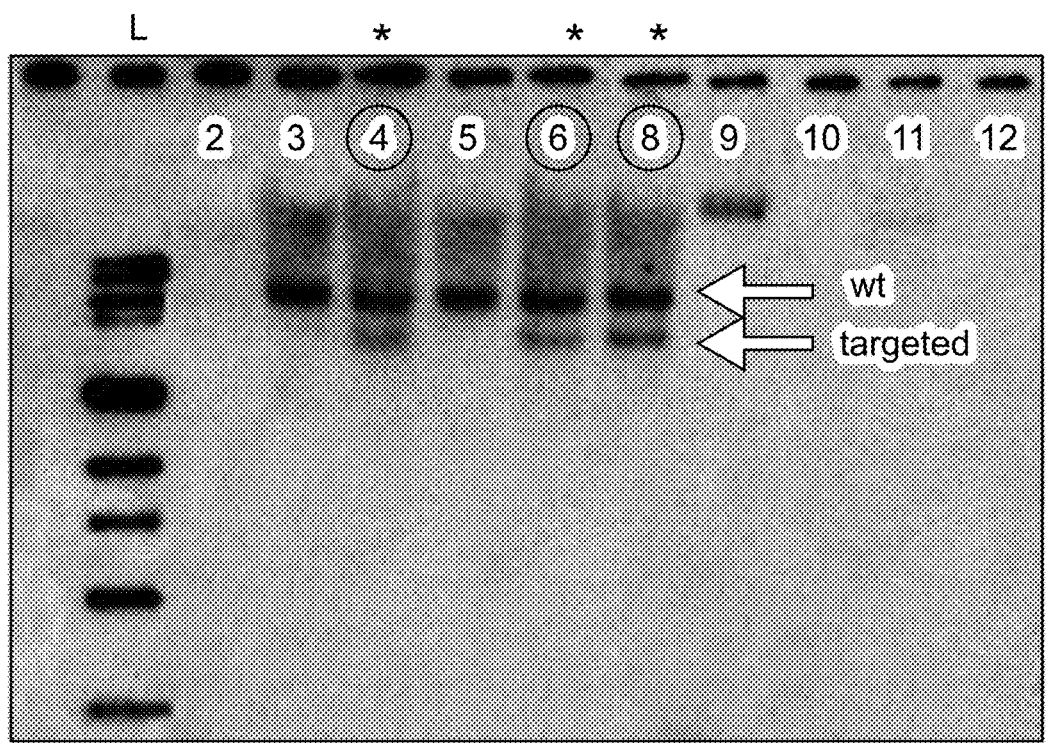
Figure 11I:
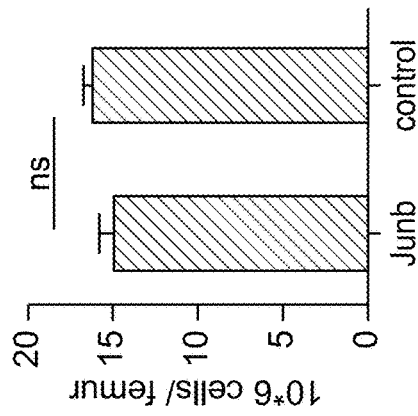
Figure 11G:
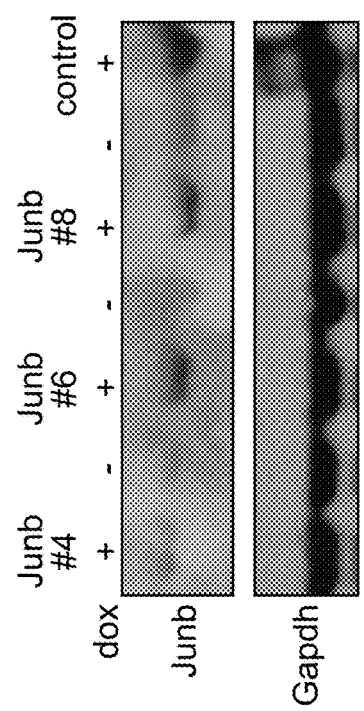
Figure 11H:
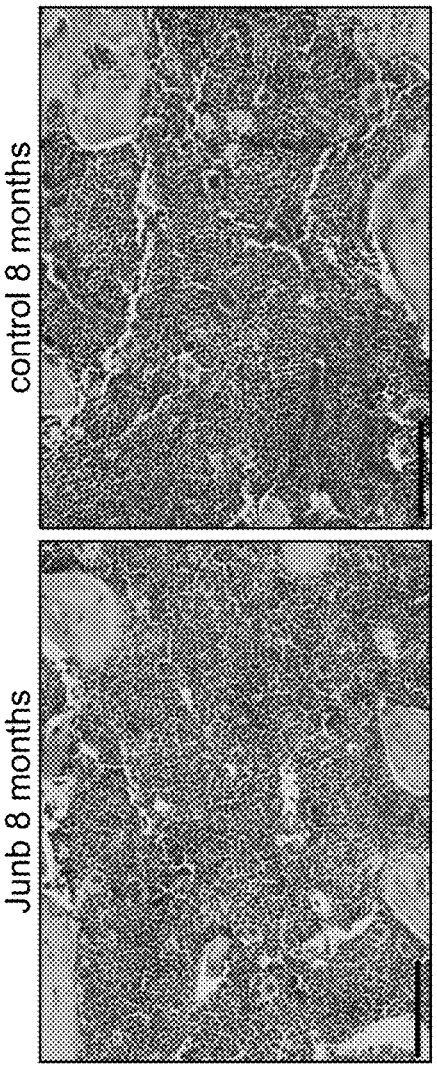
Figure 12A:
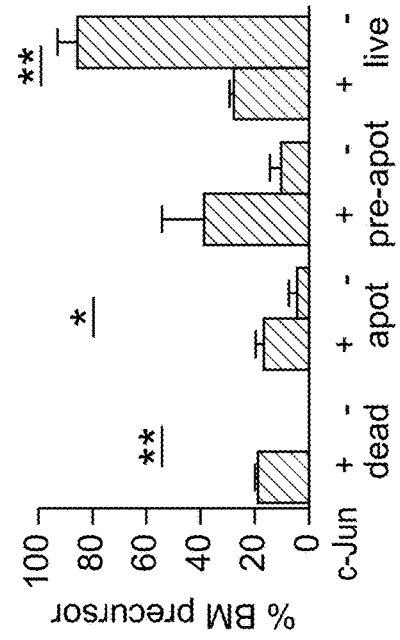
FIG. 12A-12F. No signs of fibrogenesis in various control conditions.
Figure 12B:
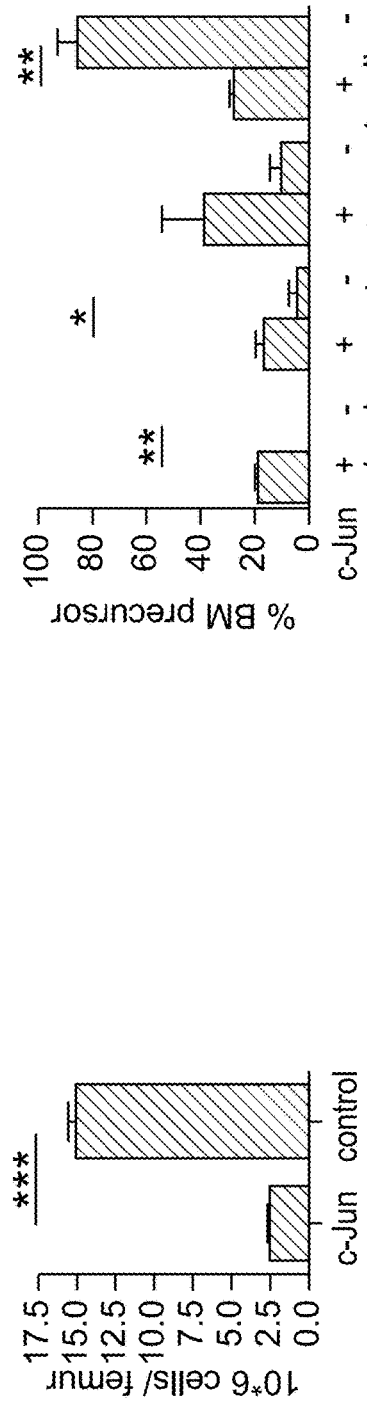
Figure 12C:
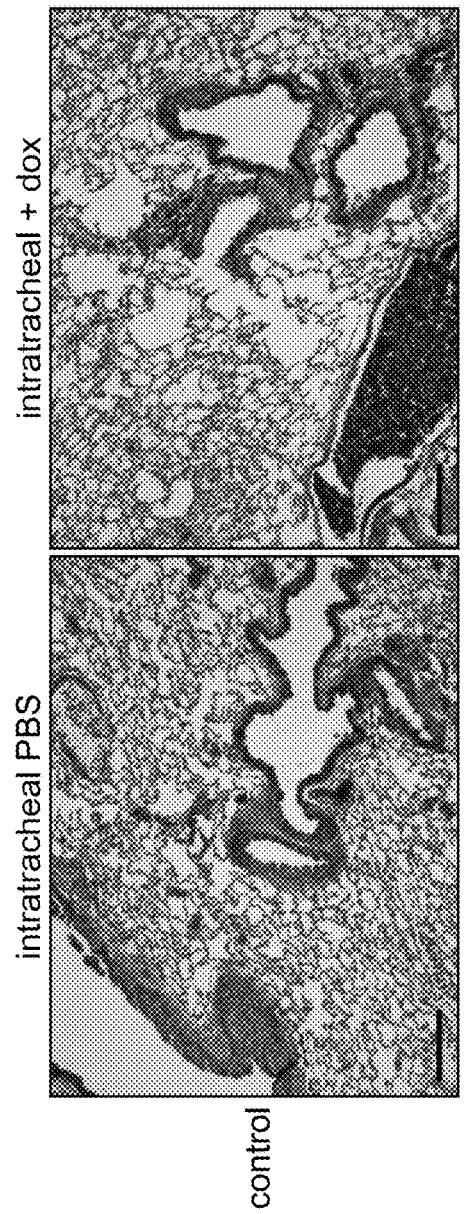
Figure 12D:
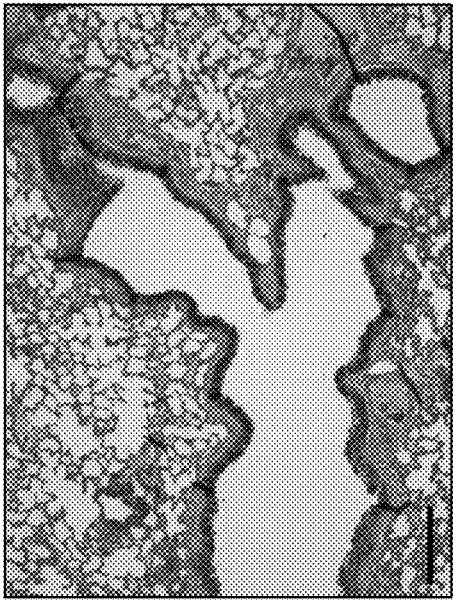
Figure 12E:
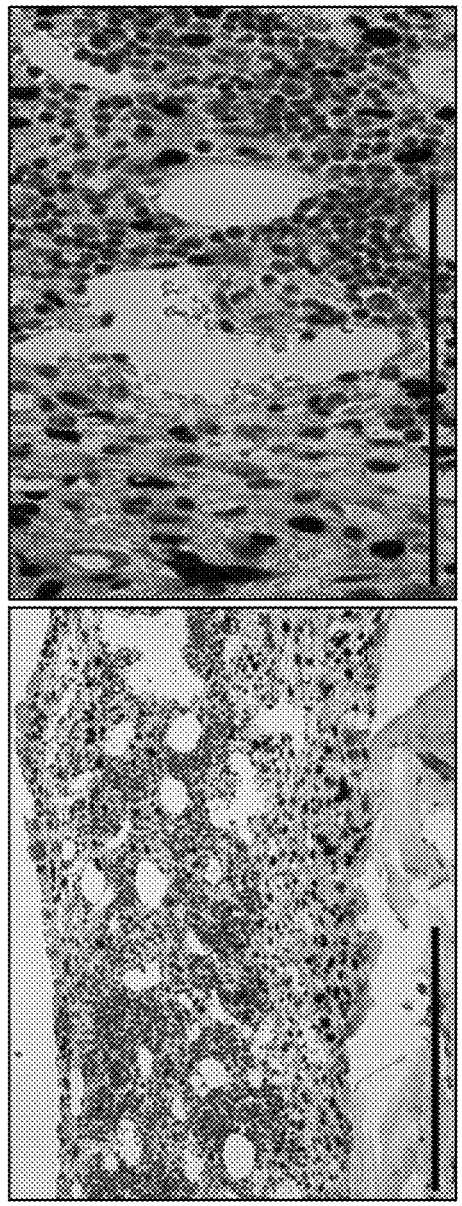
Figure 12F:
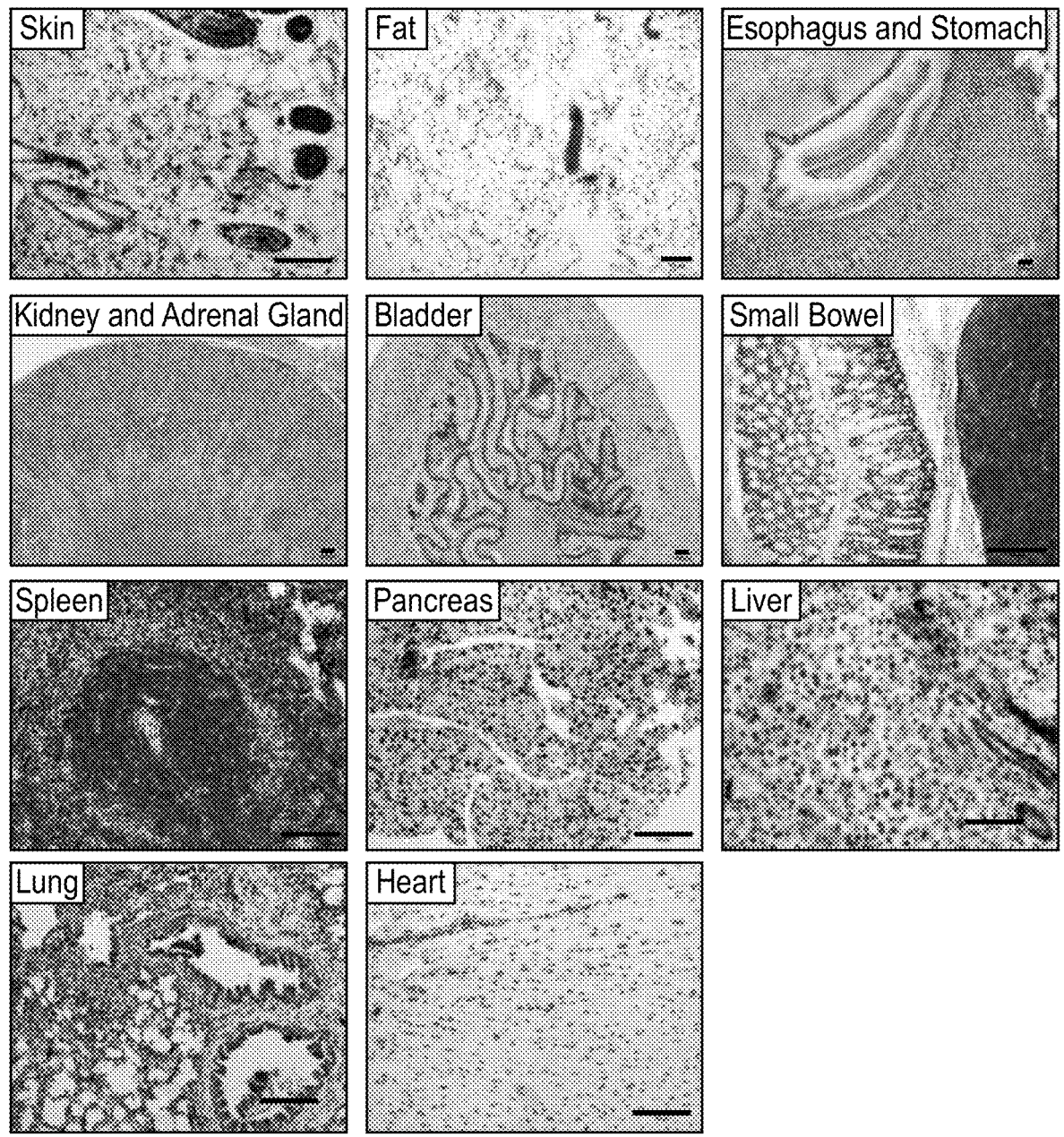
Figure 13B:
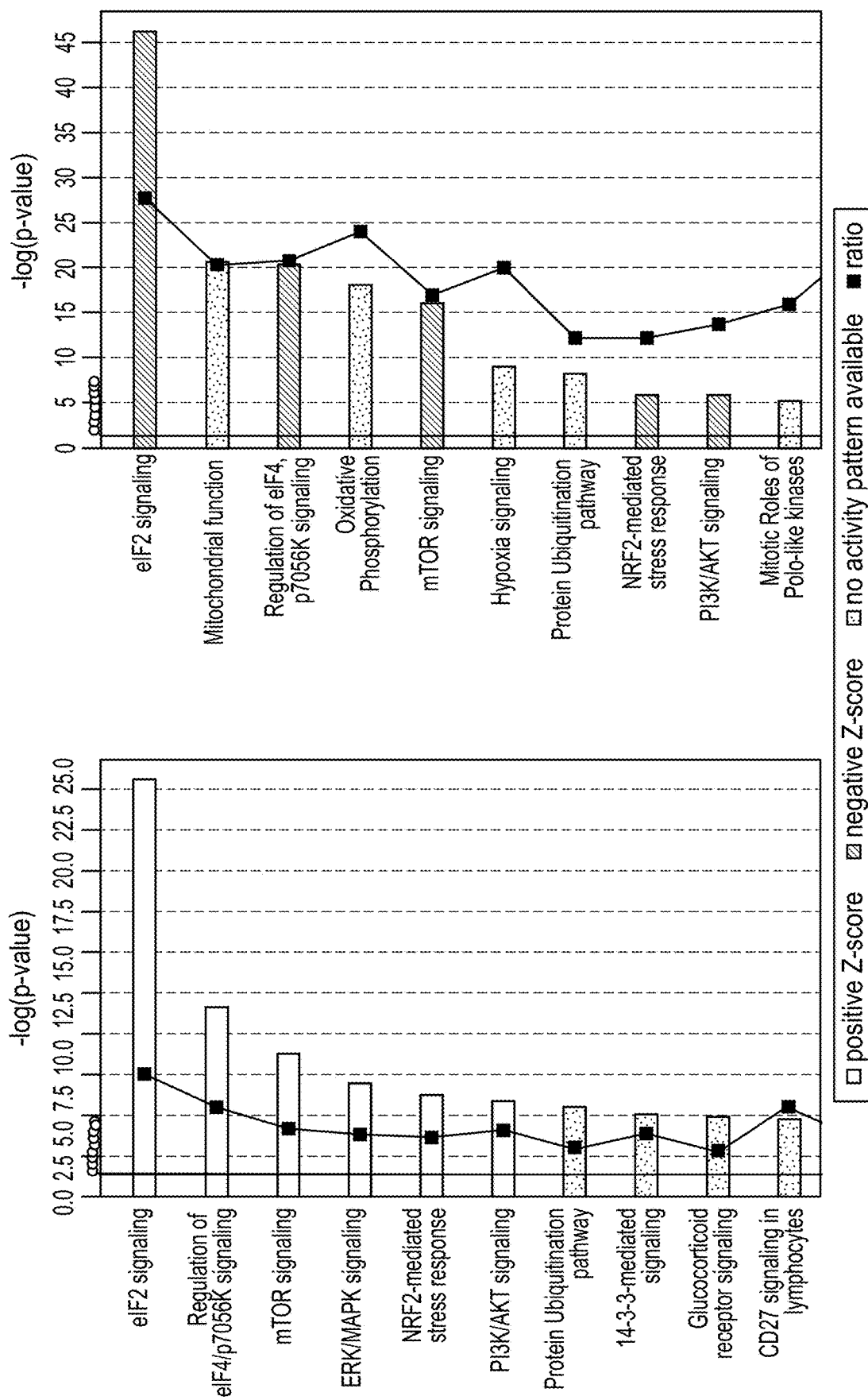
Figure 13C:
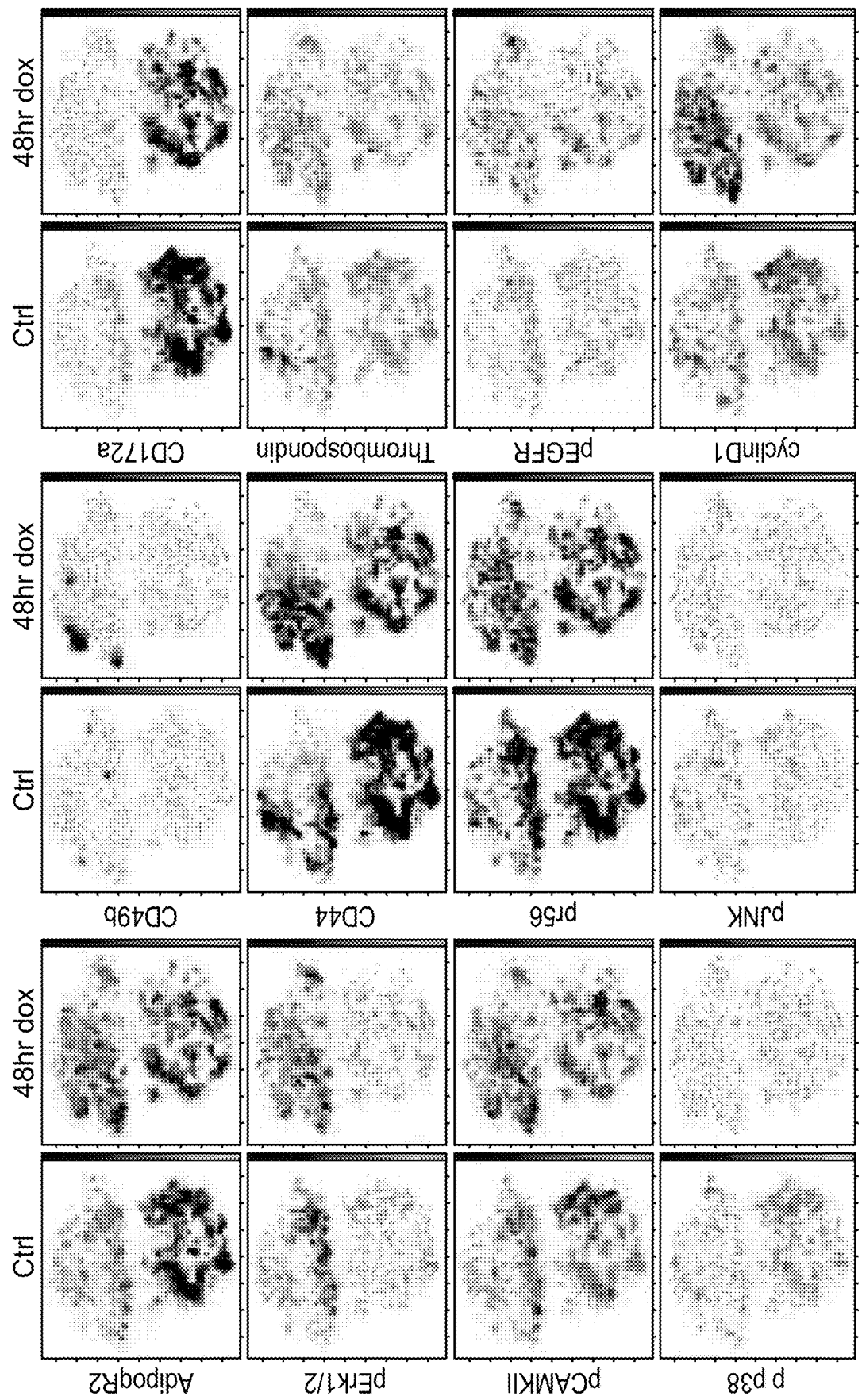
Figure 13C:
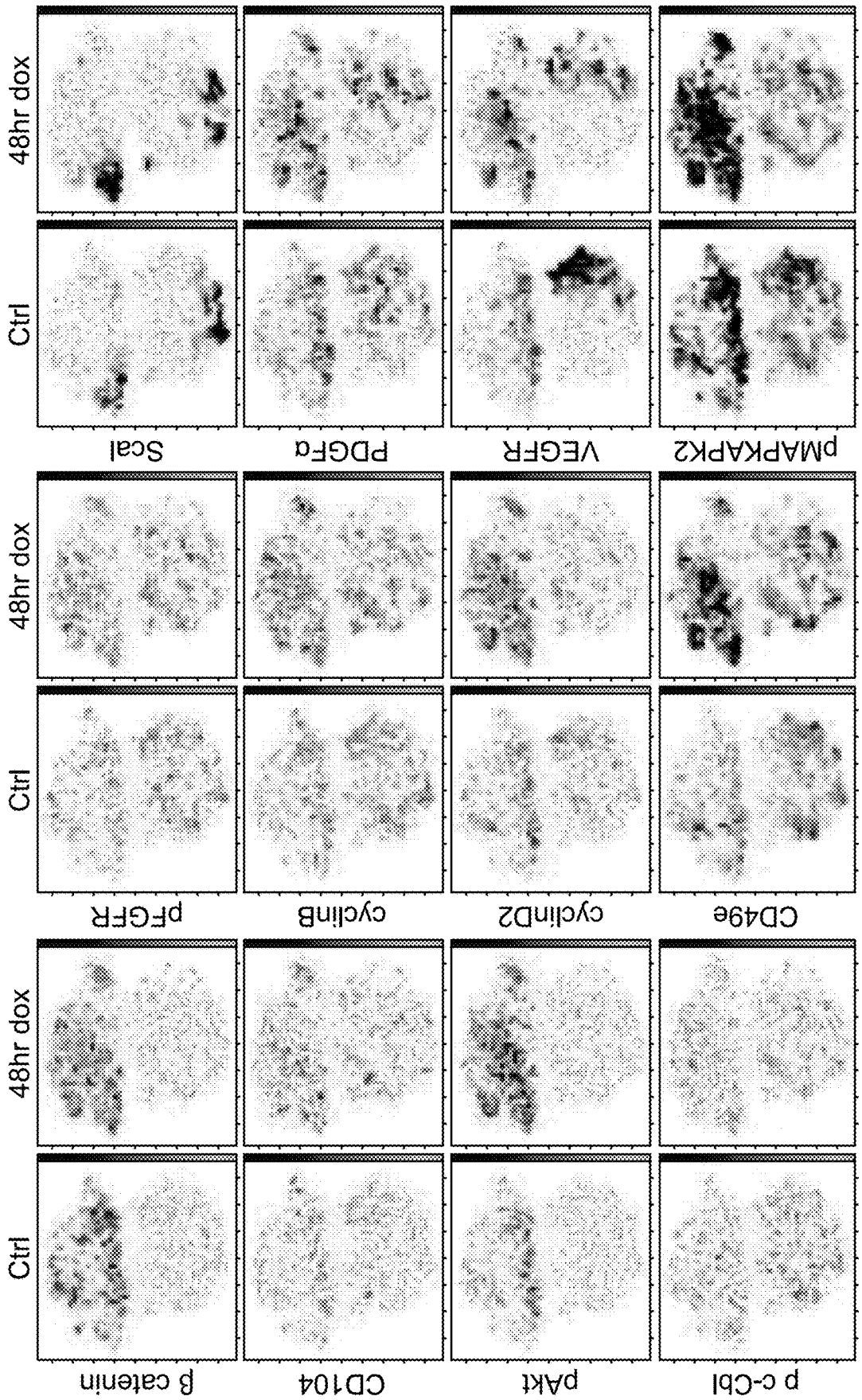
Figure 13C:
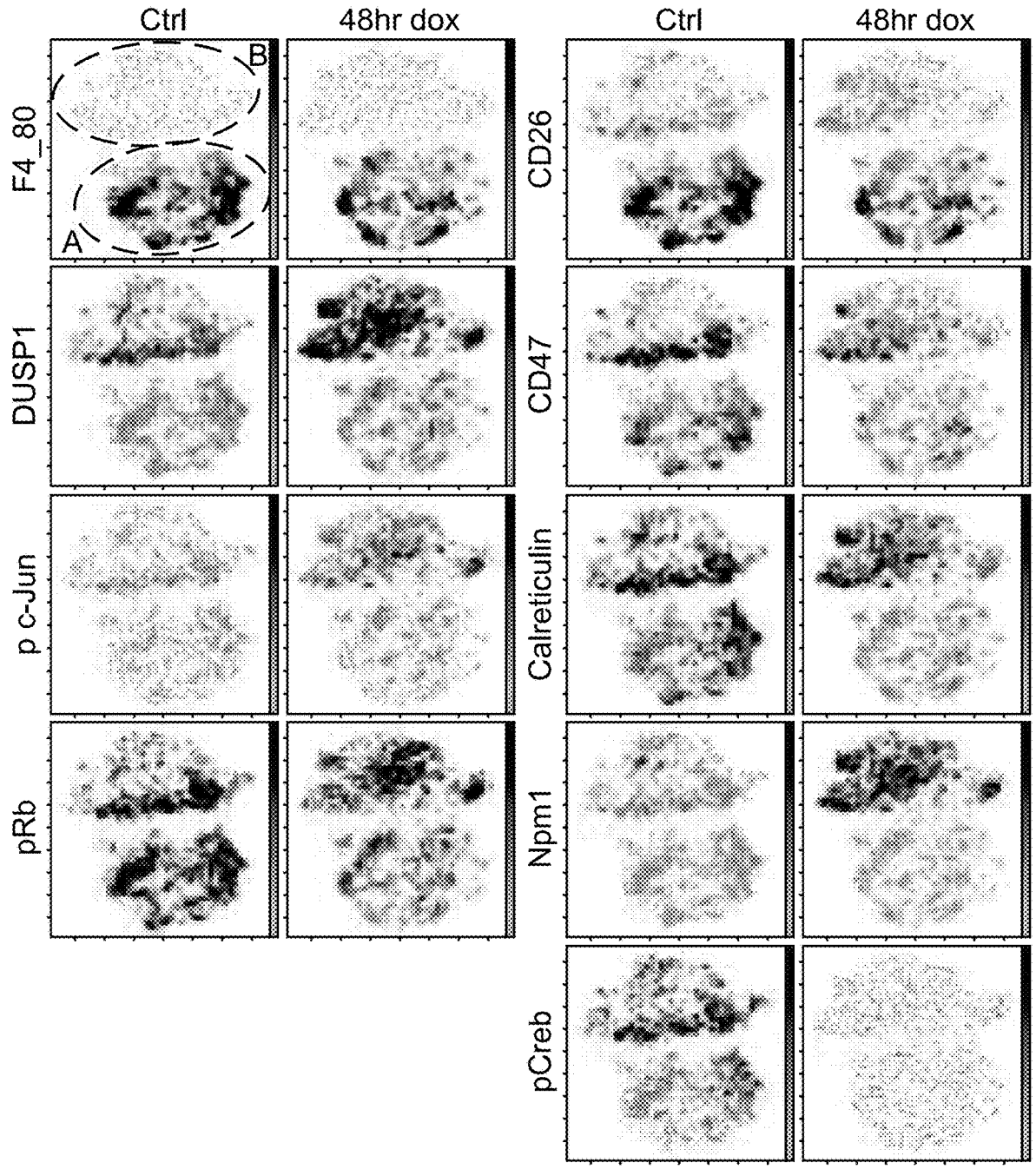
Figure 13D:
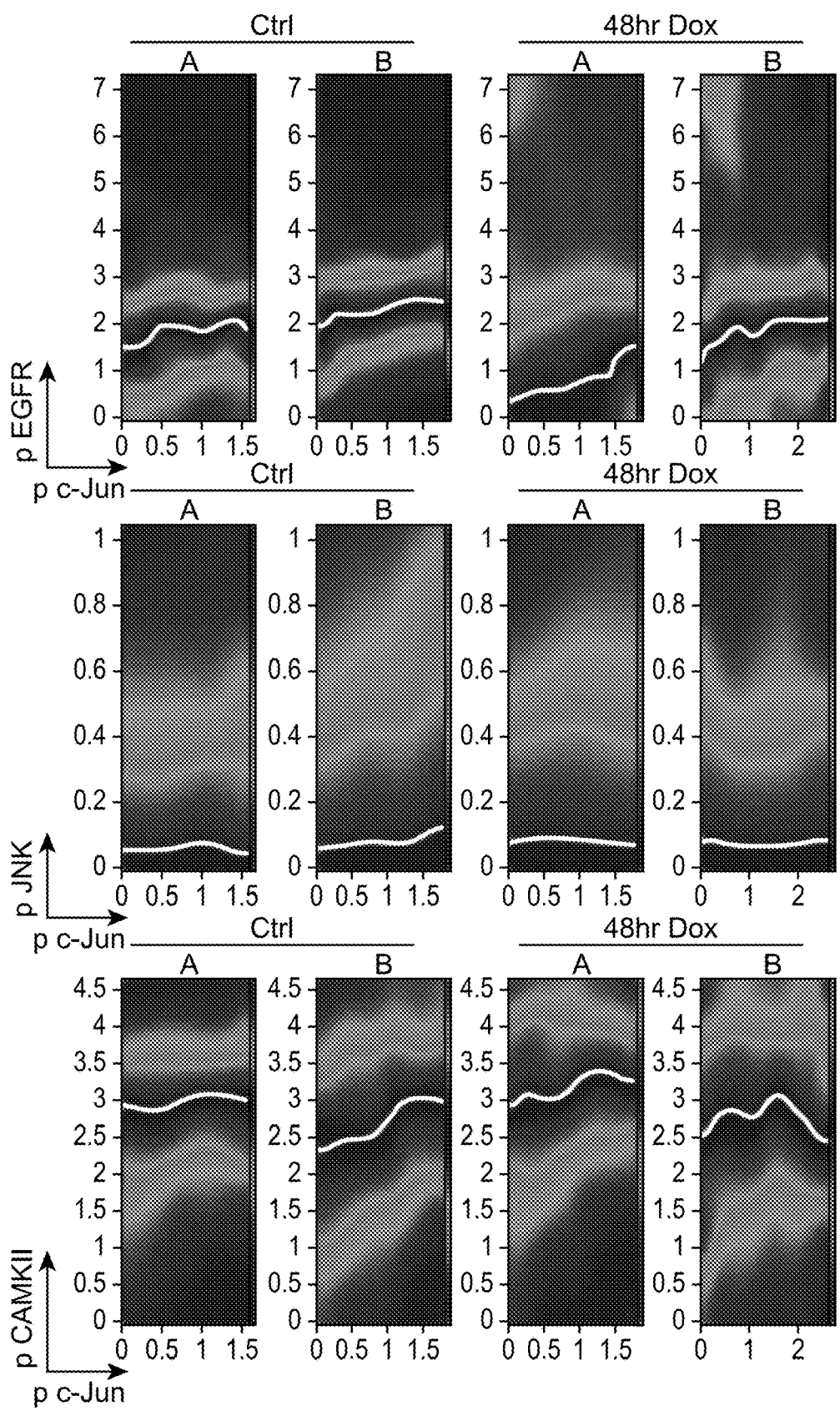
Figure 13D:
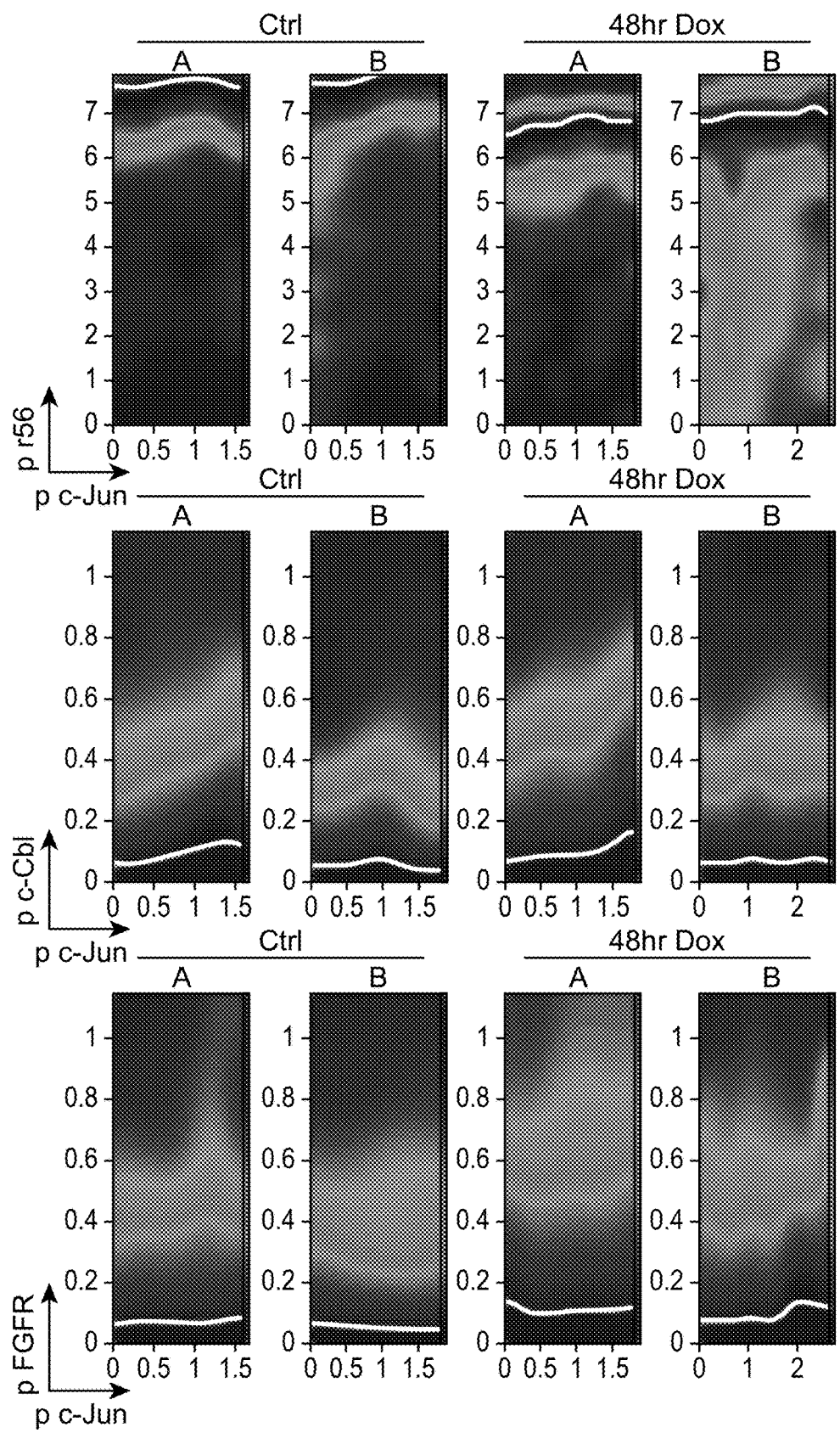
Figure 13D:
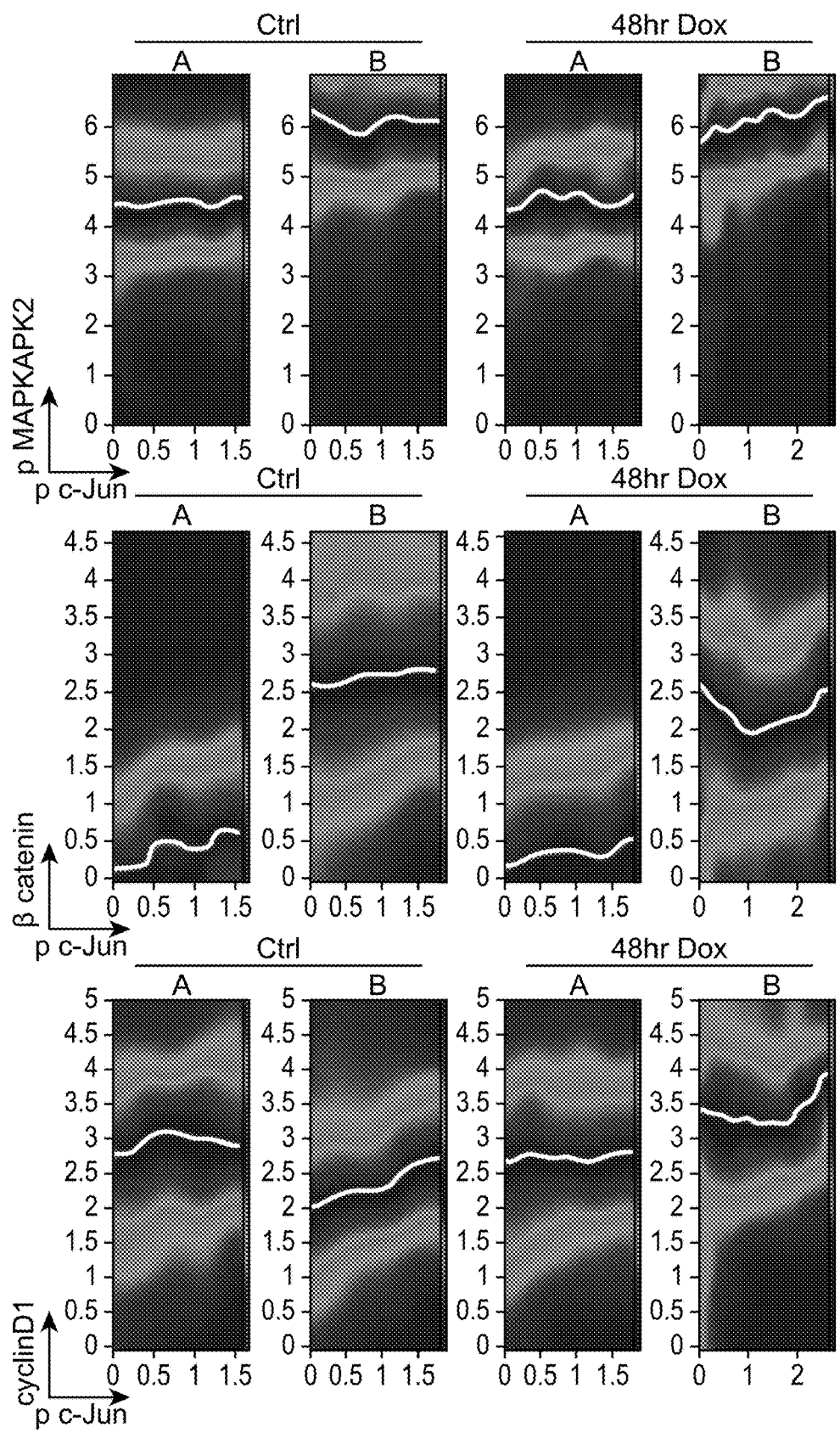
Figure 13D:
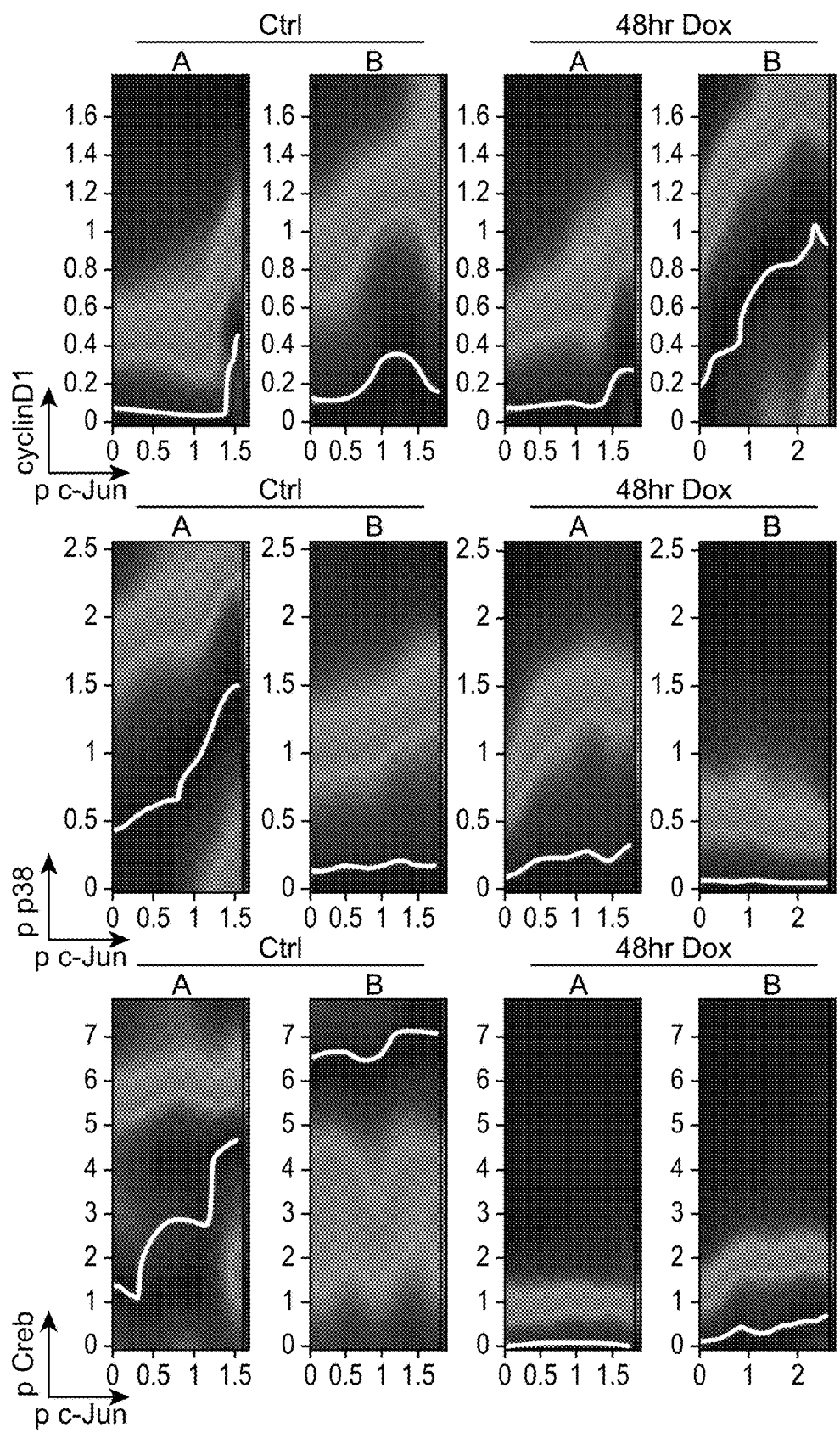
Figure 13D:
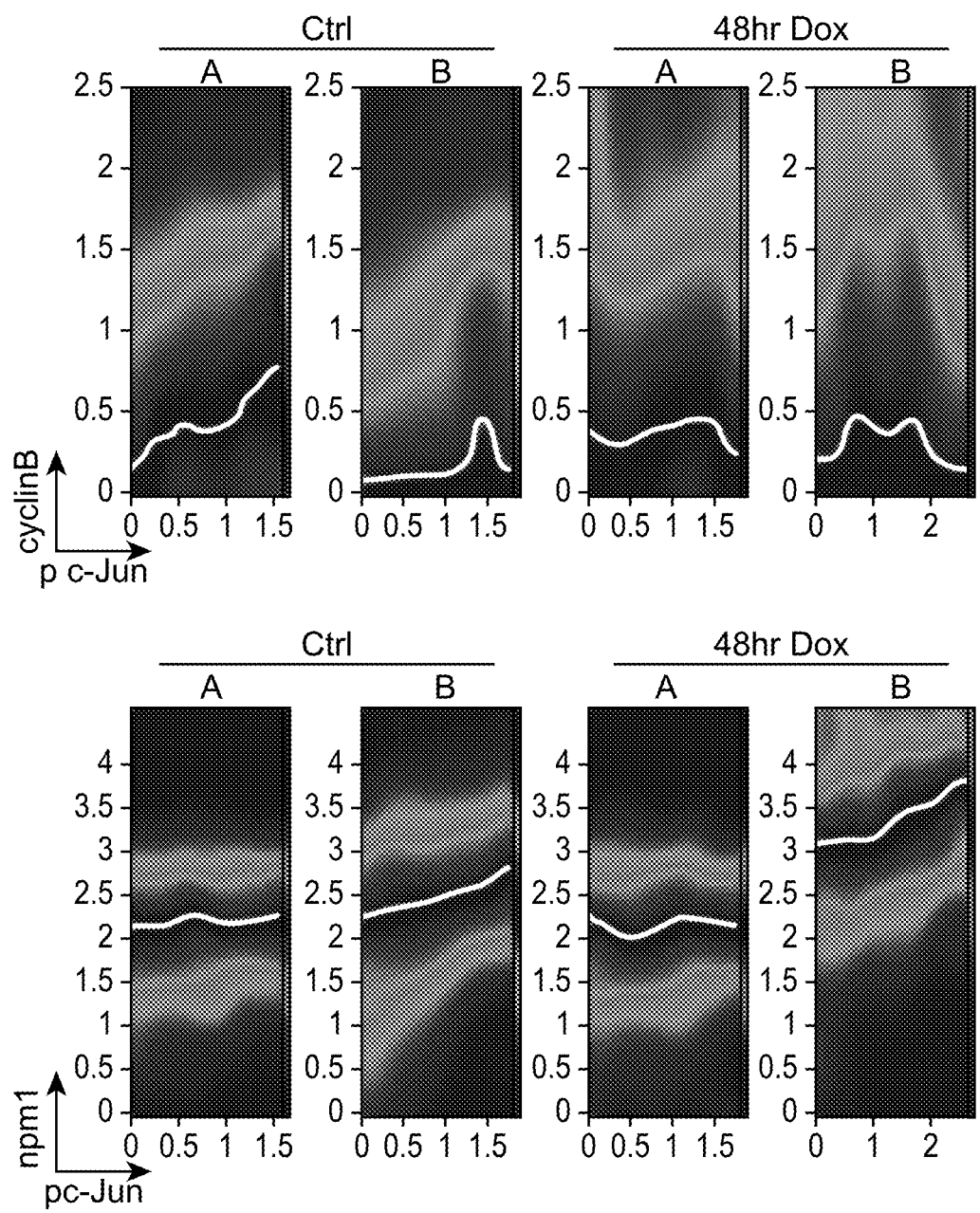
Figure 14:
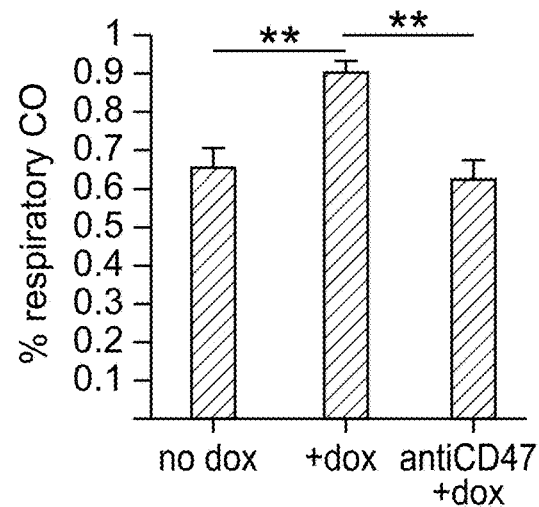
FIG. 14. Lung-specific c-Jun induction resulted in an increased percentage of respiratory CO or the equivalent of a decreased CO diffusion and CD47 antibody treatment normalized CO diffusion in the lung. Data (mean+/−s.e.m.) represent four replicates and two independent experiments; ** $P<0.01$; Student's paired t-test.

Development of steatohepatosis-like alterations following c-Jun induction. Steatohepatosis is considered a precursor condition of full blown liver cirrhosis/fibrosis. Indeed, when analyzed 7-10 days upon systemic c-Jun induction, we noticed that the livers were pale and 5-fold enlarged (FIG. 7A). Blood chemistry revealed dramatically increased liver enzymes; with aspartate aminotransferase (AST) and alanine aminotransferase (ALT) levels 6-fold and 11-fold above normal values, respectively (FIG. 7B). Histomorphologic analysis demonstrated an accumulation of small and large vacuoles within individual hepatocytes but no cholestasis or fibrosis (FIG. 7C). An oil-red O stain highlighted the intracellular lipid droplets and we quantified them at 60% micro- and 40% macrovesicular changes in c-Jun induced livers but only minimal microvesicular changes<5% in non-induced controls. These findings are compatible with fatty liver changes (FIG. 7D). A recent report showed similar liver changes in mice mediated by distinct AP1 dimers, however, unlike our findings, the steatohepatic abnormalities required liver injury (Hasenfuss et al., 2014). Additional blood chemistry studies for alkaline phosphatase and GGT, creatinin and BUN enzymes excluded biliary disease and kidney failure as alternative causes for increased AST and ALT levels but demonstrated the presence of metabolic acidosis indicating steatohepatosis-induced liver failure which is the likely cause of death of systemically c-Jun induced mice. We then treated c-Jun animals which had established fatty liver changes after being induced with doxycycline for 28 days with a PDGFR inhibitor and discovered that micro and macrovesicular steatosis is fully reversable in these animals (FIG. 7E) by blockage of the PDGFR pathway.

Discussion

Here, we report that c-JUN, a well-characterized AP1 transcription factor, is expressed in pathogenic fibroblasts of patients with many different fibrosing diseases. We found decreased proliferation of patient fibroblasts from fibrotic lungs after knockdown of c-JUN. We detected activated c-JUN and AKT as well as upregulation of CD47 expression in vivo in endstage fibrosis lungs. We further showed that c-Jun can induce rapid and widespread fibrosis in all organs in mice and is also expressed in fibrotic areas of established skin-wound healing and abdominal adhesion models in wildtype mice. c-JUN is widely expressed in skin epithelium and many other epithelial cells, but not highly in stromal cells. c-JUN is also part of the acute phase response cascade, has a role in bone formation, a reputation as an oncogene and its upregulation has been shown in various cancers. While c-JUN's role in cell cycle promotion has been well established primarily in vitro, we observed a striking cell context-dependent fibrotic response in vivo. Despite ubiquitous c-Jun induction we observed primarily fibrotic changes indicating that the pro-proliferative and pro-migratory effects of c-Jun require the specific cellular context of tissue fibroblasts. Systemic induction of c-Jun in hematopoietic precursors caused rapid apoptosis, induction in the liver a pronounced hepatosteatosis. This unique c-Jun responsiveness appears to be shared among fibroblasts of many different tissues although fibroblasts are considered highly heterogeneous and tissue-specific. The fibrogenic response in multiple tissues and organs also contrasts with previously developed fibrosis models, suggesting that induction of c-Jun could be a common molecular mechanism across different human fibrotic conditions.

We further provide evidence that the transcription factor c-Jun, which is a downstream target of MAPK signaling cascades, can itself rewire and stabilize a specific pattern of multiple signaling pathways. We assume that the remodeling of signaling pathways will be different in different cell types leading to the opposing cell biological effects of c-Jun in different cell types.

Importantly, our mouse model also confirmed the functional relevance of several signaling pathways, some of which were previously associated with fibrosis and were targeted in past clinical trials. This suggests that c-Jun may be a central node controlling these essential pathways. Intriguingly, a recent clinical study suggested efficacy of a combination of small molecule inhibitors targeting three different pathways, VEGF/FGFR/PDGFR. While combination therapy is in principle an attractive strategy, in practice it is difficult to identify the right combination of pathways to target. In particular for clinical trials it is not feasible to evaluate combination therapy in a systematic manner. Our discovery that c-Jun coordinates several signaling pathways leading to fibrosis in vivo provides a unique opportunity to identify all relevant signaling pathways and predict the most effective therapeutic drug combinations. Moreover, it may be possible to develop therapeutic strategies interfering with the activity of c-Jun directly. This would eliminate the need to search for the most effective combination by eliminating the key disease-driving element.

Several other mouse models have been established previously and have served to gain important insight into some specific aspects of disease. The most widely used model is a bleomycin-induced lung fibrosis isolated or in combination with the genetic model of Marfan syndrom. This model suggested the involvement of the TGFBR pathway in fibrosis, which we could confirm to also play a role in our c-Jun-induced model. In particular, the genetic model of Marfan syndrome was very instructive regarding the dissection of the contribution of dendritic helper cells towards the pathomechanism of skin and pulmonary fibrosis. Another model system utilizes carbon tetrachloride (CCl4) or bile duct ligation to study fibrosis in the liver which has been shown to be linked to loss or constitutive activation of PDGFR-3 in stellate cells.

Unlike these mouse models, the c-Jun-induced model is a purely genetically driven model. Importantly, it recapitulates many aspects of the respective human disease conditions and is not limited to one organ system (such as only lung or skin) akin to the multi-organ disease of systemic sclerosis. Furthermore, c-Jun is highly expressed in all human fibrotic conditions analyzed and thus in vivo c-Jun induction is likely more physiologically relevant than chemical or infectious conditions which are not involved in the pathogenesis of human disease. We would argue for these reasons that our mouse model will be an important new tool to further dissect the pathomechanisms leading to human disease.

One such new application was our surprising discovery that endogenous macrophages can be exploited to eliminate pathologic fibroblasts. We showed that fibrogenic cells expressed high levels of the self-protective "don't eat me" epitope CD47. It had been shown in various solid cancers and hematopoietic malignancies that blockade of CD47 by antibodies or artificial, high-affinity Sirpα analogs prevent this repressive signal in macrophages leading to their activation and active phagocytosis. The remarkable low toxicity of anti CD47 treatments though suggested that additional alterations in cancer cells are required to induce phagocytosis. Here, we show that this property is not limited to cancer cells as fibrosis was effectively reversed with anti CD47 treatment by elimination of fibroblasts by macrophages. Future studies will have to be conducted to identify the common mechanisms between fibrotic cells and cancer cells that allow effectiveness of the anti CD47 treatment and which other non-cancerous diseases may benefit from such a therapy.

In conclusion, our study revealed the unexpected role of c-Jun as key and selective driver of organ fibrosis in most human fibrotic diseases. Our findings suggest that diverse fibrotic syndromes may have different etiologies but share common pathomechanisms centered around activation of c-Jun. The c-Jun mouse model may well be suitable to further dissect the pathogenesis of all types of pathologic fibrosing conditions and develop new and effective therapies.

Experimental Procedures

General statement regarding human samples and animal studies. Patients' specimens in paraffin were provided by the histopathological archive of the pathology department of Stanford University hospital according to guidelines (IRB11177). Experiments were conducted on c-Jun tetracycline-inducible transgenic mice in accordance with guidelines established by the SU Administrative Panels for Lab Animal Care.

Generation of Tetracycline inducible transgenic mice. The tetracycline-inducible system has been used to generate transgenic mice overexpressing c-Jun and JunB in vivo as described exactly as in Beard et al., 2006. Briefly, it consists of two components, one encoding the tetracycline controllable transactivator (rtTA) and the other consisting of the tetracycline operator minimal promoter (tetOP) driving the gene of interest. We targeted the ColA1 locus that encodes the type I collagen protein and transgenic tetracycline-inducible mice were generated. ES cells carrying both the R26-M2rtTA allele and the flp-in tetO-c-Jun or flp-in tetO-JunB alleles were screened by southern blot and subsequently targeted ES cells injected into blastocysts and viable chimeras generated; alternatively mice were derived by tetraploid embryo complementation. Mice were genotyped by PCR for the presence of both alleles and 6-8 week old mice were treated with doxycycline administered in the drinking water (1 mg/ml) for 7 days up to 36 days and tissues were harvested and analyzed by immunocytochemistry. Transgenic mice that were not exposed to doxycycline as well as mice harboring the rtTA only showed no detectable c-Jun or JunB expression and those were used as controls as indicated.

Bone marrow transplantation. Transplant studies were performed exactly as previously described Wernig et al., 2006. Recipient mice were lethally irradiated with a total dose of 11 Gy, given in two equal fractions 3 hr apart on the day of transplant. Each mouse was transplanted with 1 to $5 \times 10^6$ BM leukocytes obtained from 6-8 week old c-Jun transgenic mice or CD45.1 wildtype mice purchased from Taconic. The hematopoietic parameters of the transplanted mice were assessed 3 weeks post transplant. Donor cell engraftment 3 weeks post-BMT was confirmed by either FACS analysis after staining hemolyzed PB cells with CD45.1-PE and CD45.2-APC. PB cellularity, donor cell engraftment and hematopoietic cell content were reanalyzed 4 weeks post BMT after 1 week on doxycycline as described above.

Parabiosis. Parabiosis surgery was performed exactly as described Wagers et al., 2002, and in accordance with the guidelines established by the Stanford University APLAC for the humane care and use of animals. Parabiotic pairs were housed separately and maintained on standard rodent chow and acidified water ad libitum.

Tissue processing. Animals were sacrificed at times indicated based on an APLAC-approved protocol that includes assessment of morbidity by >10% loss of weight, scruffy appearance and lethargy. For in vivo studies tetracycline inducible transgenic mice were put on Doxycycline and consecutively tissues from all major organ systems were collected, fixed in 10% neutral buffered formalin, embedded in paraffin, sectioned and stained with hematoxylin and eosin or, to assess for fibrosis, stained with reticulin, trichrome, anti-SMA and c-Jun. Images of histological slides were obtained on a Nikon Eclipse E400 microscope (Nikon, Tokyo, Japan) equipped with a SPOT RT color digital camera model 2.1.1 (Diagnostic Instruments, Sterling Heights, MI). Images were analyzed in Adobe Photoshop (Adobe Systems, San Jose, CA). For flow cytometry, cells were washed in PBS, washed in 2% fetal bovine serum, blocked with Fc-Block (BD PharMingen, San Diego, CA) for 10 min on ice, and stained with primary antibodies in PBS and 2% FCS for 30 min on ice. Flow cytometry was performed on a FACS Aria cytometer (BD Biosciences, San Jose, CA), at least 10,000 events were acquired, and data were analyzed using FlowJo software. The results are presented as graphs and representative dot plots of viable cells selected on the basis of scatter and 7-AAD staining.

Tissue sections (4 μm thickness) were cut from tissue blocks of archival deidentified human biopsies using a microtome for immunofluorescence staining. The sections were baked at 65° C. for 20 min, deparaffinized in xylene and rehydrated via a graded ethanol series. The sections were then immersed in epitope retrieval buffer (10 mM sodium citrate, pH 6) and placed in a pressure cooker for 45 min. The sections were subsequently rinsed twice with dH2O and once with wash buffer (TBS, 0.1% Tween, pH 7.2). Residual buffer was removed by gently touching the surface with a lint-free tissue before incubating with blocking buffer for 30 min. Blocking buffer was subsequently removed, and the sections were stained over-night at 4° C. in a humidified chamber. The following morning, the sections were rinsed twice in wash buffer, secondary antibody (Invitrogen, Carlsbad, CA) were used for visualization of signal. Images of histological slides were obtained on a Leica Eclipse E400 microscope (Leica, Wetzlar, Germany) equipped with a SPOT RT color digital camera model 2.1.1

(Diagnostic Instruments, Sterling Heights, MI). For MIBI, slides were postfixed for 5 min (PBS, 2% glutaraldehyde), rinsed in dH2O and stained with Hematoxylin for 10 s, at the end, the sections were dehydrated via graded ethanol series, air dried using a vacuum desiccator for at least 24 h before imaging. MIBI imaging are performed by NanoSIMS 50L spectroscopy (Cameca, France) at Stanford Nano Shared Facilities (SNSF) and analyzed by using Image with Plugin OpenMIMS (NRIMS available at nrims.hms.harvard).

Expression arrays and computational methods. Time course experiments of c-Jun protein expression in vivo were performed by harvesting bone marrow from mice exposed to doxycycline on day 0 and day 1 and applied to standard Affymetrix mouse arrays. We processed the raw gene expression values with the robust multi-array analysis (RMA) algorithm using BioConductor software. We then filtered out unchanging genes that had an absolute change less than 70 and minimum fold change less than 3 across any two samples. We set thresholds of a minimum of 20 and a maximum of 20,000. Using these preprocessed data, we then identified differentially expressed genes by performing permutation testing with the Comparative Marker Selection algorithm using GenePattern software. We used the signal-to-noise ratio to rank order the genes that distinguish two classes of gene expression samples. In addition to finding differentially expressed genes, we also ran Gene Set Enrichment Analysis to measure enrichment of fibrosis gene sets in our data.

Single cell mass cytometry. Samples were processed as described. Briefly primary bone marrow derived adherent cells from c-Jun mice were induced with doxycycline for 48 hours, labelled with IdU to assess cell proliferation as previously described, washed once with PBS, treated with 25 μM cisplatin for 1 min for live—dead cell discrimination, washed once with RPMI medium containing 10% FBS, treated with 1× TrypLE (Invitrogen) for 5 min at 37° C., dissociated into single-cell suspension by trituration, and washed with PBS containing 0.5% BSA. The cell samples were then fixed with 2% paraformaldehyde at room temperature for 20 min followed by two washes with PBS containing 0.5% BSA. Formaldehyde-fixed cell samples were incubated with metal-conjugated antibodies against surface markers for 1 hr, washed once with PBS containing 0.5% BSA, permeabilized with methanol on ice for 15 min, washed twice with PBS containing 0.5% BSA and then incubated with metal-conjugated antibodies against intracellular molecules for 1 hr. Cells were washed once with PBS containing 0.5% BSA, and then incubated at room temperature for 20 min with an iridium-containing DNA intercalator (Fluidigm) in PBS containing 2% paraformaldehyde. After intercalation/fixation, the cell samples were washed once with PBS containing 0.5% BSA and twice with water before measurement on a CyTOF mass cytometer (Fluidigm). Normalization for detector sensitivity was performed as previously described. After measurement and normalization, the individual FCS files were analyzed by first gating out doublets, debris and dead cell based on cell length, DNA content and cisplatin staining. viSNE maps were generated with software tools available at cytobank.org by considering all surface markers. The F4/80 and CD172a positive or negative subpopulations were gated on viSNE map and the events in each gated were exported for DREVI plot using software package available at c2b2.columbia.edu/danapeer-lab/html/dremi.

Isolation of bone marrow derived fibroblasts. Primary mouse bone marrow derived fibroblasts were generated as previously described by Hanada et al., 1997. The femoral and tibial bones of the donor mice were collected and the adherent soft tissue removed. Both ends of the bones were cut away from the diaphysis with bone scissors, the bone marrow plugs then hydrostatically expelled from the bones and the dispersed cells plated into 10 cm polystyrene tissue culture dishes (Corning, Inc., Corning, N.Y.) and cultured in alpha Dulbecco's modified Eagle's medium (alpha DMEM, Gibco Laboratories) containing selected lots of 10% fetal calf serum (FCS; JR Scientific Inc., Woodland, Calif.), and antibiotics (Gibco Laboratories; penicillin G, 100 U/ml; streptomycin 100 ug/ml, amphotericin B 0.25 ug/ml) at 37° C. in a humidified atmosphere of 5% $CO_2$. Three days later, the medium was changed and non-adherent cells discarded and cultured until confluence was reached.

Transwell migration and proliferation assays. For transwell migration assays Costar transwell chambers were used according to the manufacturer's directions and transmigrated adherent cells were fixed and stained and counted by microscopy after periods of 2 hrs and 24 hrs. Alternatively cytoselect 24 well cell migration assay (12 μm fluorometric format) was purchased from Cell Biolabs, Inc. and used according to the manufacturer's instructions. Briefly, $1 \times 10^4$ cells/ml for mouse fibroblasts and $2 \times 10^4$ cells/ml for human idiopathic lung fibrosis and wildtype fibroblasts were prepared in 300 ul serum free medium containing DMEM with 0.5% BSA, 2 mM $CaCl_2$ and 2 mM $MgCl_2$ and added to the inside of each insert. 500 μL of DMEM containing 20% fetal bovine serum or respective inhibitor have been added to the lower well of the migration plate and incubated for 4 and 72 hours at 37° C. Subsequently the migrated cells were treated with cell detachment solution, lysis buffer and stained and the fluorescence assessed with a fluorescence plate reader at 480 nm/520 nm according to the manufacturer's instructions or manually counted under the microscope. Briefly, for assessment of cell proliferation $6 \times 10^3$ cells/well were plated in duplicate either in 1:1 or 5:1 ratio of human idiopathic lung fibrosis cell line or wildtype fibroblastic cell lines infected with various hairpin directed against human c-JUN in competition with hairpin control infected cells and cell proliferation assessed every 24 h to 72 h by manually counting the total number of cells over a week. Edu staining has been performed to assess cell division as outlined in the click-iT EdU Alexa Fluor 488 Imaging Kit and subsequently confocal pictures of proliferating and migrating cells have been taken in the Stanford Microscopy Core Facility.

In vitro inhibitory screen. Inhibitors such as EGFR/ErbB-2 Inhibitor (324673) (10 μM), PDGFR inhibitor (10 μM and 4 μM), Wortmannin/PI3K (1 μM), GSK/lithium (1 μM), Rapamycin (1 μM), Dapt/Notch (1 μM), Cyclopamin (1 μM), gamma-secretase inhibitor (1 μM), U0126 Mek Inhibitor (10 μM), SB203580 Inhibitor (1 μM), SU5402/FGF1/VEGF (10 μM), PI3 kinase inhibitor Ly294002 (10 μM) and JAK2 Inhibitor II (420132) (10 μM) were purchased from Calbiochem/Selleckchem and dosed as reported previously in the literature, and anti-mouse CD47 clone 3 was used as described previously by Chao et al., 2010 and Majeti et al., 2009.

Anesthesia and CO diffusion testing. Mice were anesthetized with avertin (0.025 ml/g mouse of a 20 mg/ml filter sterilized solution) in saline via intraperitoneal injection.

For the measurement of pulmonary DFCO a gas mixture of CH4/CO/air was used which is similar to the one used in humans for CO diffusion capacity measurements. Anesthetized mice were intubated with a 22-gauge stub needle cannula for the administration of intratracheal doxycycline or DFCO measurements. In a 3-ml syringe 0.8 ml from the commercially available gas mixture was withdrawn, connected with a syringe to the tracheal cannula, and inflated in the lung. After 9 seconds 0.8 ml of gas mixture was withdrawn and further analyzed with mass spectrometry.

Cytokine/chemokine multiplex assay. The following 38 mouse cytokines/chemokines have been quantified by cytokine/chemokine multiplex assay by the Stanford core facility: G-SCF/CSF-3, IL10, IL-3 LIF IL-1B, IL-2, M-CSF, IP-10, VEGF-A, IL4, IL-5, IL-6, TGFB, IFN-a, IL-22, IL-9, IL-13, IL-27, IL-23, IFN-g, IL-12P70, GM-CSF, GRO-a, RANTES, TNF-a, MIP-1a, MCP-3, MCP-1, IL-17A, IL-15/IL-15R, MIP-2, IL-1a, LIX, EOTAXIN, IL-28, IL-18, MIP-1b, IL-31; the mean fluorescent intensity has been measured and the concentrations of each cytokine/chemokine quantified by standard curve method in pg/ml; the experimental details can be found at www.iti.stanford.edu, the Stanford Human Immune Monitoring Center.

In vivo drug application. 6 to 12 week old c-Jun transgenic and control mice were either maintained on Doxycycline containing water or induced intratracheally and concomitantly systemically treated with anti-CD47 antibody (100 µl i.p.), VEGF inhibitor PD173074 (2 mg/kg 1-0-0 i.p.) and a PI3K inhibitor Wortmannin (2 mg/kg 3×/week i.p.). Intratracheal intubation was performed as described previously under isofluran anesthesia using a 22-gauge catheter, a light source and a intubation platform with the administered volume not exceeding >125 ul per mouse.

Protein lysates and Western blot analysis. Protein extracts were prepared by cell lysis in buffer containing protease inhibitors, subjected to SDS-PAGE and analysed by western blot using primary antibodies directed against c-Jun and JunB as indicated throughout.

Cell staining and sorting. Bone marrow mononuclear cells were flushed from the leg bones of c-Jun mice. The cells were then washed and the red cells lysed on ice with RBC lysis buffer (Gentra, Minneapolis, MN). Pooled progenitor populations were sorted and analyzed as previously reported by Na Nakorn et al., 2002 and apoptosis analysis performed using annexin V apoptosis detection kit (BD Pharmingen).

Statistics. The results are expressed as the mean±standard error of the mean (SEM) for n given samples. Data were analyzed using the two-tailed Student's t test or Anova with any p value less than or equal to 0.05 being considered significant. Survival was monitored and analyzed by Kaplan-Meyer analysis. Numbers of recipient mice are indicated and the p value was derived by log-rank test.

Accession numbers. Microarray data are available in the Gene Expression Omnibus (GEO) database under the accession number GSE84838.

Example 2 cJUN Induction Directly Up-Regulates CD47 and Causes Fatty Liver

Figure 15:
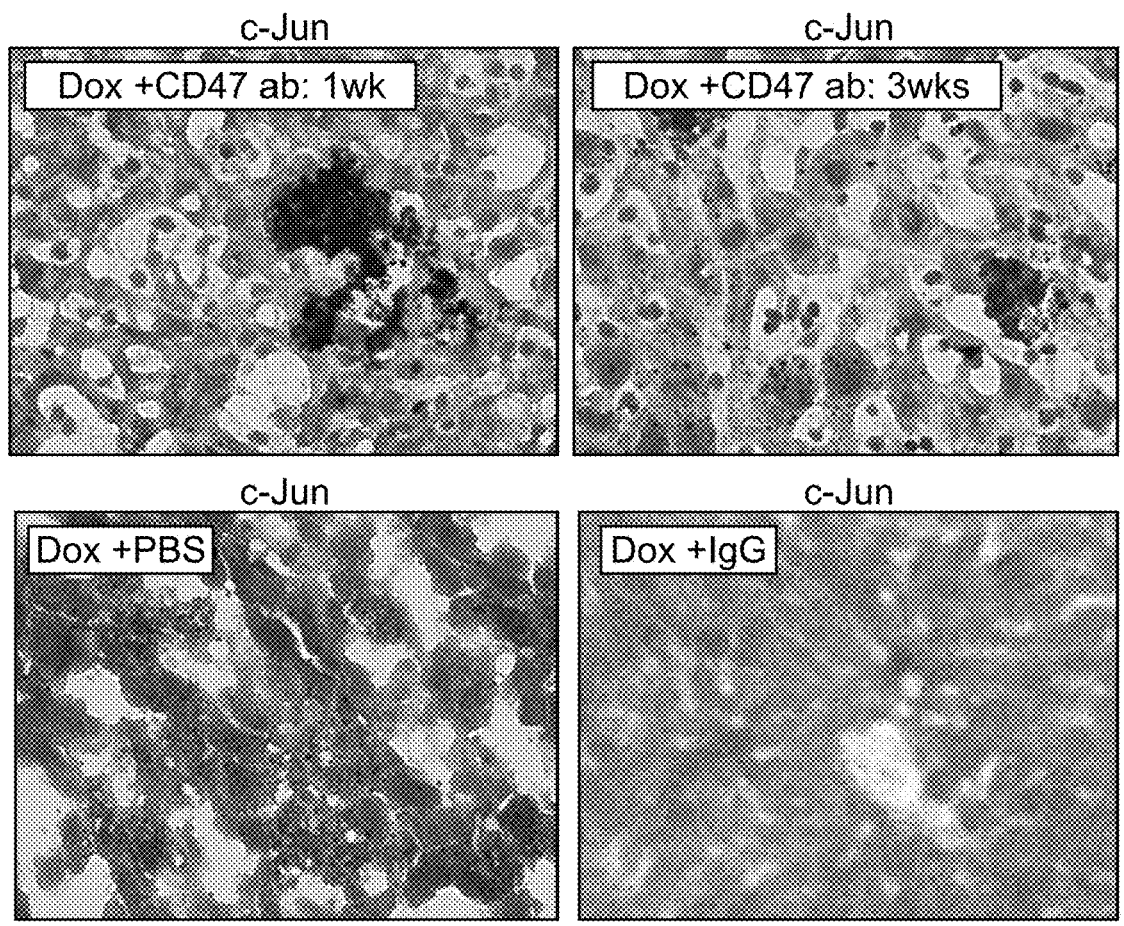
FIG. 15. CD47 blockade induces macrophage mediated fat clearance in fatty liver in c-JUN induced mice (red large clusters are lipid filled foamy macrophages).

CD47 blockade recruits macrophages and facilitates fat clearance in c-JUN mediated fatty liver. As shown in FIG. 15, CD47 blockade induces macrophage mediated fat clearance in c-JUN mediated fatty liver (large clusters are lipid filled foamy macrophages). A therapeutic strategy is provided for treatment of fatty liver or NASH (non-alcoholic steatohepatitis) in humans by administering an effective dose of an agent that inhibits the interaction between CD47 and SIRPα.

Material and Methods

For the fatty liver in vivo studies the flp-in tetO-c-JUN rosa mice were put on Doxycycline in the drinking water, which induces cJUN expression ubiquitously in the mice, but highly in hepatocytes. We have established additional mouse models of fatty liver by crossing the flp-in teO-cJUN mice to the albumin CRE rtTA mice and Cebp rtTA mice, and both additional mouse strains developed a striking fatty liver phenotype.

In contrast to the systemic cJUN induction under the Rosa promoter, cJUN is only induced in hepatocytes in these two liver restricted models of cJUN expression. The advantage of these mice is that they are much longer lived which allows for more long-term disease modeling and inhibitor testing. Indeed, 7-10 days after systemic/liver restricted c-Jun induction we noticed small and large vacuoles in the majority of hepatocytes which were positive by oil-red O, a stain which highlights lipids.

We subsequently attempted to reverse fatty liver in c-JUN mice by treating mice systemically with intraperitoneal injections both prospectively and retrospectively after established fatty liver disease. We used two different inhibitory approaches: 1) CD47 blockade with Clone 3 anti-CD47 antibody for one or two weeks and 2) PDGFRalpha blockade for 3 weeks and found that blocking either pathway independently prevented or reversed fatty liver.

Fatty liver was assessed in liver tissues after fixation in 10% formalin by routine histopathology on Hematoxylin/Eosinophil and trichrome stains by a trained pathologist. Fat content of the liver was quantified by Oil-Red O staining on frozen sections. In mice who received treatment with clone 3 and decreased/resolved the fat content of hepatocytes but also the overall fat content of the liver, we noticed increased numbers of macrophages in the liver, in particular large clusters of foamy macrophages which appeared loaded with fat on oil-red O stain, implying that macrophages take up the excessive fat thus resolving fatty liver.

What is claimed is:

1. A method for in vivo treatment of liver fibrosis in a mammalian patient, the method comprising:
   administering a dose of an antibody that neutralizes CD47 to the mammalian patient effective to reduce fibrosis, wherein the liver fibrosis is associated with non-alcoholic fatty liver disease (NAFLD).

2. The method of claim 1, wherein the NAFLD is non-alcoholic steatohepatitis (NASH).

3. The method of claim 1, wherein the antibody is co-administered with an anti-c-Jun agent.

4. The method of claim 1, wherein the antibody is co-administered with an anti-PI3K agent.

5. The method of claim 1, wherein the antibody is co-administered with an anti-VEGF agent.

6. The method of claim 1, wherein the antibody is co-administered with an anti-PDGFR agent.

7. The method of claim 1, wherein pathogenic fibroblasts of the fibrosis have elevated levels of c-Jun.

8. The method of claim 1, wherein the patient has been diagnosed by a method comprising:
   determining the presence of elevated levels of CD47 in a patient biological sample.

9. The method of claim 1, wherein the patient has been diagnosed by a method comprising:
   determining the presence of elevated levels of c-Jun in a patient biological sample.

10. The method of claim 1, wherein the patient has been is analyzed after treatment by a method comprising:
    determining the extent of fibrosis in a patient biological sample.

* * * * *